United States Patent
Sihlanick et al.

(10) Patent No.: US 11,690,959 B2
(45) Date of Patent: Jul. 4, 2023

(54) DOSE MEASUREMENT SYSTEMS AND METHODS

(71) Applicant: Bigfoot Biomedical, Inc., Milpitas, CA (US)

(72) Inventors: Kevin Sihlanick, Cambridge, MA (US); Richard Whalley, Cambridge, MA (US); Matthew Legrand, Cambridge, MA (US); James White, Cambridge, MA (US); Jeffrey Carothers, Somerville, MA (US)

(73) Assignee: BIGFOOT BIOMEDICAL, INC., Milpitas, CA (US)

( * ) Notice: Subject to any disclaimer, the term of this patent is extended or adjusted under 35 U.S.C. 154(b) by 0 days.

(21) Appl. No.: 17/481,834

(22) Filed: Sep. 22, 2021

(65) Prior Publication Data
US 2022/0008658 A1    Jan. 13, 2022

Related U.S. Application Data

(63) Continuation of application No. 16/880,352, filed on May 21, 2020, now Pat. No. 11,389,595, which is a
(Continued)

(51) Int. Cl.
*A61M 5/168* (2006.01)
*A61M 5/315* (2006.01)
(Continued)

(52) U.S. Cl.
CPC ....... *A61M 5/31535* (2013.01); *A61B 5/4839* (2013.01); *A61M 5/168* (2013.01);
(Continued)

(58) Field of Classification Search
CPC ...... A61M 2205/50; A61M 2205/3306; A61M 5/20; A61M 2205/502; A61M 5/168;
(Continued)

(56) References Cited

U.S. PATENT DOCUMENTS 4,286,646 A    9/1981  Tauber et al.
4,857,738 A    8/1989  Myers et al.
(Continued)

FOREIGN PATENT DOCUMENTS

CN    1906485    1/2007
CN    101262950  9/2008
(Continued)

OTHER PUBLICATIONS

Office Action dated Jan. 17, 2019 from Canadian Application No. 2,874,331, 4 pages.
(Continued)

*Primary Examiner* — Michael P Stafira
(74) *Attorney, Agent, or Firm* — Hamre, Schumann, Mueller & Larson, P.C.

(57) ABSTRACT

Embodiments described herein generally relate to devices, systems and methods for measuring a volume or number of doses remaining in a drug delivery device that is used for delivering a dose to a patient. In some embodiments, a dose measurement system for measuring the liquid volume in a container includes a light guide disposed and configured to reflect electromagnetic radiation toward the container. The dose measurement system also includes a light guide disposed and configured to emit electromagnetic radiation into the light guide. A plurality of sensors are located in the apparatus that are optically coupleable to the light guide and are disposed and configured to detect the electromagnetic radiation emitted by at least a portion of the light guide. The apparatus also includes a processing unit configured to receive data representing the portion of the detected electromagnetic radiation from each of the plurality of sensors. The processing unit is further operable to convert the received data into a signature representative of the electromagnetic radiation detected by the plurality of sensors.

17 Claims, 33 Drawing Sheets

Related U.S. Application Data continuation of application No. 16/209,580, filed on Dec. 4, 2018, now Pat. No. 10,695,501, which is a continuation of application No. 15/649,224, filed on Jul. 13, 2017, now Pat. No. 10,183,120.

(60) Provisional application No. 62/362,946, filed on Jul. 15, 2016.

(51) Int. Cl.
| | | |
|---|---|---|
| *G01F 11/02* | (2006.01) | |
| *G01F 17/00* | (2006.01) | |
| *G01F 23/284* | (2006.01) | |
| *G01F 23/292* | (2006.01) | |
| *A61M 5/20* | (2006.01) | |
| *A61B 5/00* | (2006.01) | |
| *A61M 5/31* | (2006.01) | |
| *A61B 5/1455* | (2006.01) | |
| *A61M 5/172* | (2006.01) | |
| *A61M 5/32* | (2006.01) | |
| *G01N 27/02* | (2006.01) | |

(52) U.S. Cl.
CPC .......... *A61M 5/16886* (2013.01); *A61M 5/20* (2013.01); *A61M 5/31* (2013.01); *A61M 5/31541* (2013.01); *A61M 5/31566* (2013.01); *A61M 5/31568* (2013.01); *G01F 11/025* (2013.01); *G01F 17/00* (2013.01); *G01F 23/2845* (2013.01); *G01F 23/2927* (2013.01); *A61B 5/1455* (2013.01); *A61M 5/16804* (2013.01); *A61M 5/172* (2013.01); *A61M 2005/2006* (2013.01); *A61M 2005/3254* (2013.01); *A61M 2205/18* (2013.01); *A61M 2205/3306* (2013.01); *A61M 2205/3317* (2013.01); *A61M 2205/3379* (2013.01); *A61M 2205/3553* (2013.01); *A61M 2205/3561* (2013.01); *A61M 2205/3576* (2013.01); *A61M 2205/3584* (2013.01); *A61M 2205/3592* (2013.01); *A61M 2205/50* (2013.01); *A61M 2205/502* (2013.01); *A61M 2205/584* (2013.01); *G01N 27/02* (2013.01)

(58) Field of Classification Search
CPC .......... A61M 5/31566; A61M 2205/18; A61M 2205/3379; A61M 2205/3592; A61M 2005/2006; A61M 2005/3254; A61M 2205/3317; A61M 2205/3553; A61M 2205/3561; A61M 2205/3576; A61M 2205/3584; A61M 2205/584; A61M 5/16804; A61M 5/16886; A61M 5/172; A61M 5/31; A61M 5/31535; A61M 5/31541; A61M 5/31568; A61M 2205/587; A61M 2025/0019; A61M 2205/3368; A61M 2205/3606; A61M 2205/581; A61M 2205/8206; A61M 25/00; A61M 3/0279; A61M 2005/1406; A61M 2005/3125; A61M 2039/224; A61M 2205/3389; A61M 2205/582; A61M 2205/583; A61M 25/0662; A61M 39/223; A61M 5/145; A61M 5/1452; A61M 5/14566; A61M 5/44; A61M 1/3681; A61M 2202/0468; A61M 2205/276; A61M 5/007; A61M 5/14248; A61M 5/1684; A61M 5/1785; A61M 5/3129; A61M 5/365; A61M 1/0001; A61M 1/0023; A61M 1/3683; A61M 1/3693; A61M 1/79; A61M 11/041; A61M 11/042; A61M 15/00; A61M 15/0021; A61M 15/0065; A61M 15/0086; A61M 15/06; A61M 2005/14268; A61M 2016/0021; A61M 2205/11; A61M 2205/3569; A61M 2205/3653; A61M 2205/505; A61M 2205/52; A61M 2205/6063; A61M 2205/7536; A61M 2205/8237; A61M 2205/8293; A61M 2209/084; A61M 2209/086; A61M 25/002; A61M 25/0084; A61M 31/002; A61M 35/00; A61M 35/003; A61M 5/1407; A61M 5/142; A61M 5/14232; A61M 5/14244; A61M 5/158; A61M 5/1723; A61M 5/24; A61M 5/31525; A61M 5/425; G01F 23/2927; G01F 11/025; G01F 17/00; G01F 23/2845; G01F 11/029; G01F 23/292; G01N 27/02; G01N 21/4795; G01N 33/54313; G01N 15/14; G01N 15/1425; G01N 15/1459; G01N 2015/0038; G01N 2015/1493; G01N 21/6486; G01N 33/585; G01N 21/6402; G01N 21/6408; G01N 21/6456; G01N 2021/6482; G01N 21/1702; G01N 21/31; G01N 21/3504; G01N 21/51; G01N 21/532; G01N 21/59; G01N 21/645; G01N 2291/021; G01N 29/036; G01N 29/42; G01N 33/54373; G01N 11/00; G01N 15/1468; G01N 2001/1006; G01N 2021/0346; G01N 2021/035; G01N 2021/1787; G01N 2021/6421; G01N 2021/6439; G01N 2021/6441; G01N 2033/0091; G01N 2035/00158; G01N 21/01; G01N 21/05; G01N 21/253; G01N 21/255; G01N 21/33; G01N 21/35; G01N 21/3554; G01N 21/359; G01N 21/47; G01N 21/552; G01N 21/5907; G01N 21/6452; G01N 21/648; G01N 21/7703; G01N 21/78; G01N 21/8422; G01N 2201/0221; G01N 2201/0806; G01N 27/327; G01N 33/186; G01N 33/52; G01N 33/54353; G01N 33/54366; G01N 35/00732

See application file for complete search history.

(56) References Cited

U.S. PATENT DOCUMENTS

| | | | |
|---|---|---|---|
| 4,904,878 A | * | 2/1990 | Gipp .................. G01F 23/2921 |
| | | | 250/577 |
| 4,952,055 A | | 8/1990 | Wyatt |
| 5,065,037 A | | 11/1991 | Finney et al. |
| 5,184,510 A | | 2/1993 | Rossman |
| 5,303,585 A | | 4/1994 | Lichte |
| 5,452,076 A | | 9/1995 | Schopper et al. |
| 5,556,002 A | | 9/1996 | Green |
| 5,569,212 A | | 10/1996 | Brown |
| 5,593,390 A | | 1/1997 | Castellano et al. |
| 5,606,125 A | | 2/1997 | Lyons et al. |
| 5,628,309 A | | 5/1997 | Brown |
| 5,720,733 A | | 2/1998 | Brown |
| 5,748,091 A | | 5/1998 | Kim |
| 5,782,814 A | | 7/1998 | Brown et al. |
| 5,792,117 A | | 8/1998 | Brown |
| 5,938,642 A | | 8/1999 | Burroughs et al. |
| 6,068,615 A | | 5/2000 | Brown et al. |
| 6,090,473 A | | 7/2000 | Yoshikawa et al. |
| 6,110,148 A | | 8/2000 | Brown et al. |
| 6,113,578 A | | 9/2000 | Brown |

(56) References Cited

U.S. PATENT DOCUMENTS

| | | | |
|---|---|---|---|
| 6,270,455 B1 * | 8/2001 | Brown | G16H 20/17 |
| | | | 128/920 |
| 6,352,523 B1 | 3/2002 | Brown et al. | |
| 6,452,158 B1 | 9/2002 | Whatley et al. | |
| 6,505,509 B2 | 1/2003 | Gualtieri | |
| 6,685,678 B2 | 2/2004 | Evans et al. | |
| 7,049,622 B1 * | 5/2006 | Weiss | G01F 23/292 |
| | | | 73/290 R |
| 7,074,209 B2 | 7/2006 | Evans et al. | |
| 7,115,113 B2 | 10/2006 | Evans et al. | |
| 7,408,632 B2 | 8/2008 | Moore et al. | |
| 7,498,563 B2 | 3/2009 | Mandro et al. | |
| 7,772,008 B2 | 8/2010 | Curtis et al. | |
| 8,079,245 B1 | 12/2011 | Owens et al. | |
| 8,197,449 B2 | 6/2012 | Nielsen et al. | |
| 8,221,356 B2 | 7/2012 | Enggaard et al. | |
| 8,348,904 B2 | 1/2013 | Petersen | |
| 8,618,485 B1 | 12/2013 | Lockhart | |
| 8,817,258 B2 | 8/2014 | Whalley et al. | |
| 9,138,091 B2 * | 9/2015 | Zhao | G01F 23/18 |
| 9,250,111 B2 | 2/2016 | Whalley et al. | |
| 9,255,830 B2 * | 2/2016 | Whalley | A61M 5/16804 |
| 9,638,564 B2 | 5/2017 | Whalley et al. | |
| 9,642,968 B2 | 5/2017 | Whalley et al. | |
| 10,183,120 B2 | 1/2019 | Sihlanick et al. | |
| 10,190,901 B2 | 1/2019 | Whalley et al. | |
| 10,255,991 B2 | 4/2019 | White et al. | |
| 10,258,743 B2 | 4/2019 | Whalley et al. | |
| 10,684,156 B2 | 6/2020 | Whalley et al. | |
| 10,695,501 B2 | 6/2020 | Whalley et al. | |
| 2001/0056258 A1 | 12/2001 | Evans | |
| 2004/0089067 A1 | 5/2004 | Frank | |
| 2005/0177137 A1 | 8/2005 | Kipfer | |
| 2006/0154327 A1 * | 7/2006 | Bachur | C12M 41/34 |
| | | | 702/19 |
| 2006/0178578 A1 * | 8/2006 | Tribble | G01F 25/0092 |
| | | | 382/128 |
| 2007/0143062 A1 | 6/2007 | Memmott et al. | |
| 2007/0213949 A1 | 9/2007 | Artiuch | |
| 2008/0108885 A1 | 5/2008 | Colvin, Jr. | |
| 2008/0113337 A1 | 5/2008 | Sakudo et al. | |
| 2008/0316612 A1 | 12/2008 | Hyde et al. | |
| 2009/0159654 A1 | 6/2009 | Grimard | |
| 2009/0299279 A1 * | 12/2009 | Richter | A61M 5/24 |
| | | | 604/93.01 |
| 2010/0030136 A1 | 2/2010 | Dacquay et al. | |
| 2010/0080086 A1 | 4/2010 | Wright et al. | |
| 2010/0134303 A1 * | 6/2010 | Perkins | A61M 5/1684 |
| | | | 340/619 |
| 2010/0213392 A1 | 8/2010 | Hatzav et al. | |
| 2011/0102796 A1 | 5/2011 | Shang et al. | |
| 2011/0184343 A1 | 7/2011 | Veit et al. | |
| 2011/0270214 A1 | 11/2011 | Joergensen et al. | |
| 2011/0292399 A1 | 12/2011 | Alphonse | |
| 2011/0295215 A1 * | 12/2011 | Nielsen | G16H 20/17 |
| | | | 604/257 |
| 2011/0313395 A1 | 12/2011 | Krulevitch et al. | |
| 2012/0234074 A1 | 9/2012 | Hagen | |
| 2012/0268741 A1 * | 10/2012 | Pommereau | A61M 5/14566 |
| | | | 356/343 |
| 2013/0030405 A1 | 1/2013 | Hartman et al. | |
| 2013/0310756 A1 * | 11/2013 | Whalley | A61M 5/31 |
| | | | 604/189 |
| 2014/0130745 A1 | 5/2014 | Van Halsema et al. | |
| 2015/0115158 A1 | 4/2015 | Fu et al. | |
| 2015/0290396 A1 * | 10/2015 | Nagar | G16H 20/13 |
| | | | 340/540 |
| 2015/0362350 A1 | 12/2015 | Miller et al. | |
| 2016/0030673 A1 | 2/2016 | White et al. | |
| 2016/0061646 A1 | 3/2016 | Mestivier et al. | |
| 2017/0246399 A1 | 8/2017 | Forlani et al. | |
| 2017/0333645 A1 * | 11/2017 | Alizoti | A61M 15/002 |
| 2018/0299317 A1 | 10/2018 | Truong et al. | |
| 2020/0023134 A1 | 1/2020 | Whalley et al. | |
| 2020/0027533 A1 | 1/2020 | White et al. | |

FOREIGN PATENT DOCUMENTS

| | | | |
|---|---|---|---|
| CN | 102301207 | 12/2011 | |
| CN | 102428315 A * | 4/2012 | G02B 6/0041 |
| CN | 103354800 | 10/2013 | |
| CN | 105716680 | 6/2016 | |
| DE | 10 2006 047537 | 12/2011 | |
| EP | 1382946 | 1/2004 | |
| EP | 1 920 793 | 5/2008 | |
| JP | H08297036 A * | 11/1996 | |
| JP | 2000-279515 | 10/2000 | |
| JP | 2004008798 A * | 1/2004 | A61M 5/007 |
| JP | 2010-505475 | 2/2010 | |
| JP | 2013-126532 | 6/2013 | |
| WO | 2010/088591 | 8/2010 | |
| WO | 2010/098929 | 9/2010 | |
| WO | 2011/108225 | 9/2010 | |
| WO | 2011/032960 | 3/2011 | |
| WO | 2011/084713 | 7/2011 | |
| WO | 2012/062843 | 5/2012 | |
| WO | 2012/126975 | 9/2012 | |
| WO | WO-2013061248 A1 * | 5/2013 | A61M 11/00 |
| WO | WO-2015143058 A1 * | 9/2015 | A61M 5/31568 |

OTHER PUBLICATIONS

Office Action dated Dec. 11, 2019 for Canadian Application No. 2,874,331,4 pages.

Office Action dated Jun. 28, 2016 from Chinese Application No. 201380036003.4 w/English language translation, 19 pages.

Office Action dated Apr. 12, 2017 from Chinese Application No. 201380036003 4 w/English language translation, 15 pages.

Office Action dated Mar. 27, 2018 from Chinese Application No. 20130036003.4 w/English translation, 7 pages.

Communication pursuant to Article 94(3) dated Jan. 31, 2018 issued by the European Patent Office from European Application No. 13793067.3, 6 pages.

Extended European Search Report dated Jun. 7, 2016 from European Application No. 13793067.3, 21 pages.

Notice of Reasons for Rejection dated Feb. 17, 2017 from Japanese Application No. 2015-514106 w/English translation, 15 pages.

Decision of Rejection dated Nov. 1, 2017 from Japanese Application No. 2015-514106, w/English translation, 13 pages.

Notice of Reasons for Rejection dated Mar. 28, 2019 from Japanese Application No. 2015-514106, w/English translation, 14 pages.

Appeal Decision dated Mar. 23, 2020 for Japanese Application No. 2015-514106, w/English translation, 24 pages.

International Search Report and Written Opinion dated Oct. 21, 2013 from International Application No. PCT/US2013/041982, 10 pages.

Office Action dated Dec. 14, 2018 from Chinese Application No. 201580040532.0, w/English translation, 10 pages.

Office Action dated Jul. 19, 2019 from Chinese Application No. 201580040532.0, w/English translation, 21 pages.

Extended European Search Report dated Mar. 8, 2018 from European Application No. 15826907.6, 10 pages.

Communication pursuant to Article 94(3) dated Mar. 22, 2019 from European Application No. 15826907.6, 5 pages.

Notice of Reasons for Rejection dated Apr. 9, 2019 from Japanese Application No. 2016-572816, w/English translation.

Decision of Rejection dated Mar. 16, 2020 for Japanese Application No. 2016-572816, w/English translation, 9 pages.

International Search Report and Written Opinion dated Nov. 20, 2015 for International Application No. PCT/US2015/043417, 8 pages.

International Search Report and Written Opinion dated Nov. 17, 2017 from International Application No. PCT/US2017/041982, 15 pages.

Non-Final Office Action dated Feb. 28, 2014 from U.S. Appl. No. 13/796,889, 10 pages.

(56) References Cited

OTHER PUBLICATIONS

Non-Final Office Actions dated Jun. 10, 2015 from U.S. Appl. No. 14/334,181, 12 pages.
Non-Final Office Action dated Jun. 15, 2016 from U.S. Appl. No. 14/982,650, 11 pages.
Non-Final Office Action dated Jun. 17, 2016 from U.S. Appl. No. 14/982,668, 10 pages.
Non-Final Office Action dated Dec. 22, 2017 from U.S. Appl. No. 15/464,466, 12 pages.
Non-Final Office Action dated Jul. 25, 2018 from U.S. Appl. No. 15/477,444, 13 pages.
Non-Final Office Action dated Jun. 11, 2019 for U.S. Appl. No. 16/235,286, 15 pages.
Non-Final Office Action dated Feb. 4, 2020 for U.S. Appl. No. 16/283,084, 11 pages.
Non-Final Office Action dated Jun. 29, 2018 from U.S. Appl. No. 14/816,634, 15 pages.
Non-Final Office Action dated Feb. 14, 2018 from U.S. Appl. No. 15/649,224, 15 pages.
Non-Final Office Action dated Aug. 29, 2019 from U.S. Appl. No. 16/209,580, 9 pages.
Office Action dated Jul. 2, 2020 for Chinese Application No. 201910115230.5, with English translation, 18 pages.
Office Action dated Jul. 3, 2020 for Chinese Application No. 201780043779.7, with English translation, 30 pages.
Examination Report issued for European Patent Application No. 17828483.2, dated Sep. 13, 2021, 4 pages.

\* cited by examiner

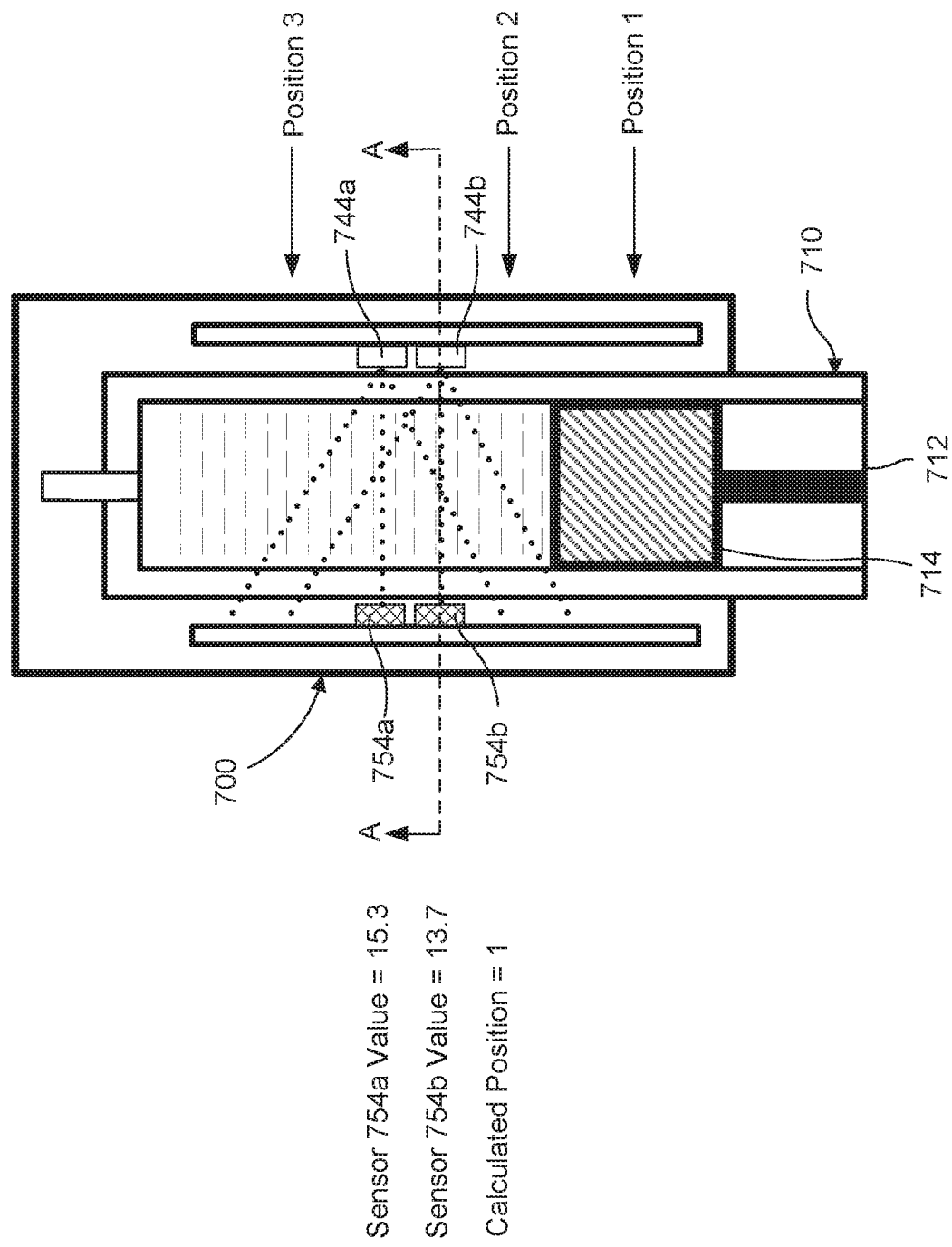

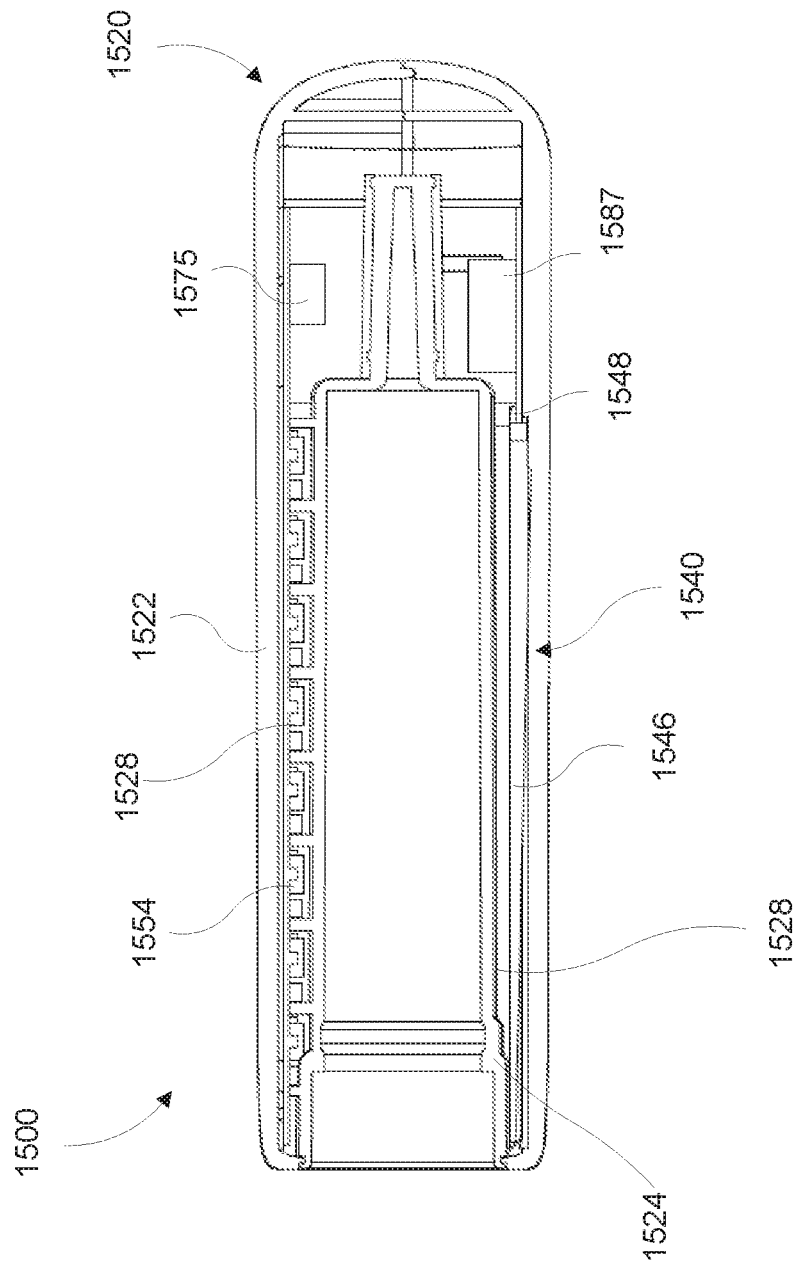

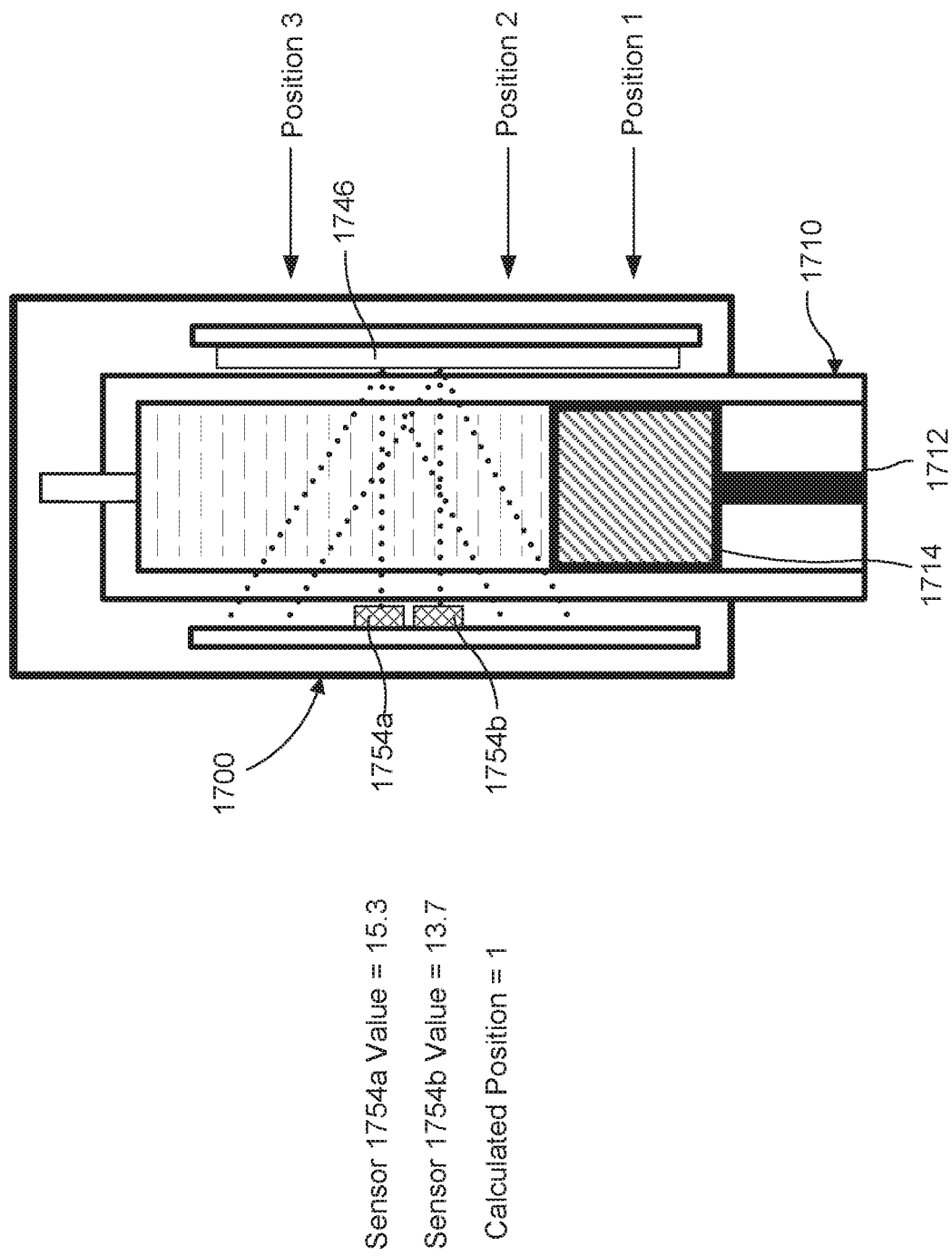

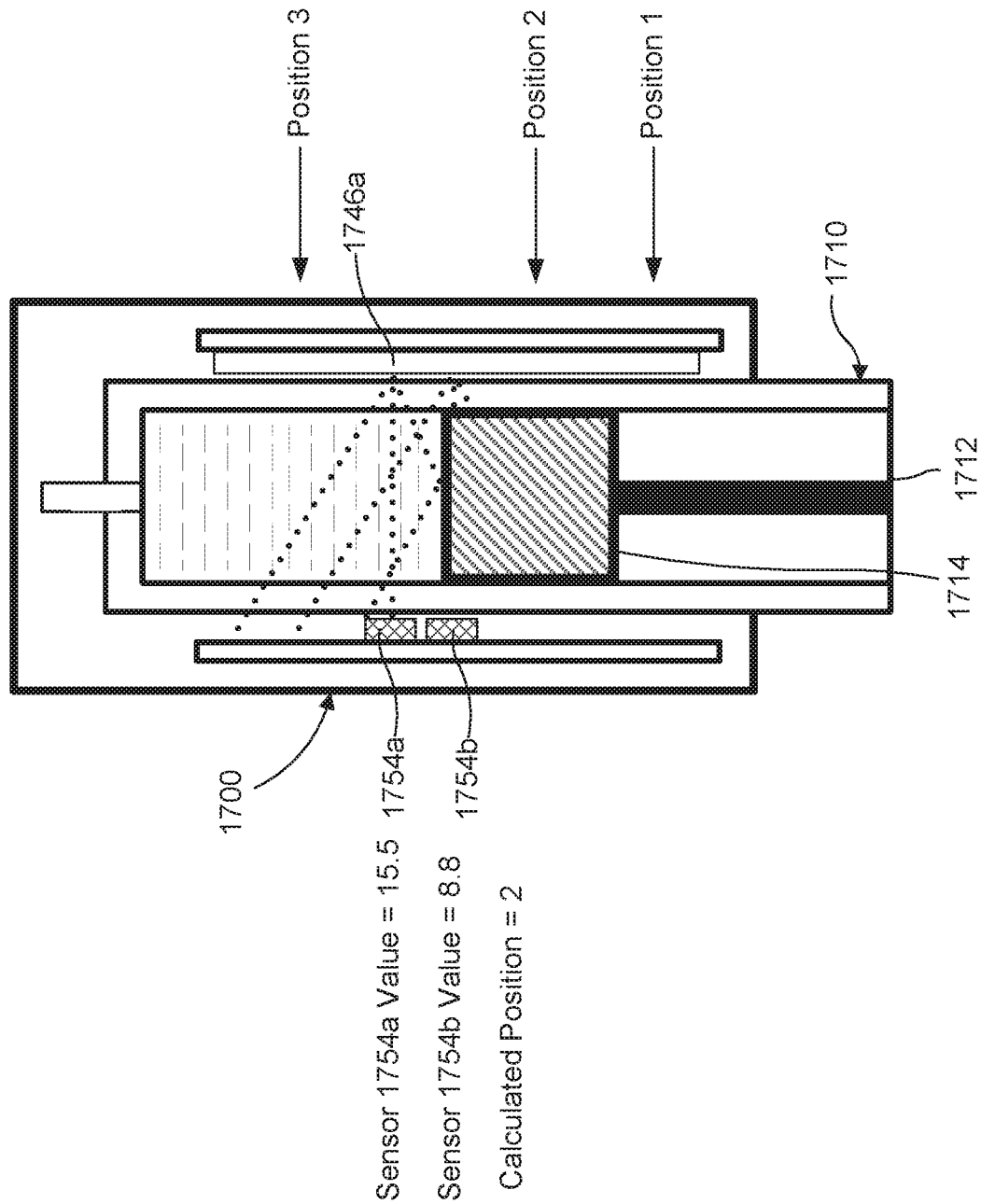

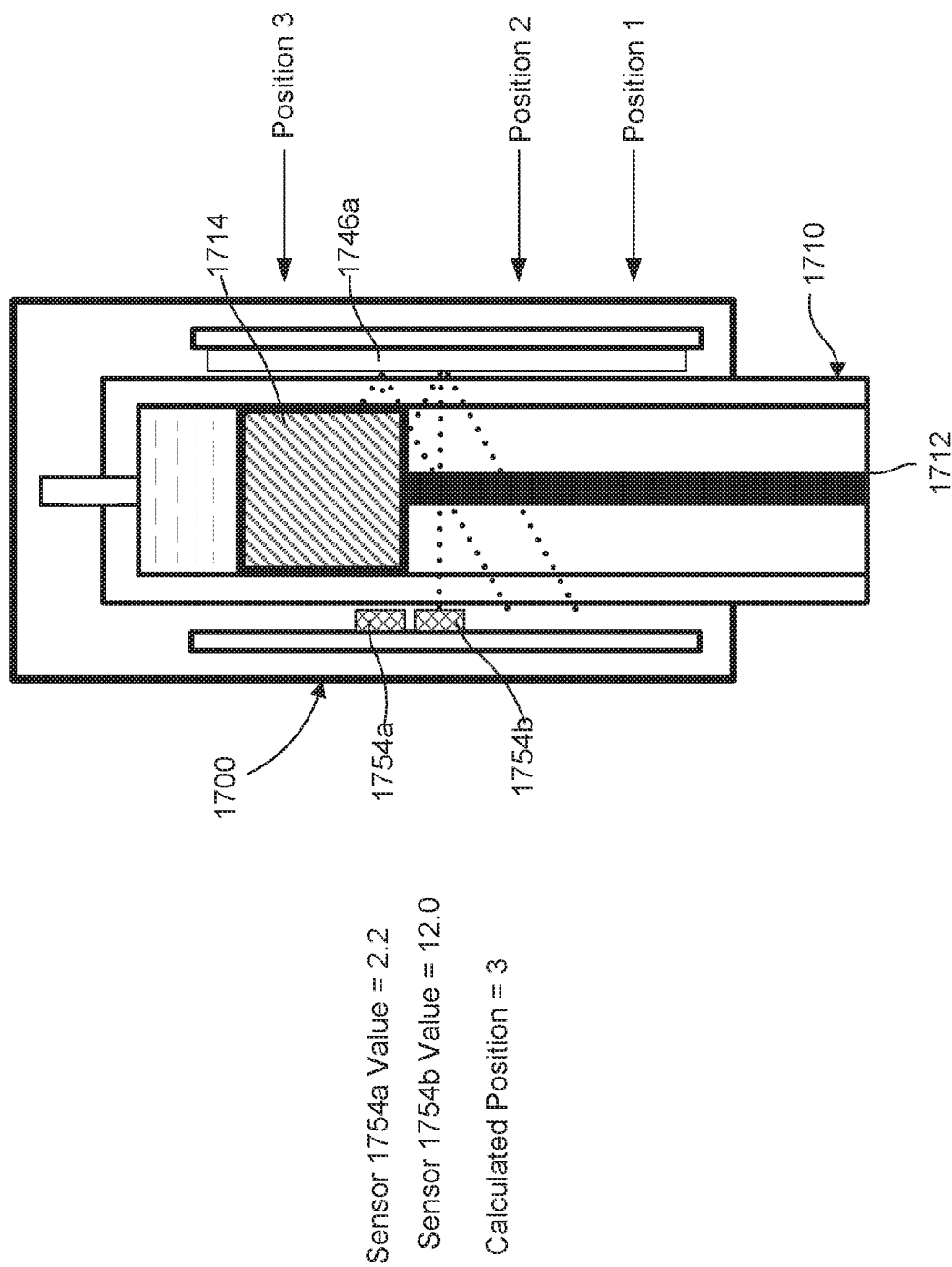

DOSE MEASUREMENT SYSTEMS AND METHODS

CROSS-REFERENCE TO RELATED APPLICATIONS

This application is a continuation of U.S. application Ser. No. 16/880,352 filed on May 21, 2020, which is a continuation of U.S. application Ser. No. 16/209,580 filed on Dec. 4, 2018, which is a continuation of U.S. application Ser. No. 15/649,224 filed on Jul. 13, 2017, which claims the priority benefit, under 35 U.S.C. § 119(e), of U.S. Application No. 62/362,946, entitled "Dose Measurement Systems and Methods," filed on Jul. 15, 2016, the disclosures of which are incorporated herein by reference in their entirety.

BACKGROUND

Embodiments described herein relate generally to devices, systems, and methods for measuring a quantity of a liquid disposed in a container, and in particular to measuring a volume or number of doses remaining in a drug delivery device.

Many chronic disease patients are prescribed medications that need to be self-administered, administered by a caregiver, or administered by an automated or semi-automated delivery system using injection pens or similar drug delivery devices. For example, patients diagnosed with Type I or II diabetes need to regularly check their blood glucose levels and self-administer an appropriate dose of insulin using an injection pen. In order to monitor the efficacy of the medication, dose information must be recorded. The process of manually logging dose information, particularly in an uncontrolled setting, is tedious and error prone. Patients often forget to log the dose information when administering medicine. In addition, many such patients may be minors or elderly who cannot efficiently and/or accurately track the dose information.

Incomplete dosage records hinder the ability of the patient to self-manage disease conditions and prevent caretakers from adjusting care plans through behavioral insights. Lack of adherence to target dosage schedules for injectable medicine may result in an increased need for critical care, which results in a significant increase in health care costs in countries around the world.

Thus, a need exists for better technological aids to assist patients in improving their ability to self-manage disease treatment. Such aids not only improve patient awareness and education about their health, but also assist caregivers in better monitoring patient health. In particular, there is a need for systems, devices, and methods that facilitate data acquisition on patient behavior and that allow that data to be used to reduce the incidence of hospital visits (e.g., re-admission), as well as to inform and educate patients, care providers, family and financial service providers.

SUMMARY

An apparatus for measuring liquid volume in a container includes a light source disposed and configured to emit electromagnetic radiation, a light guide disposed and configured to receive at least a portion of the emitted electromagnetic radiation, the light guide distributing at least a portion of the received electromagnetic radiation over a length of the light guide and directing the distributed electromagnetic radiation toward the container, a plurality of sensors optically coupleable to the light guide, each sensor of the plurality of sensors disposed and configured to detect at least a portion of the distributed electromagnetic radiation, and a processing unit configured to receive data representative of at least the portion of the detected electromagnetic radiation from each of the plurality of sensors, the processing unit operable to convert the received data into a signature representative of the electromagnetic radiation detected by the plurality of sensors.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Other systems, processes, and features will become apparent to those skilled in the art upon examination of the following drawings and detailed description. It is intended that all such additional systems, processes, and features be included within this description, be within the scope of the present invention, and be protected by the accompanying claims.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 11A-11C are cross-sectional views of a dose measurement system, in a first, second and third configuration, respectively, in accordance with some embodiments.

FIG. 24 is a cross-sectional side view of the dose measurement system of FIG. 18 in accordance with some embodiments.

FIGS. 26A-26C are cross-sectional schematic illustrations of a dose measurement system, in a first, second, and third configuration, respectively, in accordance with some embodiments.

DETAILED DESCRIPTION

Figure 1:
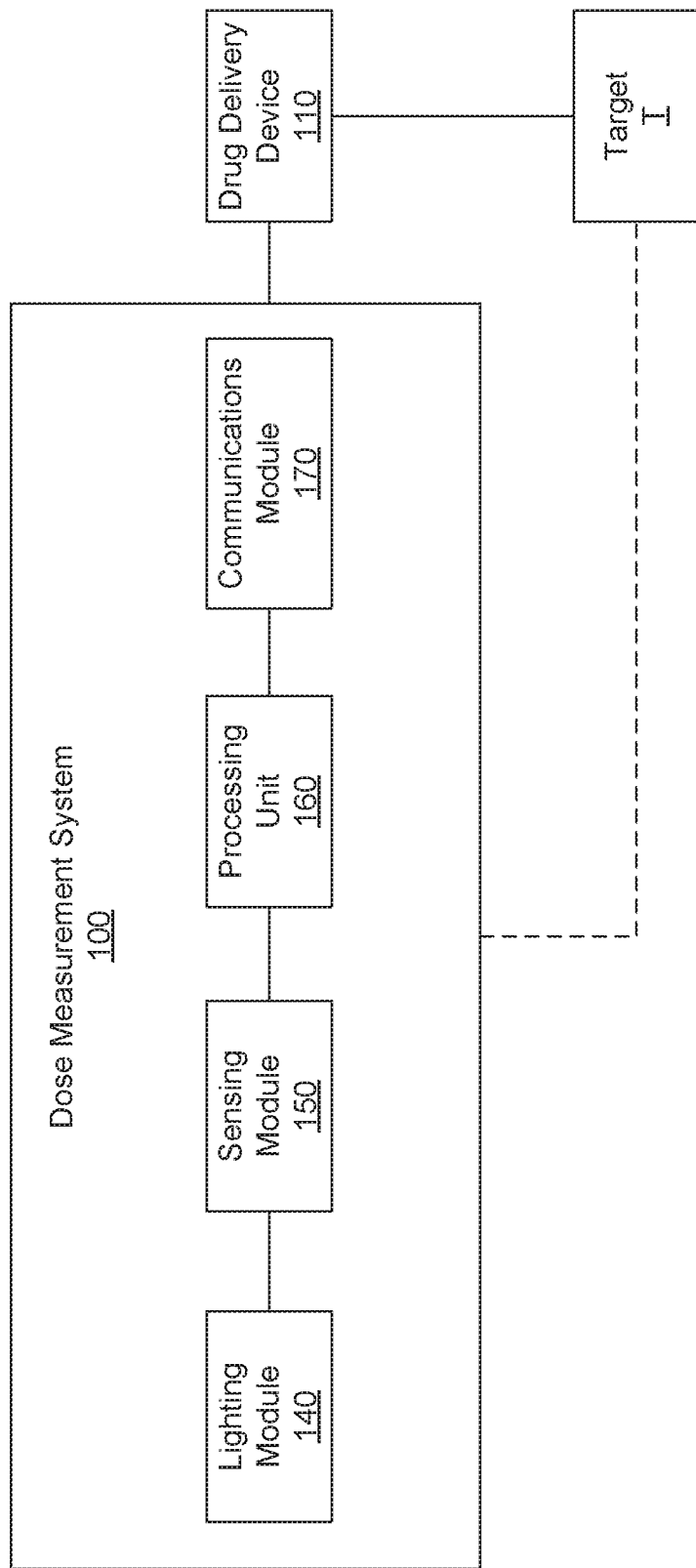
FIG. 1 is a schematic block diagram of a dose measurement system in accordance with some embodiments.

Embodiments described herein relate generally to devices, systems and methods for measuring a quantity of a liquid disposed in a container, and in particular to a volume or number of doses remaining in a drug delivery device. In some embodiments, a dose measurement system for measuring the liquid volume in a container includes a light source and/or light guide disposed and configured to emit/distribute electromagnetic radiation toward the container. A plurality of sensors are optically coupleable to the light source and are disposed and configured to detect at least a portion of the electromagnetic radiation emitted/distributed by the light source and/or light guide. The apparatus also includes a processing unit configured to receive data representing the portion of the detected electromagnetic radiation from each of the plurality of sensors and to convert the received data into a signature representative of the electromagnetic radiation detected by the plurality of sensors.

In some embodiments, a method of estimating a volume of liquid in a drug delivery device includes causing a light source and/or light guide to emit/distribute electromagnetic radiation toward a drug container and detecting a signature of the emitted/distributed electromagnetic radiation through the drug container with a plurality of sensors. The detected signature is then compared to a plurality of reference signatures to determine the volume of liquid in the drug container. Each of the plurality of reference signatures correspond to a volume level remaining in the drug container. In some embodiments, detecting the signature of the emitted/distributed electromagnetic radiation through the drug container includes detecting at least a portion of the electromagnetic radiation emitted/distributed from the light source and/or light guide. The portion of the electromagnetic radiation detected by each of the plurality of sensor devices may be compiled into the signal signature.

In some embodiments, the method also includes calculating a dose delivered to a patient based on the volume of liquid in the drug container. In some embodiments, the dose delivered to a patient is compared with a patient medication schedule to monitor compliance. The method may further include correcting the signal signature for background light which can contribute to noise. The correction may include comparing the signal signature with a background signature detected by the plurality of sensors in a dark state of the light source. In some embodiments, the method also includes generating the plurality of reference signatures by recording the signature for a range of dose volumes in the drug container. The method also may include associating the signal with the reference signature using probabilistic matching to determine the volume of liquid remaining in the dose container.

In some embodiments, a method for determining a dose delivered by an injection pen using the drug measurement system includes causing a light source and/or light guide to emit/distribute electromagnetic radiation toward the injection pen a first time and detecting a first signature of the emitted/distributed electromagnetic radiation through the injection pen with a plurality of sensors. The first signature is then compared to a plurality of reference signatures to determine the first volume of liquid in the injection pen. The method further includes causing the light source and/or light guide to emit/distribute electromagnetic radiation toward the injection pen a second time, after the first time, and detecting a second signature of the emitted/distributed electromagnetic radiation through the injection pen with the plurality of sensors. The second signature is then compared to the plurality of reference signatures to determine the second volume of liquid in the injection pen. The second volume may be deducted from the first volume to determine a dose delivered from the injection pen.

In some embodiments, the light source and the plurality of sensors are disposed in an injection pen cap. In some embodiments, the method includes detecting the first signature prior to the injection pen cap being removed from the injection pen and detecting the second signature after the injection pen cap has been placed back on the injection pen. The method also may include communicating the dose delivered information to an external device. In some embodiments, the method includes switching the pen cap to a power save mode after a predetermined period of inactivity of the pen cap and/or based on available power (e.g., battery level). In some embodiments, the method further includes alerting the user if a volume of liquid remaining in the drug container is critically low, if it is time to deliver a dose of medication, if available power drops below a predetermined level, if an unexpected or incorrect medication is being used, and/or if a medication is being delivered at an unexpected or incorrect time.

In some embodiments, a health management system includes a drug delivery device including a drug reservoir, and a dose measurement system configured to be removably coupleable to the drug delivery device. The dose measurement system includes a light source and/or light guide disposed and configured to emit/distribute electromagnetic radiation toward the drug reservoir a plurality of sensors optically coupleable to the light source disposed and configured to detect a quantity of electromagnetic radiation communicated through the drug reservoir. The quantity of electromagnetic radiation serves as a signature representative of the volume of liquid remaining in the drug reservoir. The health management system also includes a display configured to present information to a user indicative of the volume of liquid remaining in the drug reservoir. The dose measurement system may be configured to communicate data representative of the volume of liquid remaining in the drug reservoir to a remote device, for example, to allow the remote device to calculate a dose delivered to the patient. In some embodiments, the dose management system is configured to receive user health data from the remote device which may include, for example user blood glucose level, user diet, user exercise, and/or user home health monitored data.

In some embodiments, a light source includes a single light source (e.g., a single LED) paired with a light guide. The light source is disposed and configured to emit electromagnetic radiation into the light guide. The light guide is disposed and configured to receive the emitted electromagnetic radiation. The light guide may be a light pipe or light tube for transporting, redirecting, and/or otherwise distributing the received electromagnetic radiation toward the container.

In some embodiments, the light guide comprises a hollow structure with reflective and/or absorptive inner walls for controlling leakage of and/or containing at least some of the electromagnetic radiation (e.g., a prism light guide or a molded plastic light tube). The inner walls may be lined and/or treated with a reflective material and/or absorbing material, such as Laser Gold® reflective plating and/or Laser Black™ selectively absorbing coating (both available from Epner Technology, Inc. (Brooklyn, N.Y.)). A light guide may be designed to distribute electromagnetic radiation over its length by defining, for example, one or more openings or areas configured to allow at least some electromagnetic radiation to be transmitted out of the light guide. The openings or areas may be disposed for directing electromagnetic radiation toward different points along a container. The openings or areas function as a pseudo-plurality of light sources.

In some embodiments, a light guide comprises a transparent solid structure for controlling leakage of and/or containing at least some of the electromagnetic radiation by internal reflection (e.g., an optical fiber). A light guide may be designed to transmit at least some of the electromagnetic radiation toward different points along a container. The distribution of the transmitted electromagnetic radiation may be uniform or nearly uniform (e.g., using microscopic prisms) over the length of the light guide, thereby functioning as a pseudo-plurality of light sources.

The geometry and dimensions of a light guide may vary from other light guides or between components of the light guide itself. For example, a cross-section of at least a portion of a light guide may be round, square, hexagonal, etc. A light guide may not be straight, but instead, may have one or more bends and/or angles. In some embodiments, a light guide includes a dome or cupola for collecting and reflecting as much electromagnetic radiation as possible into the light guide. A light guide also may have directional collector devices, reflector devices, and/or lens devices (e.g., a Fresnel lens device) to assist in collecting additional directional electromagnetic radiation. In some embodiments, a light guide includes one or more diffusers to spread the light toward a container.

According to some embodiments, a plurality of sensors are optically coupleable to the light guide and are disposed and configured to detect the electromagnetic radiation distributed by at least a portion of the light guide (e.g., directed through at least one opening or area or distributed over some length of the light guide). A processing unit may be configured to receive data representing the portion of the detected electromagnetic radiation from each of the plurality of sensors and to convert the received data into a signature representative of the electromagnetic radiation detected by the plurality of sensors.

As used in this specification, the terms "about" and "approximately" generally include plus or minus 10% of the value stated. For example, about 5 would include 4.5 to 5.5, approximately 10 would include 9 to 11, and about 100 would include 90 to 110.

FIG. 1 is a schematic block diagram of a dose measurement system 100 for measuring the dose in a drug delivery device 110. The dose measurement system 100 includes a lighting module 140, a sensing module 150, a processing unit 160 and a communications module 170. The dose measurement system 100 may be configured to be removably coupleable to the drug delivery device 110 that is used to deliver a drug dose to a target T such as, for example, a human patient.

The drug delivery device 110 may be any drug delivery device 110 that can be used for injecting a medication into a patient. For example, the drug delivery device 110 may be an injection device or pen (e.g., insulin injection pen), a syringe, an infusion device or pump (e.g., insulin delivery pump), an ampoule, or a vial. The dose measurement system 100 may be configured to be coupleable to a wide variety of drug delivery devices 110, using, for example, different shapes, sizes, and drug volumes. In some embodiments, the dose measurement system 100 is configured to receive a portion of the drug delivery device 110 (e.g., a portion that defines an internal volume containing the drug, an injector, and/or plunger). In some embodiments, the dose measurement system 100 is configured to be removable from the drug delivery device 110 when the user is delivering a dose to the target T. In some embodiments, the dose measurement system 110 can remain attached to the drug delivery device 110 when the user is delivering a dose to the target T. In some embodiments, the dose measurement system 100 is configured to be reusable. In some embodiments, the dose measurement system 110 is permanently coupled to the drug delivery device 110, for example, integrated into the body of the drug delivery device. In such embodiments, the dose measurement system 100 may be disposable.

The lighting module 140 may include a light source and/or light guide configured to emit/distribute electromagnetic radiation toward the drug delivery device 110. In some embodiments, the light source and/or light guide is configured to emit/distribute electromagnetic radiation toward a drug reservoir (not shown) of the drug delivery device 110. In some embodiments, the light source is a light emitting diode (LED). In some embodiments, the light source is configured to emit infrared radiation or microwave radiation, such that the electromagnetic radiation can penetrate through a housing and/or any internal components of the drug delivery device 110, and/or the liquid drug contained therein. In some embodiments, the light source is configured to emit continuous electromagnetic radiation for a predefined time period. In some embodiments, the light source is configured to emit pulses of electromagnetic radiation (e.g., a series of less than 100 microsecond pulses or pulses about 200 microseconds apart plus or minus 100 microseconds).

The lighting module 140 may include a light source and a light guide. The light source may be configured to emit electromagnetic radiation toward and into the light guide. The light guide may be configured to receive and reflect the electromagnetic radiation emitted by the light source toward the drug delivery device 110. In some embodiments, the light guide is configured to output electromagnetic radiation toward a drug reservoir (not shown) of the drug delivery device 110. In some embodiments, the light source is a single LED. In some embodiments, the light source is configured to emit infrared radiation or microwave radiation, such that the electromagnetic radiation can travel through the light guide and penetrate through a housing and any internal components of the drug delivery device 110, and/or the liquid drug contained therein. In some embodiments, the light source is configured to emit continuous electromagnetic radiation for a predefined time period. In some embodiments, the light source is configured to emit pulses of electromagnetic radiation (e.g., a series of less than 100 microsecond pulses or pulses about 200 microseconds apart plus or minus 100 microseconds).

The sensing module 150 includes a plurality of sensors that are optically coupleable to the light source, the light guide, or a combination thereof. In some embodiments, each of the plurality of sensors may be a photodetector. The plurality of sensors are disposed and configured to detect at least a portion of the electromagnetic radiation emitted/distributed by the light source and/or the light guide. In some embodiments, the detected electromagnetic radiation includes transmitted, refracted, and/or reflected portions of the electromagnetic radiation. In some embodiments, the refracted electromagnetic radiation includes multi-directional refraction caused by a lensing effect of a curved surface of the housing of the drug delivery device 110 and/or the drug reservoir.

The processing unit 160 is configured to receive the electromagnetic radiation signal from the sensing module 150 (i.e., each of the plurality of sensors) and convert the received data into a signal signature representative of the electromagnetic radiation detected by each of the plurality of sensors. The processing unit 160 may include a processor, such as a microcontroller, a microprocessor, an ASIC chip, an ARM chip, an analog to digital convertor (ADC), and/or a programmable logic controller (PLC). In some embodiments, the processing unit 160 includes a memory that is configured to temporarily store at least one of the electromagnetic radiation data detected by each of the plurality of sensors and the signal signature produced from it. In some embodiments, the memory also is configured to store a plurality of reference signatures. Each of the plurality of reference signatures may be representative of a drug volume in the drug delivery device 110. In some embodiments, the processing unit 160 also includes an RFID chip configured to store information (e.g., remaining volume or dose information) and to allow a near field communication (NFC) device to read the stored information. In some embodiments, the processing unit 160 is configured to associate the signal signature with the reference signature to determine a volume or number of doses remaining in and/or injected by the drug delivery device 110. In some embodiments, the processing unit 160 can also be configured to determine the type of drug delivery device 110 coupled to the dose measurement system 100, and/or the drug contained in the drug delivery device 110. In some embodiments, the processing unit 160 also includes a global positioning system (GPS) to, for example, determine a current location of the dose measurement system 100.

The communications module 170 may be configured to allow two-way communication with an external device (e.g., a smart phone, a local computer, and/or a remote server). In some embodiments, the communications module 170 includes a communication interface to provide wired communication with the external device (via, e.g., a USB or firewire interface). In some embodiments, the communication interface also is used to recharge a power source (not shown), such as a rechargeable battery. In some embodiments, the communications module 170 includes means for wireless communication with the external device (e.g., Wi-Fi, Bluetooth® wireless technology, Bluetooth® low energy technology, Zigbee and the like).

In some embodiments, the communications module 170 includes a display configured to communicate a status of the dose measurement system 100 to the user, including but not limited to a volume or number of doses remaining, history of use, remaining battery life, wireless connectivity status, and/or user reminders. In some embodiments, the status also includes information on whether an injector, for example, a needle, is attached/detached to the drug delivery device 110. Generally a user is required to attach a new injector (e.g., needle) to the drug delivery device 110 prior to each drug injection. Status information on the injector attachment/detachment can therefore inform the user and/or an external monitor (e.g., a doctor) whether the user is replacing the injector after each injection.

In some embodiments, the communications module 170 also includes microphones and/or vibration mechanisms to convey audio and tactile alerts. In some embodiments, the communications module 170 includes a user input interface (e.g., a button, a switch, an alphanumeric keypad, and/or a touch screen) to allow a user to, for example, input information into the dose measurement system 100, power ON the system, power OFF the system, reset the system, manually input details of a patient behavior, manually input details of drug delivery device 110 usage, and/or manually initiate communication between the dose measurement system 100 and a remote device.

The dose measurement system 100 may be disposed in a housing (not shown) that can be configured to be removably coupleable to the drug delivery device 110. For example, the lighting module 140, sensing module 150, processing unit 160, and/or the communications module 170 may be incorporated into a housing. One or more individual components of the dose measurement system 100 (e.g., the lighting module 140 and the sensing module 150) may be incorporated into a first housing while one or more other components (e.g., the processing unit 160 and communications module 170) may be separate and/or incorporated into a second housing. In some embodiments, the housing is configured (e.g., shaped and sized) to be removably coupled to at least a portion of the drug delivery device 110. For example, the housing may have a recess and/or define a bore into which a portion of the drug delivery device 110 can be received. The housing may have alignment features to allow the dose measurement system 100 to be coupled to the drug delivery device 110 in a predetermined radial orientation. The housing may be opaque and include an insulation structure to prevent interference from ambient electromagnetic radiation (e.g., to increase signal quality). For example, the insulation structure may be a metal lining configured to shield the electronic components of the dose measurement system 100 from external electromagnetic radiation. In some embodiments, the housing can substantially resemble a cap to act as a replacement cap for the drug delivery device 110 (e.g., a pen cap for an injection pen). In some embodiments, the insulating structure may include plastic mixed with a metallic compound (e.g., titanium dioxide) to modify a property of the insulation structure. For example, the addition of certain metallic compound can modify the light transmissivity of the housing (e.g., to make it more opaque). In some embodiments, the addition of titanium dioxide to plastic can be used to modify the coloring (e.g., improve the whiteness) of the housing. In some embodiments, an average of 3%-5% by volume of titanium dioxide can be added to thermosetting and thermoplastic materials (e.g., polyolefins, polystyrene, ABS, polyvinyl chloride, a combination thereof, and/or the like) to form the insulating structure. In some embodiments, the insulating structure can shield the electronic components of the dose measurement system 100 from external electromagnetic radiation. In some embodiments, the opaque nature of the insulating structure due to addition of an opacifier such as titanium dioxide, may prevent external infrared radiation from entering the housing. In this manner, the insulating structure may shield the electronic components of the dose measurement system 100 from external electromagnetic radiation. In some embodiments, the insulating structure may prevent the infrared radiation emitted by the lighting module 140 from passing through the walls of the housing and/or the pen cap. That is, electromagnetic radiation emitted by the lighting module 140 can be prevented from leaving the housing and/or the pen cap. This prevents electromagnetic radiation emitted by the lighting module 140 from leaving the housing, bouncing back off an external object (e.g., table, chair, cell phone, etc.) and then returning back into the housing and/or pen cap. In this manner, in addition to canceling ambient light the insulating structure may correct electromagnetic and/or infrared radiation that may be reflected back into the housing and/or pen cap.

In some embodiments, the lighting module 140 and the sensing module 150 are disposed and oriented in the housing of the dose measurement system 100, such that the light source and/or the light guide is disposed on a first side, and the plurality of sensors are disposed on a second side of the drug delivery device 110. In some embodiments, the light source and/or the light guide is disposed at a first radial position with respect to the drug delivery device 110, and the plurality of sensors are disposed at a second radial position which is different than the first radial position (e.g., the second radial position is approximately 180 degrees from the first radial position). In other words, the dose management system 100 may be arranged so that the light source and/or the light guide is disposed on one side of a drug reservoir, and the plurality of sensors are disposed on the opposite side of the drug reservoir. In some embodiments, the plurality of sensors are disposed in a substantially straight line. In some embodiments, the plurality of sensors are disposed in a substantially straight line that is substantially parallel to the elongate axis of the light guide. In some embodiments, the light guide is disposed such that the distribution of electromagnetic radiation is parallel to and in line of sight of at least one sensor. In other embodiments, the light guide is disposed such that each opening or area for transmitting electromagnetic radiation is located adjacent to at least one sensor, each opening or area also being located parallel to and in line of sight of at least one sensor. In some embodiments, at least one of the light guide distribution, openings, or areas and/or at least one of the plurality of sensors is located in an inclined orientation with respect to a longitudinal axis of the drug delivery device 110. In some embodiments, the number of the plurality of sensors is equal to, greater than, or less than a number of light guide openings or areas for transmitting electromagnetic radiation. In some embodiments, the light guide can be disposed along a light guide axis on a second side of the drug reservoir such that the light guide axis is substantially parallel to the longitudinal axis of the dose measurement system 100. In some embodiments, the plurality of sensors can be disposed along a sensor axis on a first side of the drug reservoir such that the sensor axis is substantially parallel to the longitudinal axis of the dose measurement system 100. In some embodiments, the light source can be disposed and configured to emit electromagnetic radiation along the light guide axis. In some embodiment, the light source can be angled downwards and is not facing the first side of the drug reservoir. That is, the light source is angled in such a manner that the light source is approximately perpendicular to the plurality of sensors. In some embodiments, the dose measurement system 100 can include at least one opening or area on the second side of the drug reservoir to distribute at least a portion of the electromagnetic radiation emitted by the light source. In some embodiments, the dose measurement system 100 can include a light guide on the second side of the drug reservoir to distribute at least a portion of the electromagnetic radiation emitted by the light source. In some embodiments, the light guide is disposed such that the elongated axis of the light guide is substantially parallel to the plurality of sensors. Scattered portions of the electromagnetic radiation emitted from the light guide may be detected by the plurality of sensors.

In some embodiments, the light source and/or the light guide and the plurality of sensors are configured such that the dose measurement system 110 can detect the volume of drug in the drug delivery device 110 with a resolution of 1 unit of drug or smaller (e.g., fractions of units of drug such as 0.1 units, 0.2 units, 0.5 unites, etc.). In some embodiments, the light source and/or light guide and the plurality of sensors are configured such that the dose measurement system 110 can detect the position of a plunger portion of an actuator disposed in the drug delivery device 110 with a resolution of about 10 micrometers, about 20 micrometers, about 30 micrometers, about 40 micrometers, about 50 micrometers, about 60 micrometers, about 70 micrometers, about 80 micrometers, about 90 micrometers, about 100 micrometers, about 110 micrometers, about 120 micrometers, about 130 micrometers, about 140 micrometers, about 150 micrometers, about 160 micrometers, about 170 micrometers, about 180 micrometers, or about 200 micrometers, inclusive of all ranges therebetween.

Having described above various general principles, several exemplary embodiments of these concepts are now described. These embodiments are only examples, and many other configurations of a dose measurement system, systems and/or methods for measuring dose delivered by a drug delivery device and overall health of a patient are envisioned.

Figure 2:
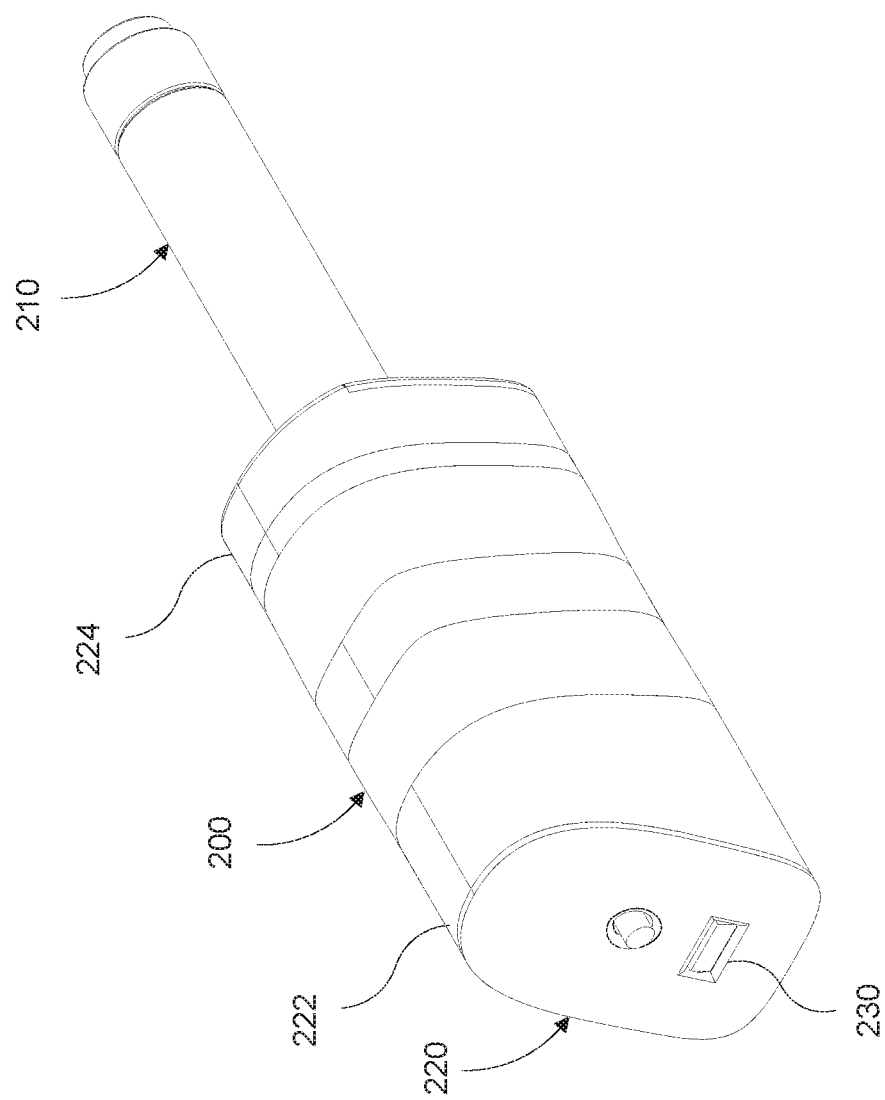
FIG. 2 is a perspective view of a dose measurement system in accordance with some embodiments.
Figure 3:
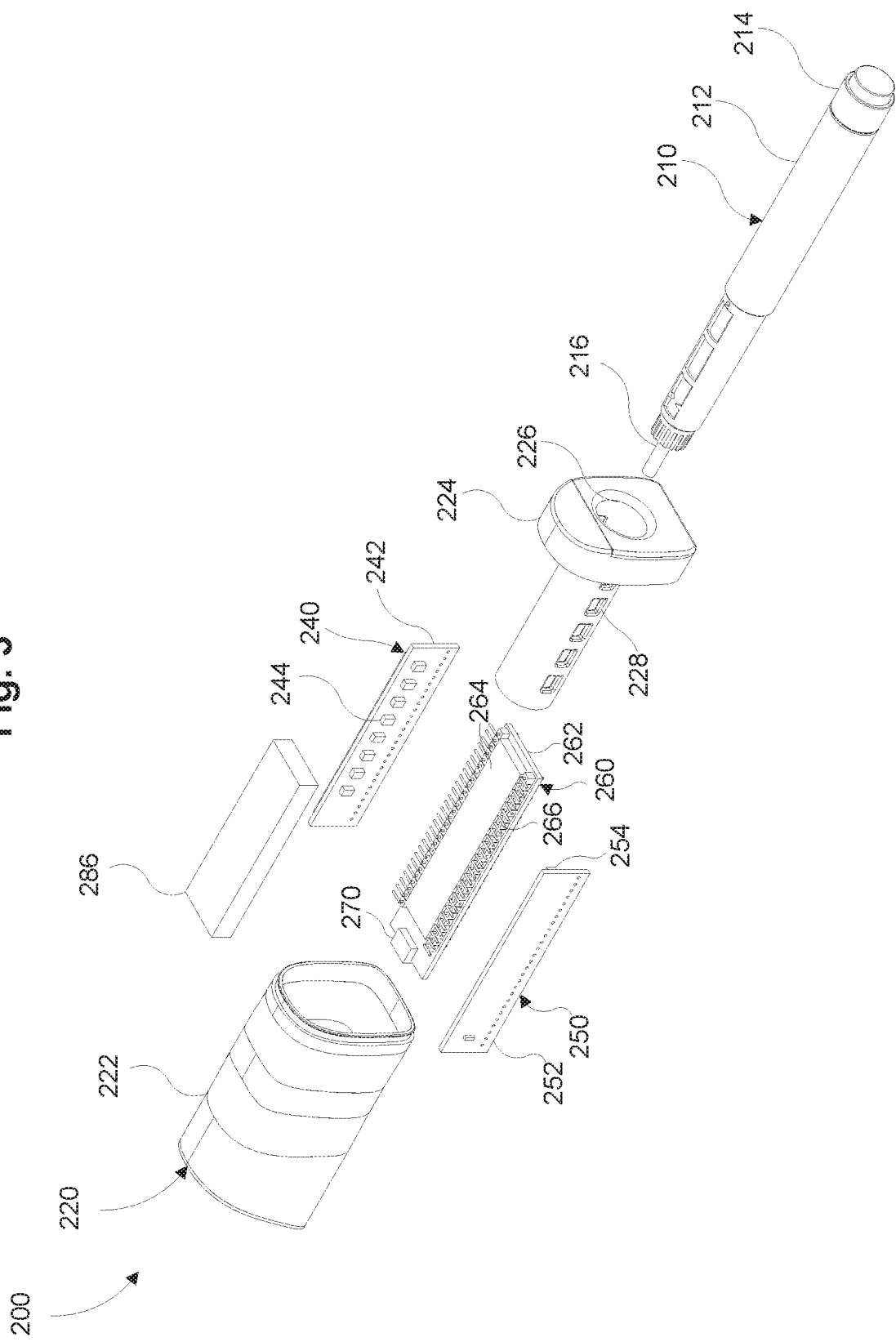
FIG. 3 is an exploded perspective view of the dose measurement system of FIG. 2 in accordance with some embodiments.
Figure 4:
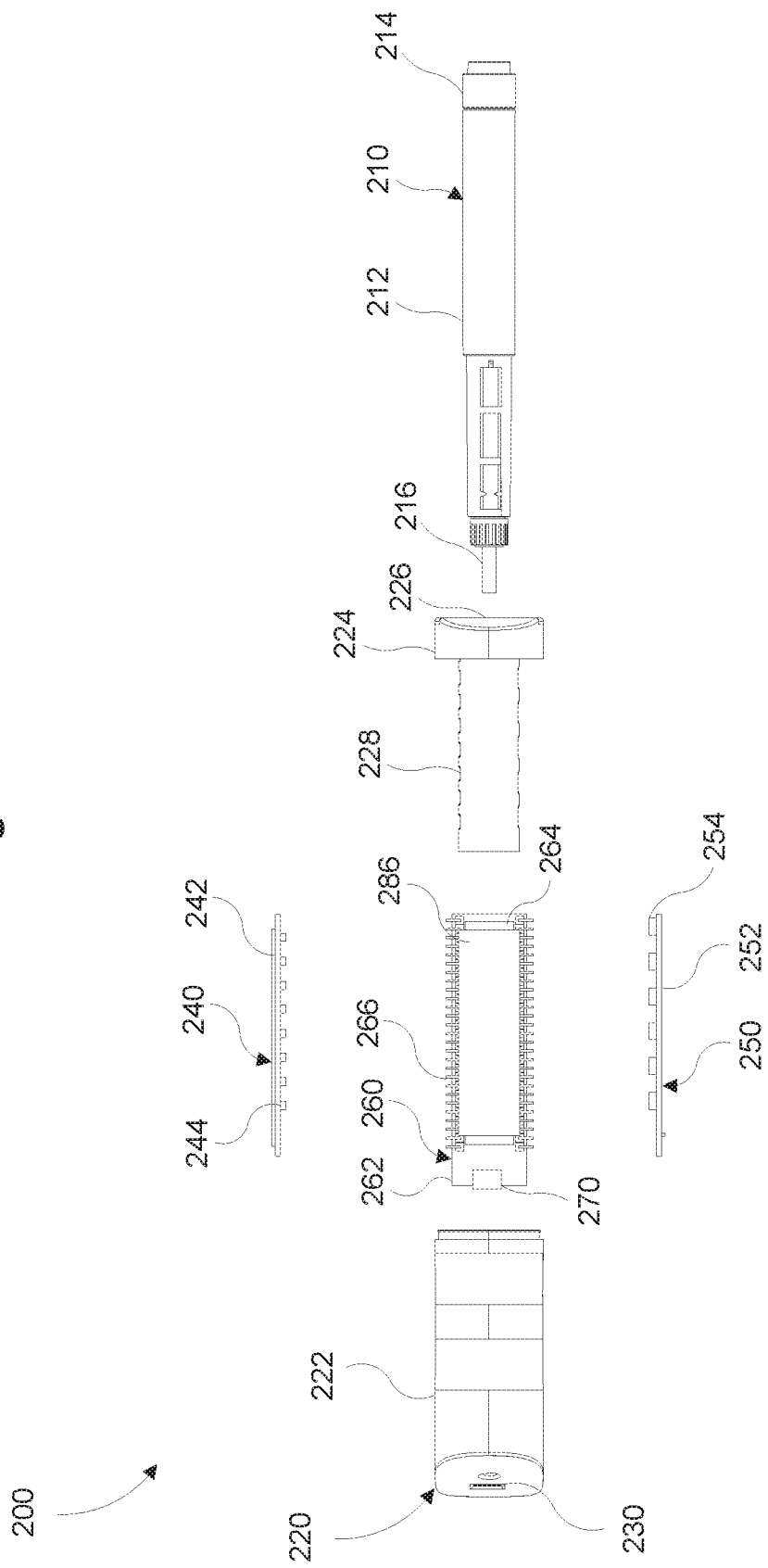
FIG. 4 is an exploded top view of the dose measurement system of FIG. 2 in accordance with some embodiments.

Referring now to FIGS. 2-4 a dose measurement system 200 may include a lighting module 240, a sensing module 250, a processing unit 260, a communications module 270, and a power source 286. The dose measurement system 200 may be configured to be removably coupleable to a drug delivery device 210 (also referred to herein as "an injection pen 210"). The drug delivery device 210 may be configured to deliver a predefined quantity of a drug (e.g., a dose) to a patient. Examples of the drug delivery device 210 include insulin injection pens that can be used by a patient to self-administer insulin. As described herein, the drug delivery device 210 may include a housing 212, an actuator 214, and an injector 216. The housing 212 may be relatively opaque, such that it only allows select wavelengths of electromagnetic radiation to be transmitted therethrough (e.g., infrared or microwave radiation). The housing 210 defines an internal volume (e.g., a reservoir) for storing a drug. The actuator 214 may include a plunger portion in fluid communication with the drug and configured to communicate a predefined quantity of drug to the patient. The actuator 214 may be configurable (e.g., by the user) to dispense variable quantities of the drug. The injector 216 may be configured to penetrate a user's skin for intramuscular, subcutaneous, and/or intravenous delivery of the drug.

The dose measurement system 200 includes a housing 220 that includes a top housing portion 222 (also referred to herein as "top housing 222") and a bottom housing portion 224 (also referred to herein as "bottom housing 224"). The top housing portion 222 and the bottom housing portion 224 may be removably or fixedly coupled together by, for example, gluing, hot welding, a snap-fit mechanism, screws, or by any other suitable coupling means. The housing 220 may be made from a rigid, light weight, and opaque material including, but not limited to, polytetrafluoroethylene, high density polyethylene, polycarbonate, other plastics, acrylic, sheet metal, any other suitable material, or a combination thereof. The housing 220 may be configured to shield the internal electronic components of the dose measurement system 200 from environmental electromagnetic noise. For example, the housing may include an insulation structure (not shown) such as, for example, aluminum lining or any other metal sheet or foil that can serve as an electromagnetic shield.

As shown in FIG. 3, the top housing portion 222 defines an internal volume for substantially housing the lighting module 240, the sensing module 250, the processing unit 260, the communications module 270, and the power source 286. The bottom housing portion 224 defines a bore 226, shaped and sized to receive at least a portion of the drug delivery device 210. For example, the bore 226 may be shaped and sized to receive only the drug containing portion of the housing 212 and the injector 216. The bore 226 may be configured to receive the drug delivery device 210 in a preferred orientation (e.g., a preferred radial orientation). In some embodiments, the bore 226 is in close tolerance with the diameter of the drug delivery device 210, for example, to form a friction fit with the drug delivery device 210. In some embodiments, the bore 226 includes one or more notches, grooves, detents, any other snap-fit mechanism, and/or threads, for removably coupling the drug delivery device 210 to the bottom housing 224. In some embodiments, bottom housing portion 224 includes one or more alignment features to allow the drug delivery device 210 to be coupleable with the dose measurement system 200 in a predetermined radial orientation.

In some embodiments, the bottom housing 224 includes one or more apertures 228 for receiving at least a portion of the light source and/or light guide 244 of the lighting module 240, and/or sensors 254 of the sensing module 250. The apertures 228 may be configured to provide mechanical support for the light source and/or light guide 244 and/or sensors 254, or can serve as an alignment mechanism for the lighting module 240 and/or sensing module 250.

As shown in FIG. 4, the top housing 222 includes an opening 230 for receiving at least a portion of the communications module 270 such as, for example, a communication interface to provide wired communication with an external device, and/or an interface for charging the power source 286. In some embodiments, the top housing 222 also includes features (e.g., recesses, apertures, cavities, etc.) for receiving a portion of the drug delivery device 210 such as the injector 216. In some embodiments, the housing 220 also includes a detection mechanism (not shown) to detect if the drug delivery device 210 has been coupled to the dose measurement system 200 (e.g., a push switch, a motion sensor, a position sensor, an optical sensor, a piezoelectric sensor, an impedance sensor, or any other suitable sensor). The housing 220 may be relatively smooth and free of sharp edges. In some embodiments, the housing 220 is shaped to resemble a pen cap that has a form factor that occupies minimal space (e.g., fits in the pocket of a user). In some embodiments, the housing 220 also includes features for handling (e.g., clips for attaching to a user's shirt pocket) and/or various ornamental features. In some embodiment, the dose measurement system 200 also serves as a replacement cap for the drug delivery device 210. In some embodiments, the housing 220 also includes one or more sensors (e.g., optical sensors) to determine a status of the drug delivery device 210, for example, if the injector 216 (e.g., a needle) is attached/detached to the drug delivery device 210.

Referring still to FIGS. 3 and 4, the light source and/or light guide 244 (e.g., an LED) of the lighting module 240 is mounted on, or otherwise disposed on, a printed circuit board (PCB) 242. The PCB 242 may be any standard PCB made by any commonly known process. In some embodiments, the light source and/or light guide 244 is arranged to emit/distribute electromagnetic radiation along the length of the housing such that, when the portion of the drug delivery device 210 that defines the internal volume of the housing 212 holding the drug is coupled with the dose measurement system 200, the light source and/or light guide 244 can illuminate the entire internal volume. In some embodiments, the light source and/or light guide 244 is fabricated and oriented in another shape or configuration, such that the electromagnetic radiation is distributed unequally, alternately with the sensors 254, in a zig-zag pattern, or using any other configuration as described herein.

In some embodiments, the light sources and/or light guide 244 is configured to produce an electromagnetic radiation of a wavelength that is capable of penetrating through the housing 212 of the drug delivery device 210, the drug contained therein, and/or a portion of the housing 220. For example, infrared radiation or microwave radiation can penetrate many of the plastic materials that are commonly used in manufacturing drug delivery devices (e.g., injection pens). In some embodiments, an electromagnetic radiation has a frequency that also can penetrate through the internal components of the drug delivery device 210, such as the plunger portion of the actuator 214. In some embodiments, the light source and/or light guide is 244 configured to produce a wide beam of electromagnetic radiation (e.g., a wide-angled LED or a diffused exit opening of a light guide). Said another way, the electromagnetic radiation cone of a single light source and/or opening in a light guide 244 may have a wide angle, and the electromagnetic radiation cones of adjacent openings in a light guide 244 may overlap. In some embodiments, a light source and/or light guide 244 is configured to emit/distribute pulses of electromagnetic radiation (e.g., a series of less than 100 microsecond pulses or pulses about 200 microseconds apart plus or minus 100 microseconds).

The plurality of sensors 254 of the sensing module 250 may be mounted on, or otherwise disposed on, a PCB 252. The PCB 252 may be any standard PCB made by any commonly known process. The plurality of sensors 254 may be any optical sensors (e.g., photodiodes) optically coupleable with the light source and/or light guide 244 and configured to detect at least a portion of the electromagnetic radiation emitted/distributed by the light source and/or light guide 244. The electromagnetic radiation may be transmitted radiation, refracted radiation (e.g., refracted through air, drug, and/or body of drug delivery device 210), reflected radiation (e.g., reflected from a wall of the housing 220 or internally reflected from a wall of the drug delivery device 210), and/or multi-directional refraction/reflection caused by a lensing effect of a curved surface of the housing 212 and/or the drug reservoir. The transmitted, refracted, and/or reflected electromagnetic signal received by the plurality of sensors 254 may be used to create a signal signature (e.g., by the processing unit 260). The signal signature may then be associated with a reference signature to determine the volume or number of doses remaining in the drug delivery device 210. In some embodiments, the signal response of the sensors may be used to measure usability metrics such as, for example, determining the presence of the injector 216 of the drug delivery device 210, and/or determining whether the drug delivery device 210 is coupled or uncoupled to the dose measurement system 200. In some embodiments, the signal response of the sensors 254 also may be used to determine the type of a drug delivery device 210 is coupled to the dose measurement system 200, and/or the type of drug present in the drug delivery device 210.

In some embodiments, the sensors 254 are arranged in a substantially similar configuration to the light source and/or light guide 244. In some embodiments, the number of sensors 254 is the same as, greater than, or less than the number of pseudo-light sources created by the light source and light guide 244. In some embodiments, the light source and/or light guide 244 and/or sensors 254 are arranged in an inclined orientation.

The processing unit 260 may include a PCB 262 and a processor 264. The PCB 262 may be any standard PCB made by any commonly known process and may include amplifiers, transistors and/or any other electronic circuitry as necessary. The processor 264 may be any processor, including, but not limited to, a microprocessor, a microcontroller, a PLC, an ASIC chip, an ARM chip, an ADC, and/or any other suitable processor. The processing unit 260 may be coupled to the lighting module 240 and the sensing module 250 using electronic couplings 266, such that the lighting module 240 and the sensing module 250 are oriented perpendicular to the processing unit 260 and parallel to each other. In some embodiments, the processing unit 260 includes an onboard memory for at least temporarily storing a signal signature, a reference signature database, dose information, user health data (e.g., blood glucose level), device location data (e.g., from a GPS optionally included in the dose measurement system 200 or from another GPS enabled device that is paired with the system 200 such as a blood glucose meter or cellular phone), and/or any other data as might be useful for a patient to manage their health. In some embodiments, the processing unit 260 includes an RFID chip configured to store information and/or allow an NFC device to read the information stored therein. The processing unit 260 may be configurable to control the operation of the dose measurement system 200, for example, activation and timing of the light source and/or light guide 244, and/or reading and processing of electromagnetic radiation data from the sensors 254. For example, the processing unit 260 may be configured to compare electromagnetic radiation signal signature obtained from the plurality of sensors 254 and associate it with the reference signature database to determine the volume or quantity of doses remaining in the drug delivery device 210 or the position of the actuator 214 (e.g., plunger) of the drug delivery device 210.

In some embodiments, the processing unit 260 is configured to correct the signal signature for background noise. For example, the processing unit 260 may be configured to operate the sensing module 250 to detect a background signature with the lighting module in dark state, i.e., the light source 244 switched off. The background signature can then be associated with the signal signature to correct for background noise. In some embodiments, the processing unit 260 also includes electronic signal filtering algorithms, including, but not limited to, Fourier transforms, low pass filter, band filter, high pass filter, Bessel filter, and/or any other digital filter to reduce noise and increase signal quality. The processing unit also may be configured to obtain reference signatures by storing the electromagnetic radiation signal detected by the sensing module 250 for a range of dose volumes in a representative drug delivery device 210, including, but not limited to, electromagnetic radiation signal at drug delivery device 210 being full, being empty, and a series of intervals there between (e.g., every unit of dose dispensed from the drug delivery device and/or every 170 micrometer displacement of a plunger portion of the actuator 214 included in the drug delivery device 210).

In some embodiments, the processing unit 260 is configured to include probabilistic matching algorithms that can be used to associate the signal signature with the reference signature to determine a volume of liquid in the drug delivery device 210. In some embodiments, the processing unit 260 also includes algorithms to determine the type of drug delivery device 210 coupled to the dose measurement system 200 and/or the drug contained within the drug delivery device 210, from the signal signature. For example, drug delivery devices 210 of the same form factor (i.e., size and shape) can include different drugs, for example, insulin, epinephrine, or any other drug. In order to avoid confusion, delivery device 210 manufacturers often provide marking, labeling, and/or color coding to distinguish between different drugs in delivery devices 210 that look similar. Said another way, once a drug delivery device 210 company has designed and is manufacturing a particular delivery device 210, they often use that same design for different drug therapies. Therefore, in some embodiments, the algorithms included in the processing unit 260 are configured to determine the type of drug delivery device 210 coupled to the dose measurement system 200 based on, for example, material properties (e.g., color, refractive index, etc.) of the device. For example, different materials and/or colors can have different refractive indexes, which may be used for identification. In some embodiments, the type of drug included in the drug delivery device 210 also may be used to determine the type of delivery device 210 based on the refractive index of the drug.

The processing unit 260 also may be configured to control and operate the communications module 270. In some embodiments, the processing unit 260 is configured to operate the system in a power efficient manner. For example, the processing unit 260 may turn off the electronics powering the light source 244 (e.g., operational amplifiers) when they are not needed. The processing unit 260 may pulse the LEDs for a short period at high current to, for example, save power and/or increase signal to noise ratio. The processing unit 260 also may be configured to periodically activate the communications module 270 (e.g., about 1-10 times per day) and/or when the dose measurement system 200 is attached to the drug delivery device 210. Similarly, the processing unit 260 may turn the communications module 270 off when it is not needed. In some embodiments, the processing unit 260 also includes a global positioning system (GPS) to, for example, determine a current location of the dose measurement system 200.

The communications module 270 may be configured to communicate data to the user and/or an external device, for example, a smart phone application, a local computer, and/or a remote server. The communicated data may include, but is not limited to, initial system activation, system ON/OFF, drug delivery device 210 coupled/uncoupled, injector attached/detached from drug delivery device 210, volume remaining, number of doses remaining, dose history, time, system or drug temperature, system location (GPS), drug delivery device 210 coupling/uncoupling data, drug expiration date, velocity at which drug is delivered, device collisions, device power remaining, step count, tampering with the system, any other user health information, and/or any other usable data. In some embodiments, the communications module 270 is configured to receive data, for example, new calibration data, firmware updates, user health information (e.g., blood glucose levels, diet, exercise, dose information) and/or any other information input by the user, or communicated by an external device. The communications module 270 may include conventional electronics for data communication and can use a standard communication protocol, including, but not limited to, Wi-Fi, Bluetooth® wireless technology, Bluetooth® low energy technology, Zigbee, USB, firewire, and/or near field communication (e.g., infrared). In some embodiments, the communications module 270 is configured to periodically connect (e.g., about 1-10 times per day) to the external device (e.g., a smart phone) to log any dose data stored in the onboard memory. In some embodiments, the communications module 270 is activated on demand by the user.

Figure 5:
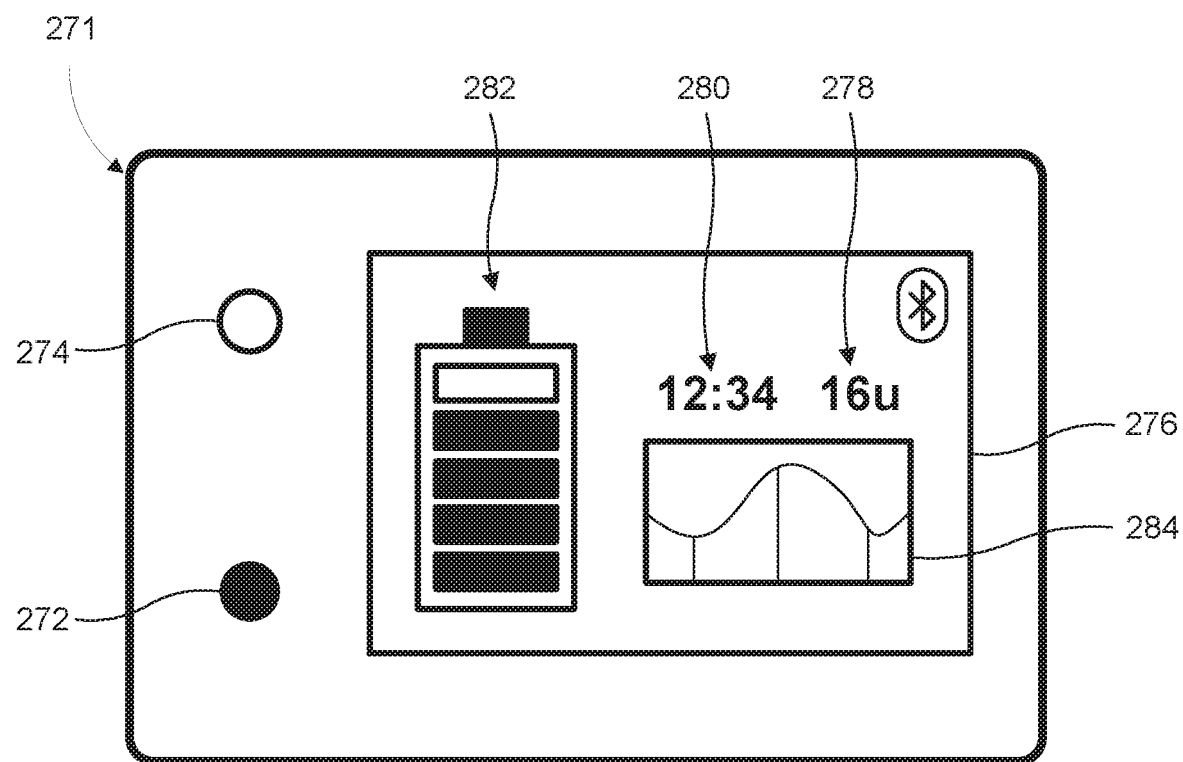
FIG. 5 is a schematic illustration of a communications interface, which may be included in the dose measurement system of FIG. 2 in accordance with some embodiments.

Referring now also to FIG. 5, in some embodiments, the communications module 270 includes a communication interface 271 located on an external surface of the housing 210 of the dose measurement system 200 for communicating with the user. The communication interface 271 may include a switch 272 (e.g., a power switch, a reset button, and/or a communication switch) to manually initiate communication with an external device (to activate, e.g., Bluetooth® wireless technology). In some embodiments, the communications interface 271 also includes an indicator 274 such as a light source (e.g., an LED) to indicate to the user, for example, if the dose measurement system 200 is ON/OFF, or the communication module 270 is active. In some embodiments, the communication interface 271 includes a display 276 for visual communication of information to the user, including, but not limited to, the volume or number of doses remaining 278 in the drug delivery device 210, the current time 280, system power remaining 282, dose history 284 (e.g., average dose usage, time last dose taken, etc.), an indication of charging status of the drug delivery device 210 (e.g., currently charging, fully charged, etc.), and/or wireless connectivity status. In some embodiments, the communications interface 271 includes an alphanumeric keypad, and/or a touch screen to, for example, allow a user to input information (e.g., food intake, exercise data, etc.) into the dose measurement system 200. In some embodiments, the communications module 270 includes a speaker for providing audible alerts or messages to the user (e.g., dose reminders and reinforcement messages) and/or a microphone for receiving audio input from the user. In some embodiments, the communications module 270 includes means for tactile alerts (e.g., a vibration mechanism). In some embodiments, the communications module 270 can communicate other information pertaining to user health, including, but not limited to, steps taken, calories burned, blood glucose levels, and/or any other information.

The power source 286 may be any power source that can be used to power the dose measurement system 200. In some embodiments, the power source 286 includes an energy storage device (e.g., a disposable battery). In some embodiments, the power source 286 includes a rechargeable battery, including, but not limited to, a NiCad battery, a Li-ion battery, Li-polymer battery, or any other battery that has a small form factor (e.g., of the type used in cell phones), and/or does not to be charged frequently (e.g., charged once per month). In some embodiments, the power source 286 is charged using an external power source, including, but not limited to, though a power socket located on the housing 220 and/or through a communication interface of the communications module 270 (e.g., a USB interface). In some embodiments, the power source 286 is charged using solar energy and may include solar panels. In some embodiments, the power source 286 is charged using kinetic energy and may include mechanical energy transducers.

Figure 6:
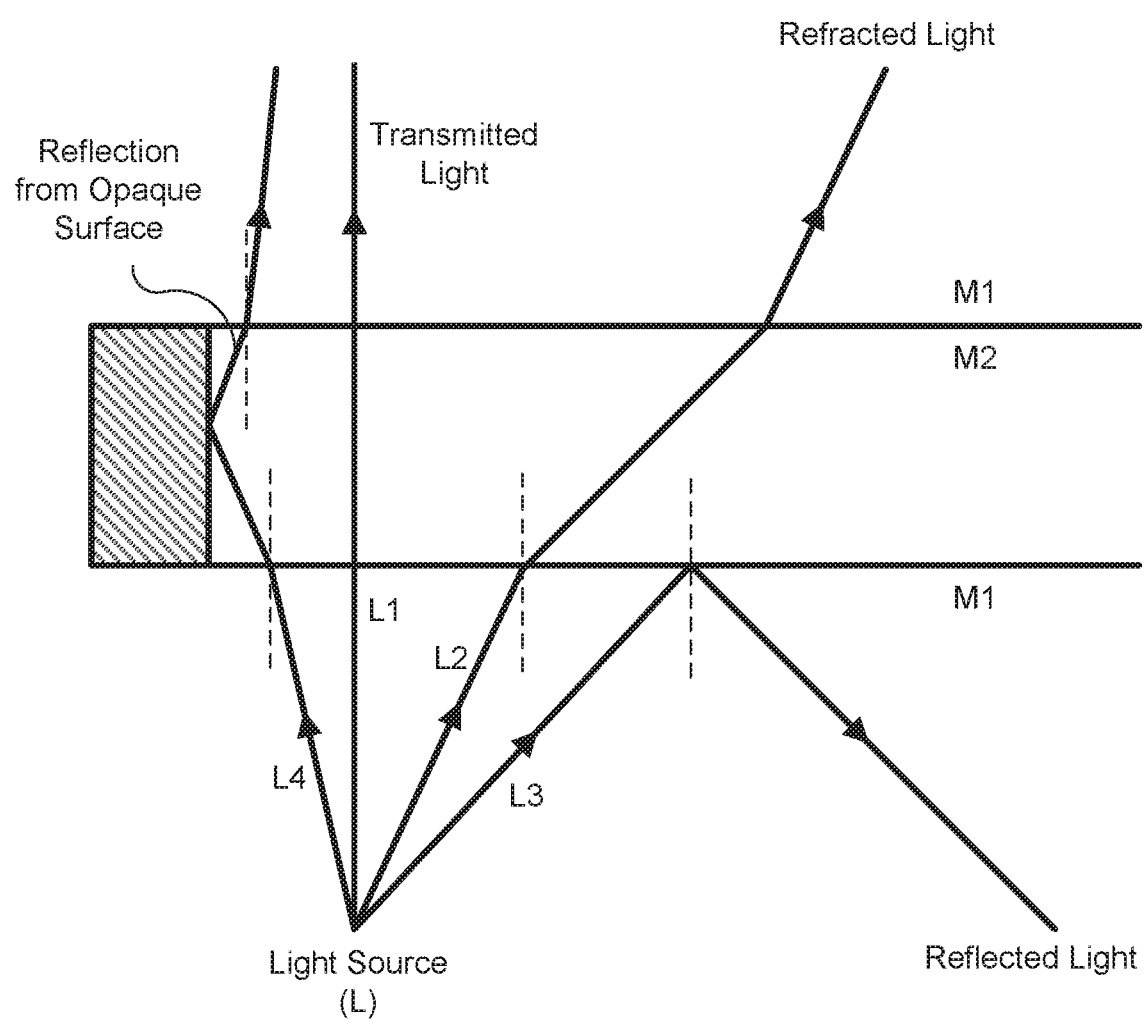
FIG. 6 is a schematic ray diagram of different modes of light transmission between a first medium and a second medium in accordance with some embodiments.

As described above, the plurality of sensors 254 of the sensing module 250 are configured to receive at least one of a transmitted radiation, refracted radiation (e.g., refracted through air, the liquid drug, the housing 212 of drug delivery device 210), reflected radiation (e.g., reflected from a wall of the housing 220 or internally reflected from a wall of the internal volume of the drug delivery device 210), and multi-directional reflection/refraction (e.g., caused by a lensing effect of a curved surface of the housing 212 of the drug delivery device 210). Referring now to FIG. 6, a light source L (e.g., a wide angle light source) can produce a plurality of light rays emanating and diverging away from the light source. The light source L is present in a first medium M1 (e.g., air) having a first refractive index n1. A second medium M2 (e.g., liquid drug) having a second refractive index n2, greater than the first refractive index (i.e., n2>n1), is bordered by the first medium M1 on both sides. The second medium M2 also may include an opaque surface (e.g., a sidewall).

A first light ray L1 emitted by the light source L is incident on the interface of the first medium M1 and the second medium M2 at a first angle of 0 degrees. This light ray does not bend as it penetrates through the second medium M2 and transmits back into the first medium M1 (the transmitted light) at the original angle of incidence. A second light ray L2 is incident on the interface of the first medium M1 and the second medium M2 at a second angle>0. The second light ray L2 bends or refracts (the refracted light) as it penetrates the second medium M2, and then bends again to its original angle of incidence as it reenters the first medium M1, parallel to but offset from the emitted ray L2. A third light ray L3 is incident on the interface of the first medium M1 and the second medium M2 at a third angle greater than the second angle. At this angle of incidence, the light ray L3 does not penetrate into the second medium M2, but it is reflected back into the first medium M1 (the reflected light), such that angle of reflection is equal to the angle of incidence. A fourth light ray L4 is incident on the interface of the first medium M1 and the second medium M2 at a fourth angle less than the third angle, such that the light ray L4 refracts in the second medium M2, but is now incident on the opaque surface included in the second medium M2 (reflection from opaque surface). At least a portion of the light ray L4 is reflected back into the second medium M2, which then reenters back into the first medium M1 at a fifth angle, such that the fifth angle is not equal to the fourth angle.

As described herein, the electromagnetic radiation signal received by the plurality of sensors 254 of the sensing module 250 may include a combination of the transmitted, refracted and reflected portions of the electromagnetic radiation. A unique signal signature is produced by the combination of the portions of the electromagnetic radiation at different dose volumes remaining, and/or the actuator 216 position of the drug delivery device 210. This signal signature may be compared with a reference signal signature database (also referred to herein as "a calibration curve") to obtain the volume or number of doses remaining in drug delivery device 210, as described in further detail herein.

Figure 7:
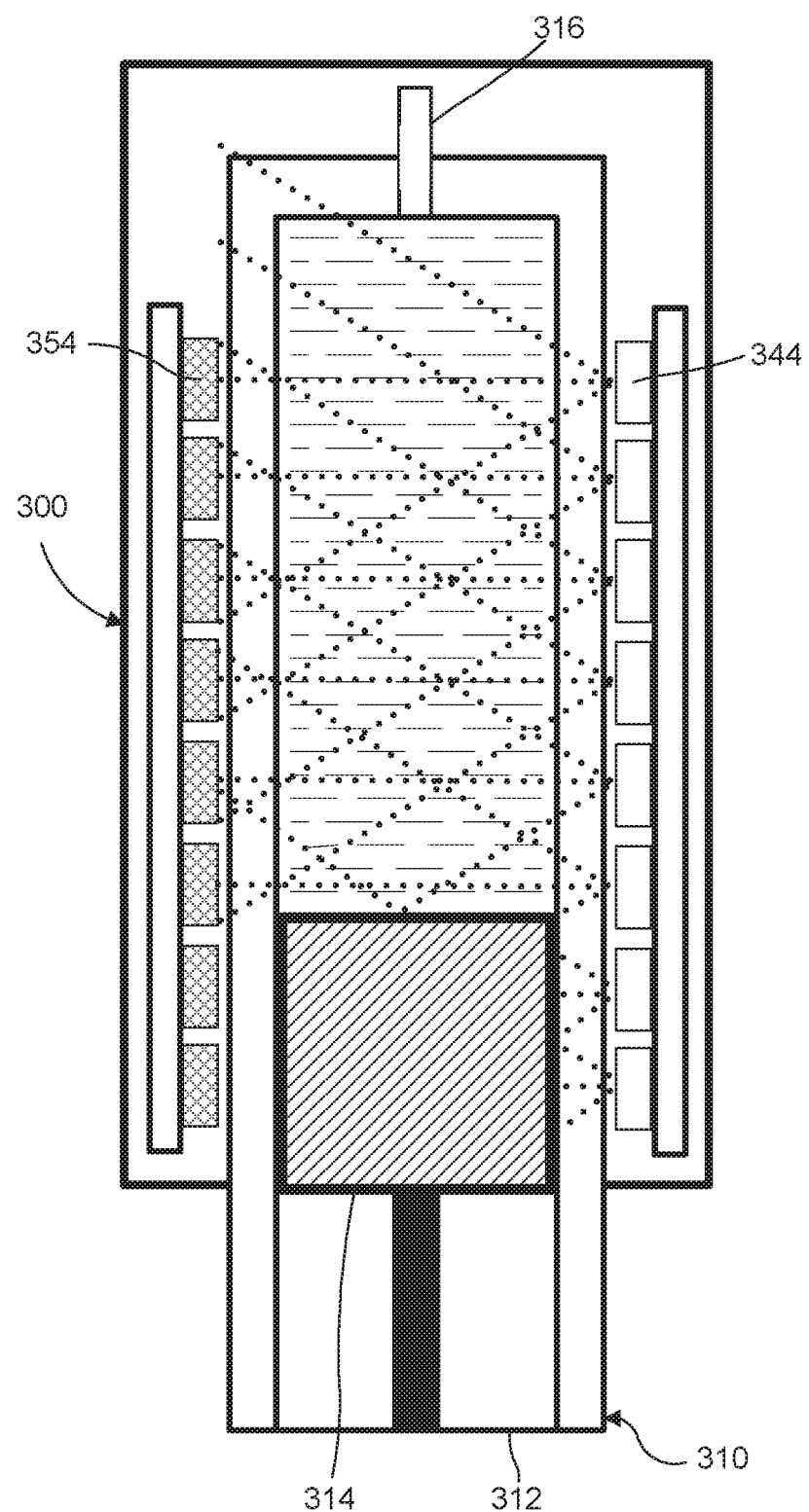
FIG. 7 is a cross-sectional view of a dose measurement system in accordance with some embodiments.

Referring now to FIGS. 7-10, various configurations of the light source and/or light guide and the sensors are shown and described. While the transmitted and reflected portion of the electromagnetic radiation is shown, the refractive portion is not shown for clarity. As shown in FIG. 7, a dose measurement system 300 includes a plurality or pseudo-plurality (using a light guide) of light sources 344 and a plurality of sensors 354. A drug delivery device 310 is coupled to the dose measurement system 300. The drug delivery device 310 includes a housing 312 and an actuator 314 that collectively define an internal volume (e.g., a reservoir) for containing a drug. The drug delivery device 310 also includes an injector 316 for communicating the drug to a patient. The dose measurement system 300 is configured such that the plurality or pseudo-plurality of light sources 344 are disposed on a first side of the housing oriented toward the drug delivery device 310 and the plurality of sensors 354 are disposed on a second side of the housing such that each of the plurality of sensors 354 is substantially opposite to, and in optical communication with, at least one of the plurality or pseudo-plurality of light sources 344. In some embodiments, the plurality or pseudo-plurality of light sources 344 and/or the plurality of sensors 354 are disposed in a substantially linear relationship (e.g., a straight line) with respect to each other. Each of the plurality of sensors 354 receive a combination of transmitted, refracted and reflected electromagnetic radiation emitted/distributed by the plurality or pseudo-plurality of light sources 344. The reflection portion of the electromagnetic radiation may be reflected from a plunger portion of the actuator 314, and/or reflected from a housing of the dose measurement system 300 or the housing 312 of the drug delivery device 310. The refraction may be from the housing 312 and/or from the liquid drug disposed in the drug delivery device 310. The combination of the transmitted, reflected, and refracted portions of the electromagnetic radiation detected by each of the plurality of sensors yields a unique signal signature for a range of dose volumes remaining in the drug delivery device 310.

Figure 8:
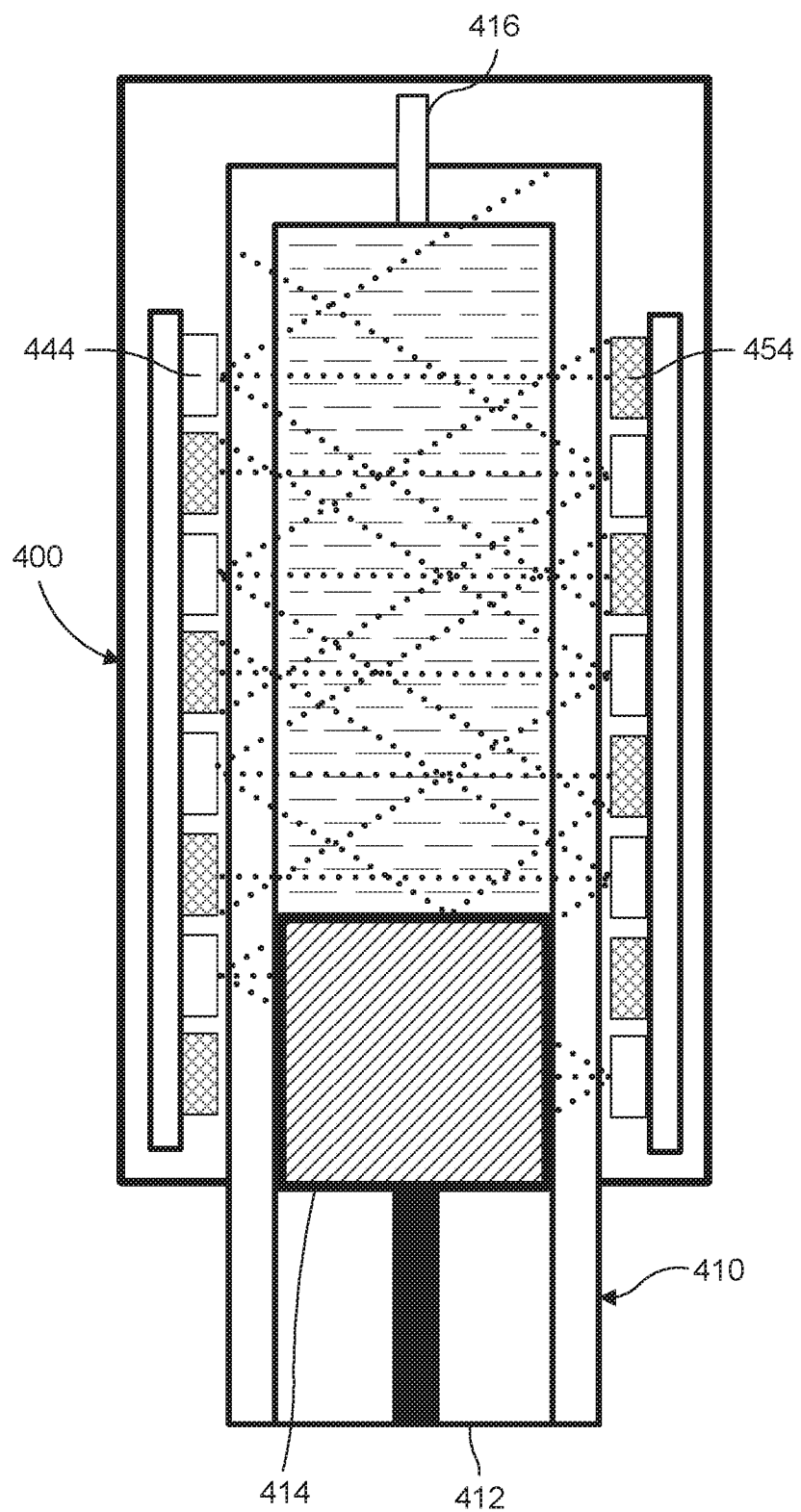
FIG. 8 is a cross-sectional view of a dose measurement system in accordance with some embodiments.

In some embodiments, a plurality or pseudo-plurality of light sources and a plurality of sensors are alternately disposed both sides of a drug delivery device. As shown in FIG. 8, a dose measurement system 400 includes a plurality or pseudo-plurality of light sources 444 and a plurality of sensors 454. The drug delivery device 410 includes a housing 412 and an actuator 414 that collectively define an internal volume (e.g., a reservoir) for containing a drug. The drug delivery device 410 also includes an injector 416 for communicating the drug to a patient. The dose measurement system 400 is configured such that the plurality or pseudo-plurality of light sources 444 and the plurality of sensors 454 are disposed on both sides of the drug delivery device. In other words, each side of the drug delivery device 410 has a plurality or pseudo-plurality of light sources 444 and a plurality of sensors 454. For example, a light guide may be shaped (e.g., as a helix) and configured to wind around the housing with openings to distribute electromagnetic radiation from opposite sides of the drug delivery device 410. This may be advantageous as emission and detection of electromagnetic radiation is now performed from both sides of the drug delivery device 410, which can, for example, remove any biases.

Figure 9:
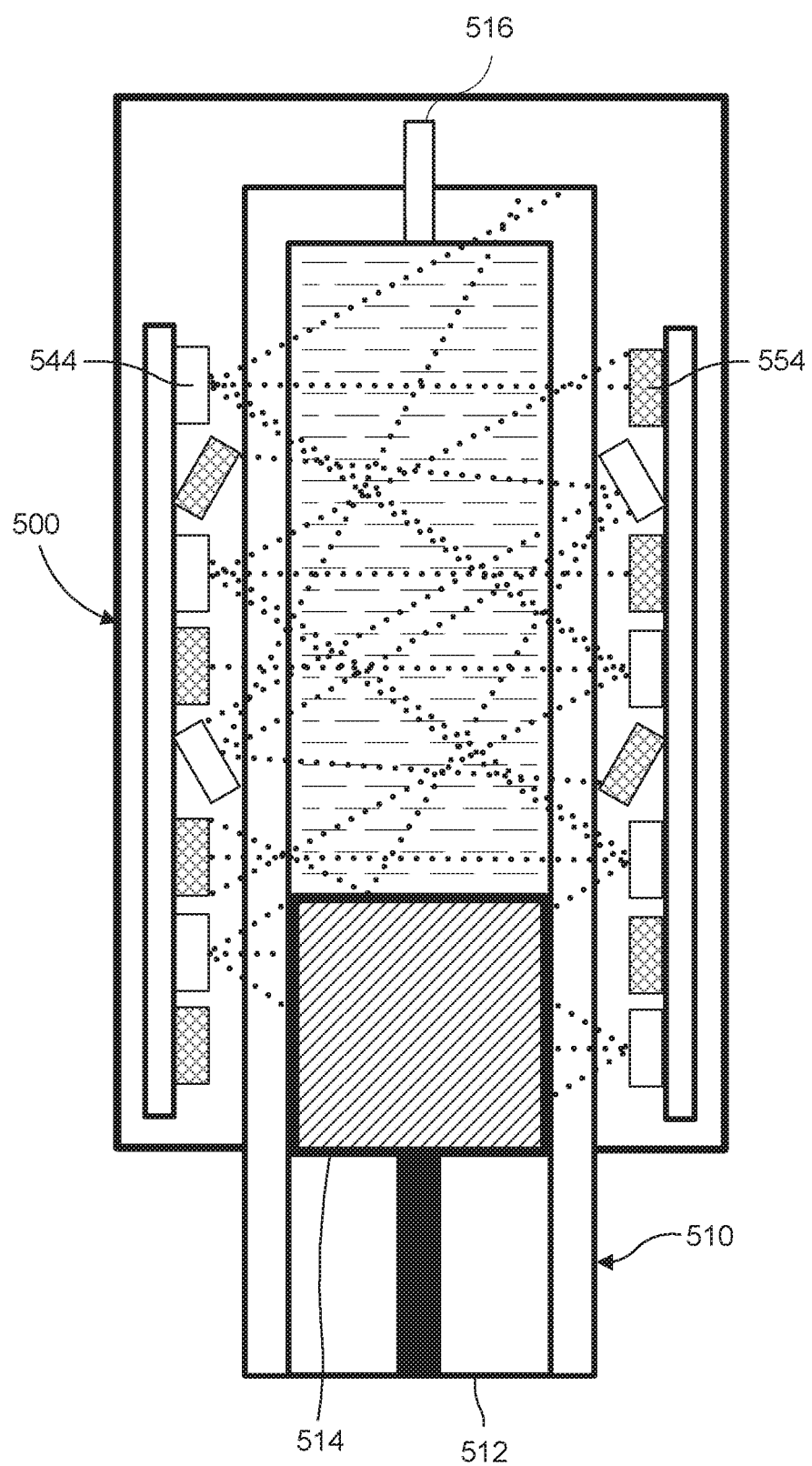
FIG. 9 is a cross-sectional view of a dose measurement system in accordance with some embodiments.

In some embodiments, at least a portion of the plurality or pseudo-plurality of light sources and/or the plurality of sensors are arranged in an angular orientation. As shown in FIG. 9, a dose measurement system 500 includes a plurality or pseudo-plurality of light sources 544 and a plurality of sensors 554. The drug delivery device 510 includes a housing 512 and an actuator 514 that collectively define an internal volume (e.g., a reservoir) for containing a drug. The drug delivery device 510 also includes an injector 516 for communicating the drug to a patient. The dose measurement system 500 is configured such that the plurality or pseudo-plurality of light sources 544 and the plurality of sensors 554 are disposed on both side of the drug delivery device 510 and have an angular orientation with respect to a longitudinal axis of the dose measurement system 500 and drug delivery device 510. This orientation may ensure that the electromagnetic radiation emitted/distributed by the plurality or pseudo-plurality of light sources 544 is incident on a larger portion of the drug delivery device 510 than is achievable with the light source and/or light guide 544 oriented in a straight line. Similarly, the plurality of sensors 554 may detect a greater portion of the electromagnetic radiation. This can, for example, result in higher resolution of the sensors 554, and/or reduce the quantity or pseudo-quantity of light sources 544 and/or sensors 554 required to achieve the desired resolution.

In some embodiments, diffused exit openings of a light guide, for example, may be used to ensure that the electromagnetic radiation emitted/distributed by the light source and/or light guide 544 is incident on a larger portion of the drug delivery device 510 than can be achievable with a narrower beam light sources 544. A diffused exit opening presents random critical angles to internal light rays, assuring the probability of light escaping from the light guide. This may also be viewed as the diffused exit opening having random indices of refraction. The exiting light rays are disbursed at random angles into a wide radiation pattern of light.

In other words, with a wider beam emitted/distributed by the light source and/or light guide 544, a higher proportion of the overall drug delivery device 510 (or of the drug reservoir) is in optical communication with the light source and/or light guide 544. Since a higher proportion of the delivery device 510 is in optical communication with the light source and/or light guide 544, a broader spectrum of electromagnetic radiation being transmitted, reflected, and/ or refracted through the drug delivery device can increase the signal strength detectable by the plurality of sensors 554. Said another way, variability in the signal signatures (as opposed to increased intensity of light incident on a sensor) increases with the broadening of the beam of light incident on the delivery device, therefore increasing the resolution of the dose measurement system 500. For example, wider angles may increase ability to distinguish states of the drug delivery device, even though the overall intensity of light may be lower. This is because distinguishing states is more about optimizing how the intensity of light changes from state to state than it is about the absolute intensity of light.

Figure 10:
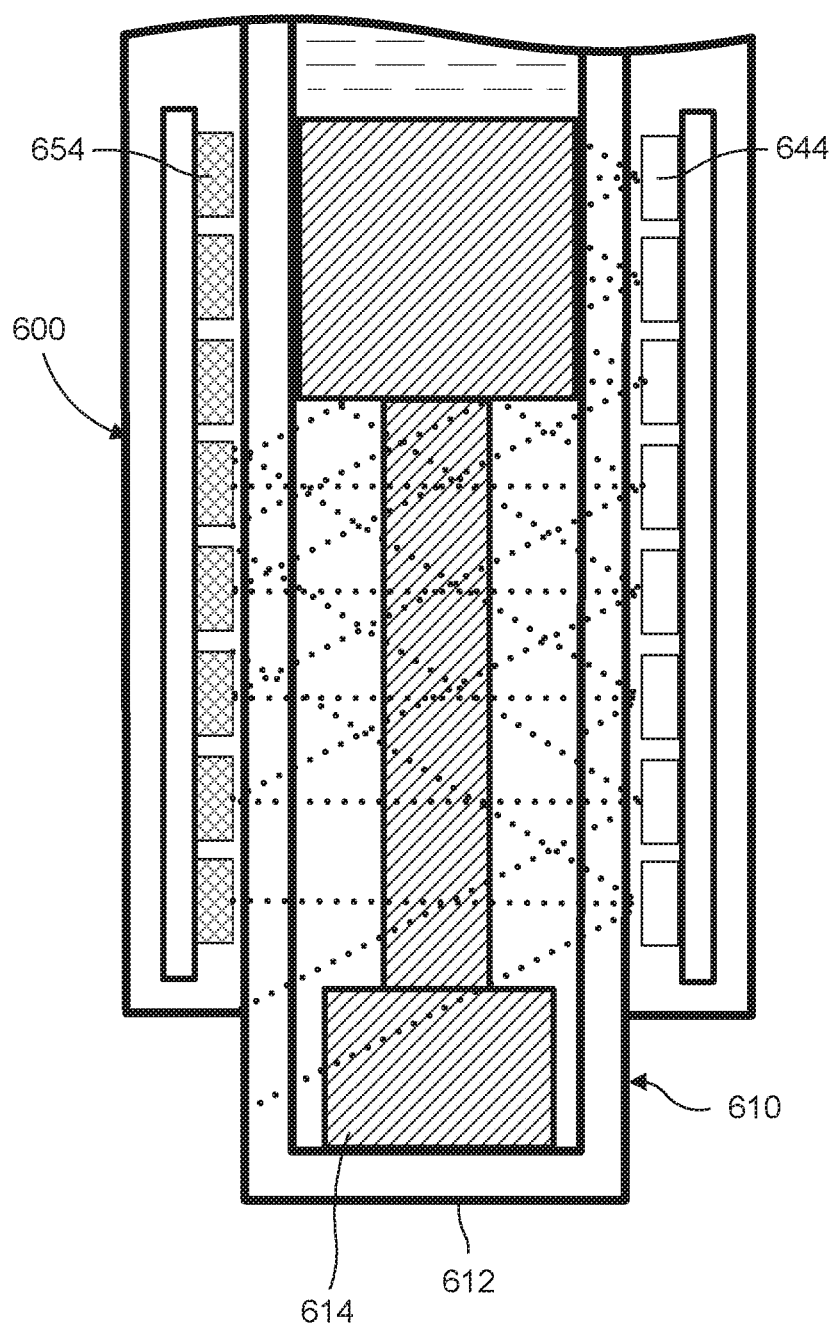
FIG. 10 is a cross-sectional side view of a dose measurement system in accordance with some embodiments.

In some embodiments, a dose measurement system is configured to detect a signal signature from a location of an actuator of a drug delivery device, which may be used to estimate the volume or number of doses remaining in the drug delivery device. As shown in FIG. 10, a dose measurement system 600 includes a light source and/or light guide 644 and a plurality of sensors 654. A drug delivery device 610 is coupled to the dose measurement system 600. The drug delivery device 610 includes a housing 612 and an actuator 614 that collectively define an interior volume (e.g. reservoir) for containing a drug. The dose measurement system 600 is disposed generally about the actuator 614 portion of the drug delivery device 610 as opposed to the dose measurement systems 300, 400, and 500 being disposed generally around the drug reservoir as shown in FIGS. 7-9. The light source and/or light guide 644 and sensors 654 are configured and arranged in a substantially similar way as described above with reference to FIG. 7. Electromagnetic radiation emitted/distributed by the plurality or pseudo-plurality of light sources 644 may be transmitted unblocked by the actuator 614, blocked by a plunger portion of the actuator 614, reflected by a body or the plunger portion of the actuator 614, and/or reflected/refracted by the housing of the drug delivery device 610. The combination of the transmitted, reflected, and refracted portions of the electromagnetic radiation detected by the plurality of sensors 654 are then used to generate a signal signature at a given position of the actuator 614. Displacement of the actuator 614 from a first position to a second position changes the transmission, reflection, and refraction pattern of the electromagnetic radiation detected by the sensors 654, creating a unique signal signature at each position of the actuator 614. This signature may be correlated to a volume or number of doses remaining in the drug delivery device 610 (e.g., by association with a reference signature).

Figure 11B:
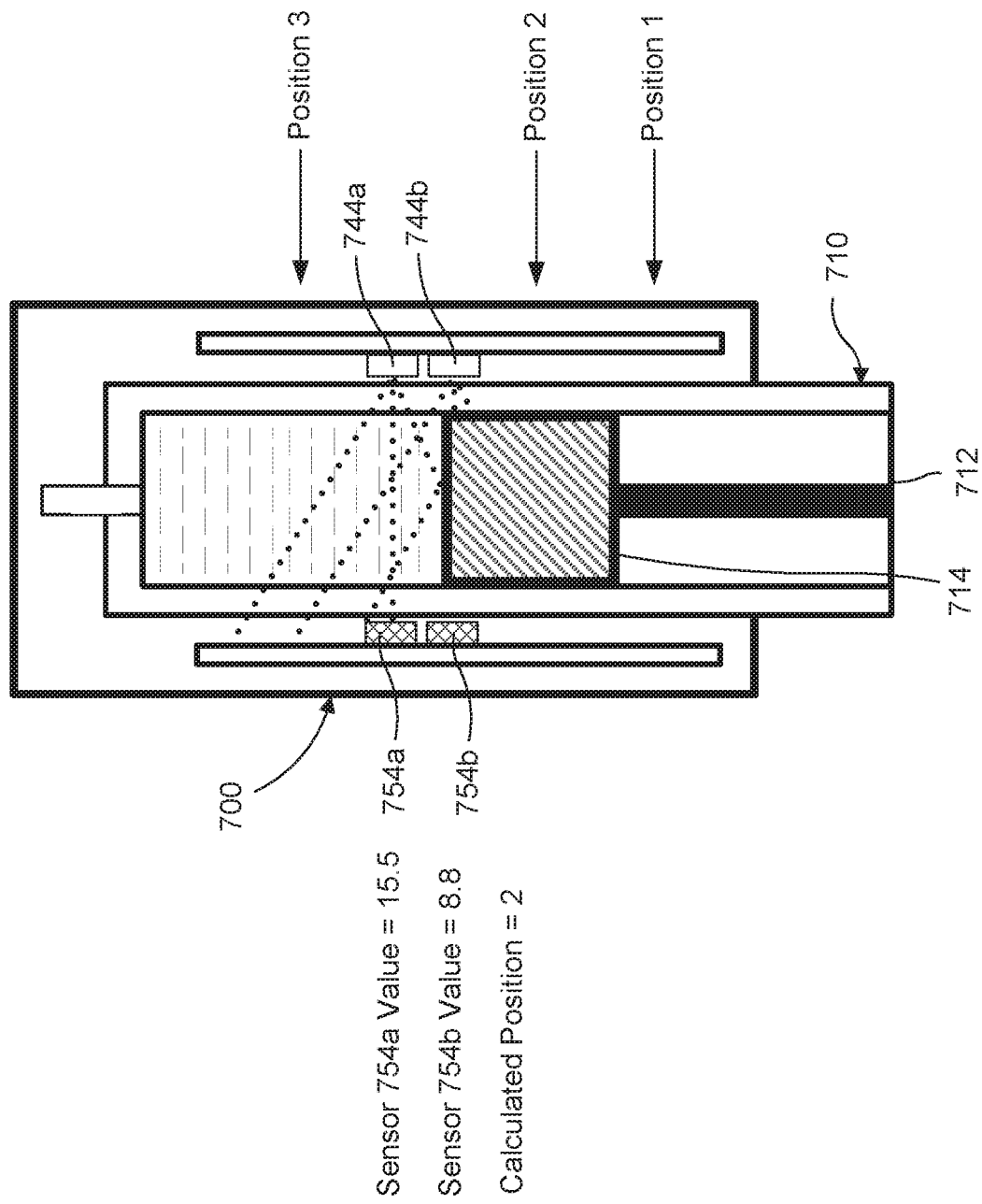
Figure 11C:
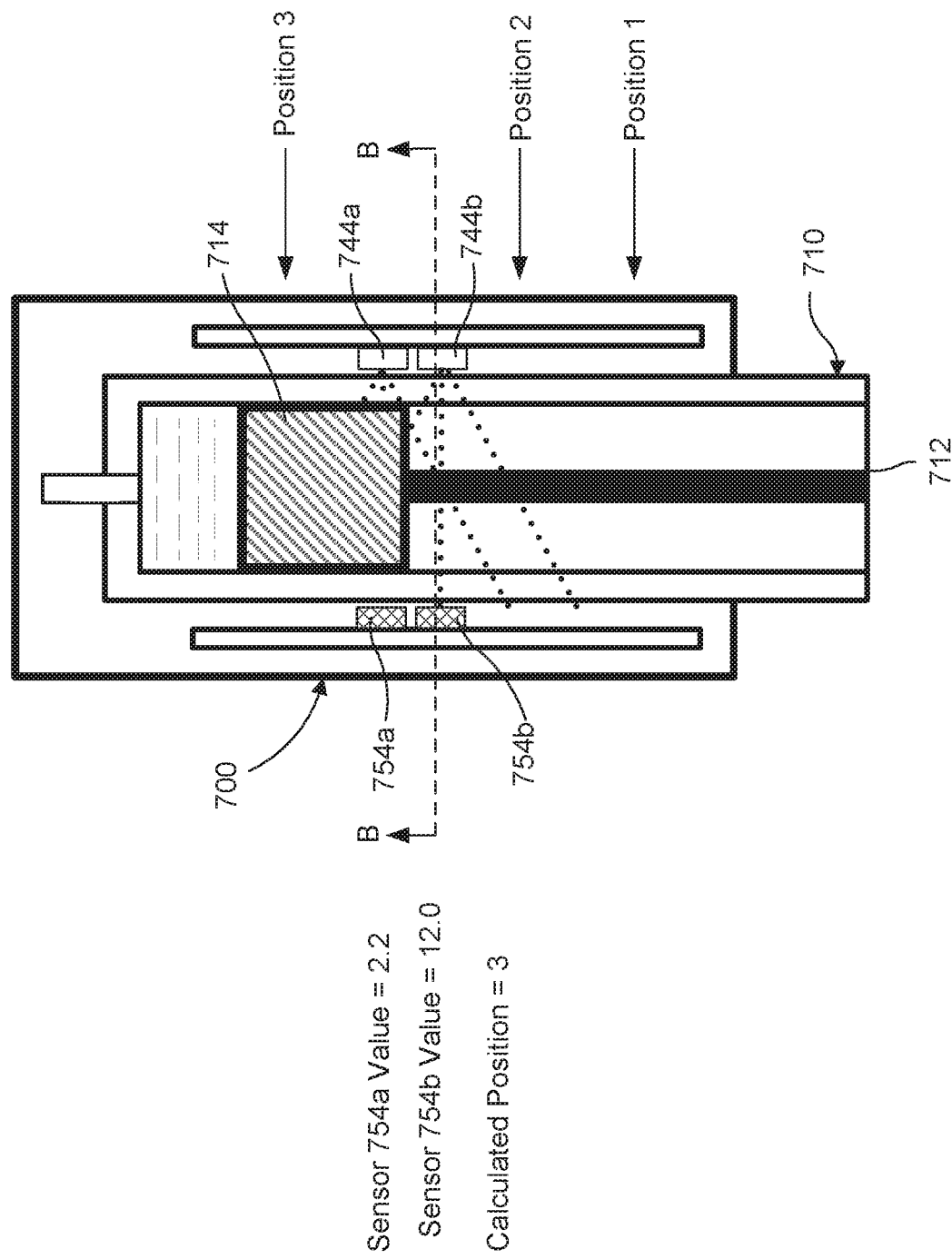

Referring now to FIGS. 11A-11C, each sensor of the plurality of sensors of a dose measurement system can detect the electromagnetic radiation emitted/distributed by at least a portion of the plurality or pseudo-plurality of light sources, and the detected electromagnetic radiation may be a combination of transmitted, reflected, and refracted electromagnetic radiation. As shown, the dose measurement system 700 includes two light sources 744a and 744b (e.g., openings in a light guide), and two sensors 754a and 754b for clarity. The dose measurement system 700 is coupled to a drug delivery device 710 which includes a housing 712 and an actuator 714 that collectively define an internal volume (e.g., a reservoir) for containing a liquid drug. The drug reservoir and at least a plunger portion of the actuator 714 are disposed substantially inside the dose measurement system 700 between the light sources 744a, 744b and sensors 754a, 754b.

As shown in FIG. 11A, the plunger portion of the actuator 714 is in a first position (position 1) such that the plunger portion is not in the line of sight of light sources 744a and 744b and sensors 754a and 754b. When electromagnetic radiation is emitted/distributed by the light sources 744a and 744b toward the drug delivery device 710, a significant portion of the electromagnetic radiation is detected by the sensors 754a and 754b in position 1. The electromagnetic radiation may include transmitted radiation, reflected radiation (e.g., by the housing 712 of the drug delivery device 710), refracted radiation (e.g., by the liquid drug and/or housing), and/or multi-direction reflection/refraction because of a curved surface of the housing 712 of the drug delivery device 710 as described in more detail below. As shown in this example, sensor 754a value is 15.3 and sensor 754b value is 13.7, which indicates that a significant portion of the electromagnetic radiation is detected by the sensors 754a and 754b.

As shown in FIG. 11B, the actuator is 714 has been displaced to a second position (position 2) such that the plunger portion partially blocks the line of sight between the light source 744b and the sensor 754b. In position 2, a significant portion of the electromagnetic radiation emitted/ distributed by the light source 744b is blocked from reaching the sensor 754b by the actuator 714, but at least a portion of the electromagnetic radiation emitted/distributed by light source 744a can still reach the sensor 754b along with any multi-directional reflected/refracted electromagnetic radiation. Furthermore, sensor 754a can receive refracted electromagnetic radiation from light source 744b and transmitted, refracted radiation from light source 744a. Sensor 754a also receives electromagnetic radiation reflected by a surface of the plunger that at least partially defines the drug reservoir. Therefore, at position 2 the sensor 754a detects an electromagnetic radiation value of 15.5 (greater than position 1), and sensor 754b detects an electromagnetic radiation value of 8.8 (less than position 1). The unique values measured at position 2 can serve as the signal signature values for position 2.

As shown in FIG. 11C, the plunger portion of the actuator 714 is in a third position (position 3) such that the plunger portion of the actuator 714 completely blocks the line of sight of the sensor 754a from the electromagnetic radiation emitted/distributed by light source 744a, such that substantially no transmitted and or reflected radiation from light source 744a can reach the sensor 754a. A portion of the transmitted electromagnetic radiation emitted/distributed by the light source 744b is also blocked by at least a portion of the actuator 714, from reaching the sensor 754b. Both the sensors 754a and 754b can still receive at least a portion of the reflected and refracted portions of the electromagnetic radiation emitted/distributed by any of the light sources 744a and/or 744b. Therefore, at position 3 the sensor 754a detects an electromagnetic radiation value of 2.2 (less than positions 1 and 2), and sensor 754b detects an electromagnetic radiation value of 12.0 (less than position 1, but greater than position 2). The unique values measured at position 3 can serve as the signal signature values for position 3.

Figure 12:
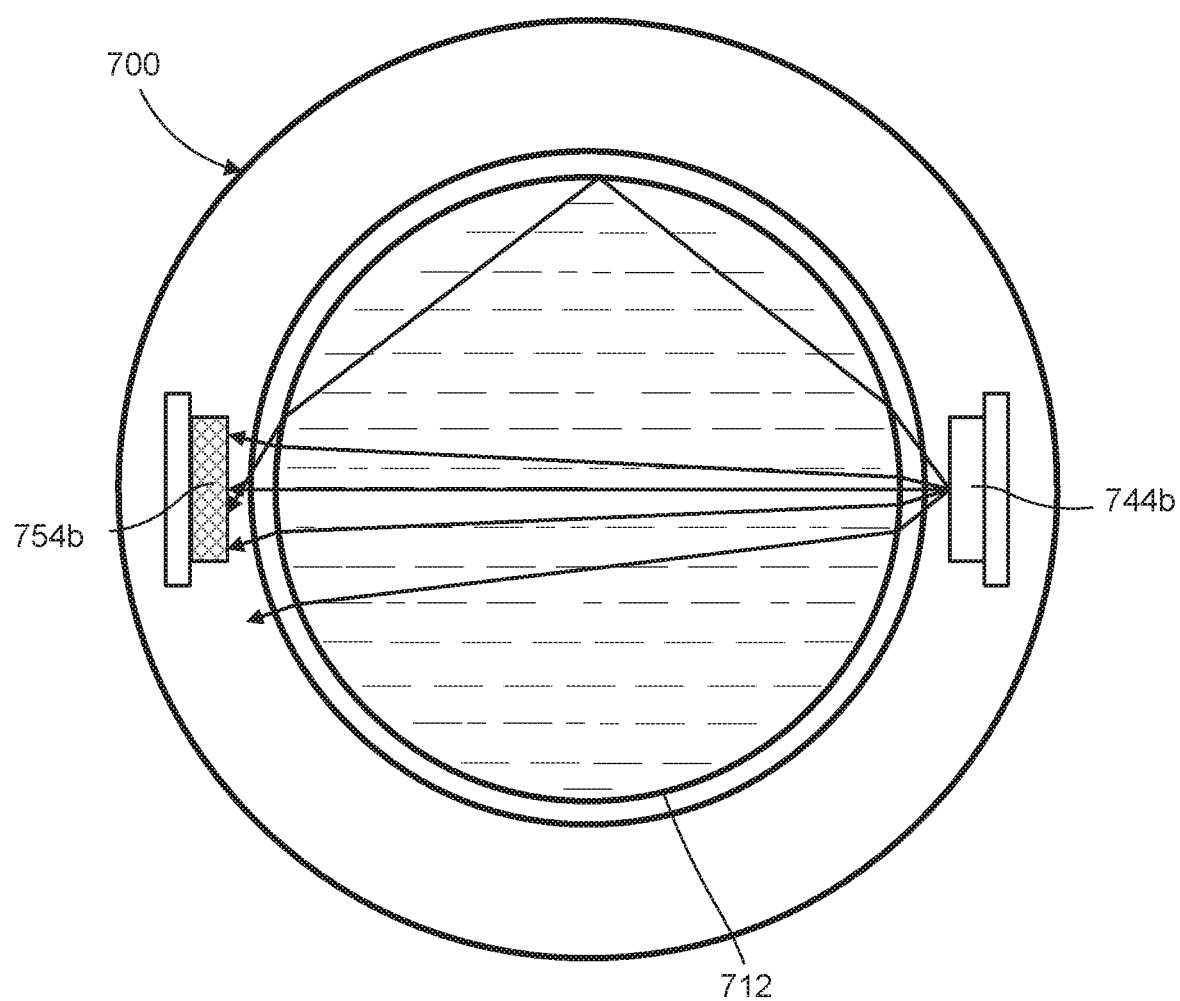
FIG. 12 is a cross-sectional view of the dose measurement system of FIG. 11A taken along line A-A, in accordance with some embodiments.

Referring now to FIG. 12, a cross section of the dose measurement system 700 taken along line AA in FIG. 11A is shown to illustrate the lensing effect caused by the curvature of the drug reservoir. As shown, a light ray emitted/distributed at a zero degree angle by light source 744b is transmitted without bending toward the sensor 754b.

Two more light rays emitted/distributed by the light source 744*b*, at an angle away from the transmitted ray, are caused to refract (bend) toward the transmitted ray as they enter the drug reservoir because the liquid drug has a higher refractive index than air. This phenomenon is referred to herein as "a lensing effect," which can result in focusing of the light rays toward the sensor 754*b*. A fourth ray is emitted/distributed at an angle further away from the transmitted ray such that it refracts at the air/drug interface, and then is further reflected by an internal surface of the housing 712 of the drug delivery system 710 such that it is incident on the sensor 754*b*. A fifth ray is emitted/distributed at an angle, such that even after refraction it is not incident on the sensor 754*b*. As described above, the combination of these rays yields a detected electromagnetic radiation value of 15.3 by sensor 754*a* and 13.7 by sensor 754*b*. These unique values measured at position 1 can serve as the signal signature values for position 1.

Figure 13:
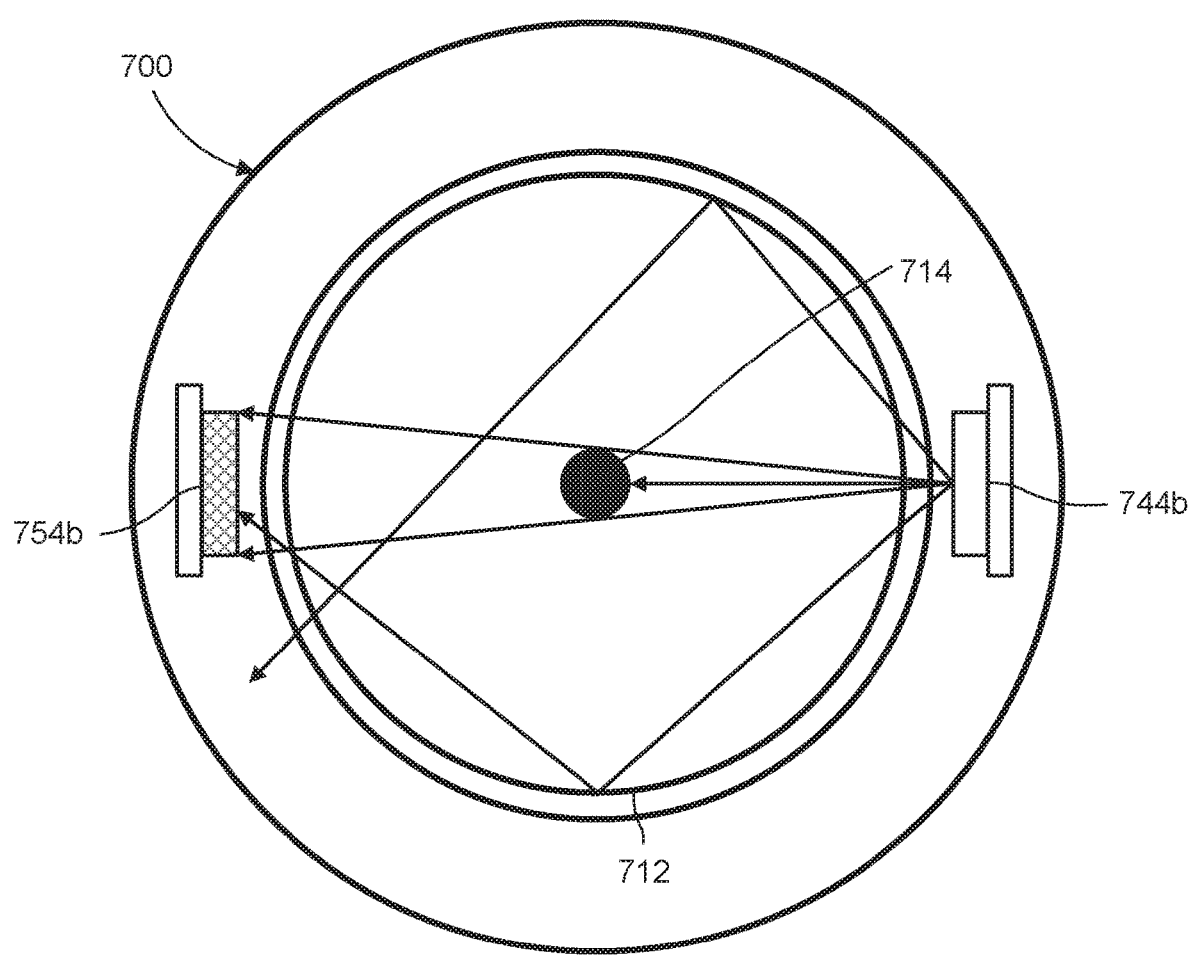
FIG. 13 is a cross-sectional view of the dose measurement system of FIG. 11C taken along line B-B, in accordance with some embodiments.

Referring now to FIG. 13, a cross-section of the dose measurement system 700 taken along line BB in FIG. 11C is shown to illustrate effect of the actuator 714 on the transmission of light. As shown, a light ray emitted/distributed at a zero degree angle by light source 744*b* is blocked by a portion of the actuator 714. Two more light rays emitted/distributed by the light source 744*b*, at an angle away from the transmitted ray, pass unrefracted (refraction through the housing is ignored) through the portion of the housing 712 of the drug delivery device 710 (there is no drug in this portion of the device 710) and are incident on the sensor 754*b*. A fourth ray is emitted/distributed by the light source 744*b* at an angle, such that it is internally reflected by the housing 712 and is incident on sensor 754*b*, while a fifth ray is internally reflected by the housing 712 but is not incident on the sensor 754*b*. The combination of these rays yields a detected electromagnetic radiation value of 2.2 by sensor 754*a* and 12.0 by sensor 754*b*. These unique values measured at position 3 can serve as the signal signature values for position 3. It is to be noted that although the line of sight of sensor 754*a* is completely blocked from light source 744*a*, reflected and refracted portions of the electromagnetic radiation still contribute to generation of a positive value.

Although the sensor values for particular positions are described as being absolute values, individual sensor values relative to other sensor values may be used to infer and/or determine the volume of liquid remaining in the drug reservoir. For example, sensor 754*a* having a particular value that is different from sensor 754*b* value by a certain amount or a certain percentage may be indicative of a position/drug volume remaining. Furthermore, a sensor value relative to two or more other sensor values may be used to generate a calibration curve of a drug delivery device 710.

Figure 14:
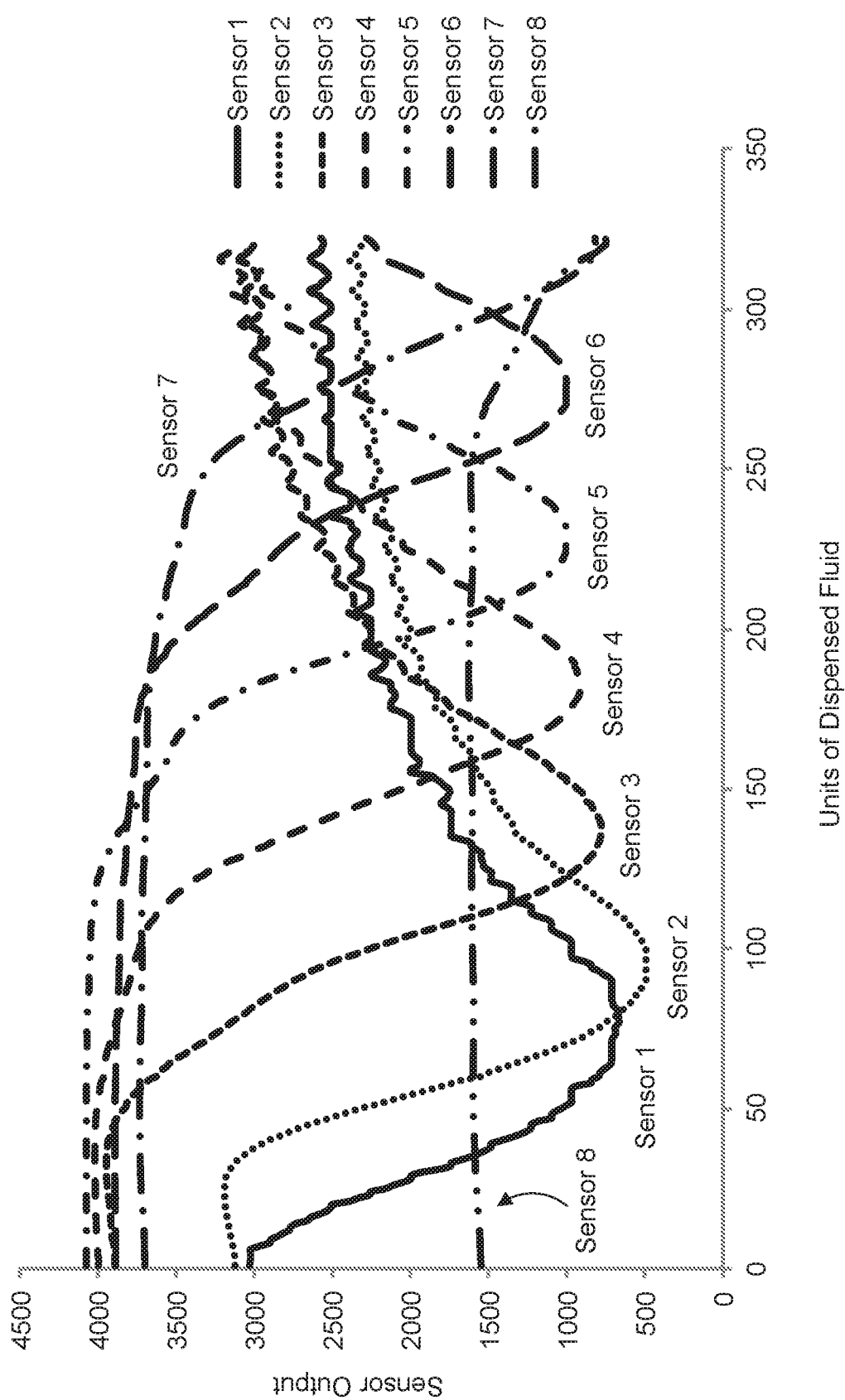
FIG. 14 is a graph showing reference signature signals of sensors of a dose measurement system in accordance with some embodiments.

A unique signal signature obtained at various configurations pertaining to the volume of dose dispensed by a drug delivery device may be used to obtain a reference signature (calibration curve) of the dose measurement system. FIG. 14 shows an example of a reference signal signature obtained for a drug delivery device using a dose measurement system that includes a total of seven sensors. The dose measurement system may be any dose measurement system as described herein. The electromagnetic radiation signature detected by each of the plurality of sensors for a range of dose volumes dispensed is stored and used to create the reference signature. As can be seen from the reference signature when the drug delivery device is almost full, sensor 1 records low amplitude of electromagnetic radiation, while sensor 7 records very high amplitude of electrode and all other sensors detect some intermediate signal signature. In contrast, when the drug delivery is completely empty, sensor 1 records very high amplitude of electromagnetic radiation, while sensor 7 records low amplitude and all other sensors detect some intermediate signal signature.

Sensor 8 detects a uniform sensor signal for a substantial portion of the dose delivered, until the almost all the dose has been delivered or the drug delivery device is almost empty. In some embodiments, the sensor 8 is used as the volume critically low sensor to indicate, for example, that the drug delivery device is nearly or completely empty. In some embodiments, the sensor 8 also is used as a usability metric sensor to detect if, for example, a drug delivery device is coupled to the dose measurement system and/or an injector included in the drug delivery device is present or not.

Therefore in this manner, the signal value recorded from all sensors for a range of drug volumes remaining yields the signal signature for the entire volume of drug in the drug delivery device. The range of drug volumes used for obtaining the signal signature may include, for example, drug delivery device completely full, drug delivery device completely empty, and a sufficient number of intermediate signatures (e.g., a signature obtained every unit of the total fluid dispensed, inclusive of all percentages there between).

In some embodiments, the reference signature is corrected for background light. For example a background signature can be detected by detecting the signal signature from the plurality of sensors in a dark state of the light source. The signal signature may be compared with the background signature to remove background noise. In some embodiments, the signal signature is associated with the reference signature to determine a drug volume in the drug delivery device, using probabilistic matching algorithms. In some embodiments, the plurality or pseudo-plurality of light sources and the plurality of sensors are configured such that the dose measurement system can detect the volume of drug in the drug delivery device with a resolution of 1 unit of drug, and/or position of a plunger portion of an actuator disposed in the drug delivery device 110 with a resolution of 100 micrometers, 110 micrometers, 120 micrometers, 130 micrometers, 140 micrometers, 150 micrometers, 160 micrometers, 170 micrometers, 180 micrometers, or 200 micrometers, inclusive of all ranges therebetween.

Figure 15:
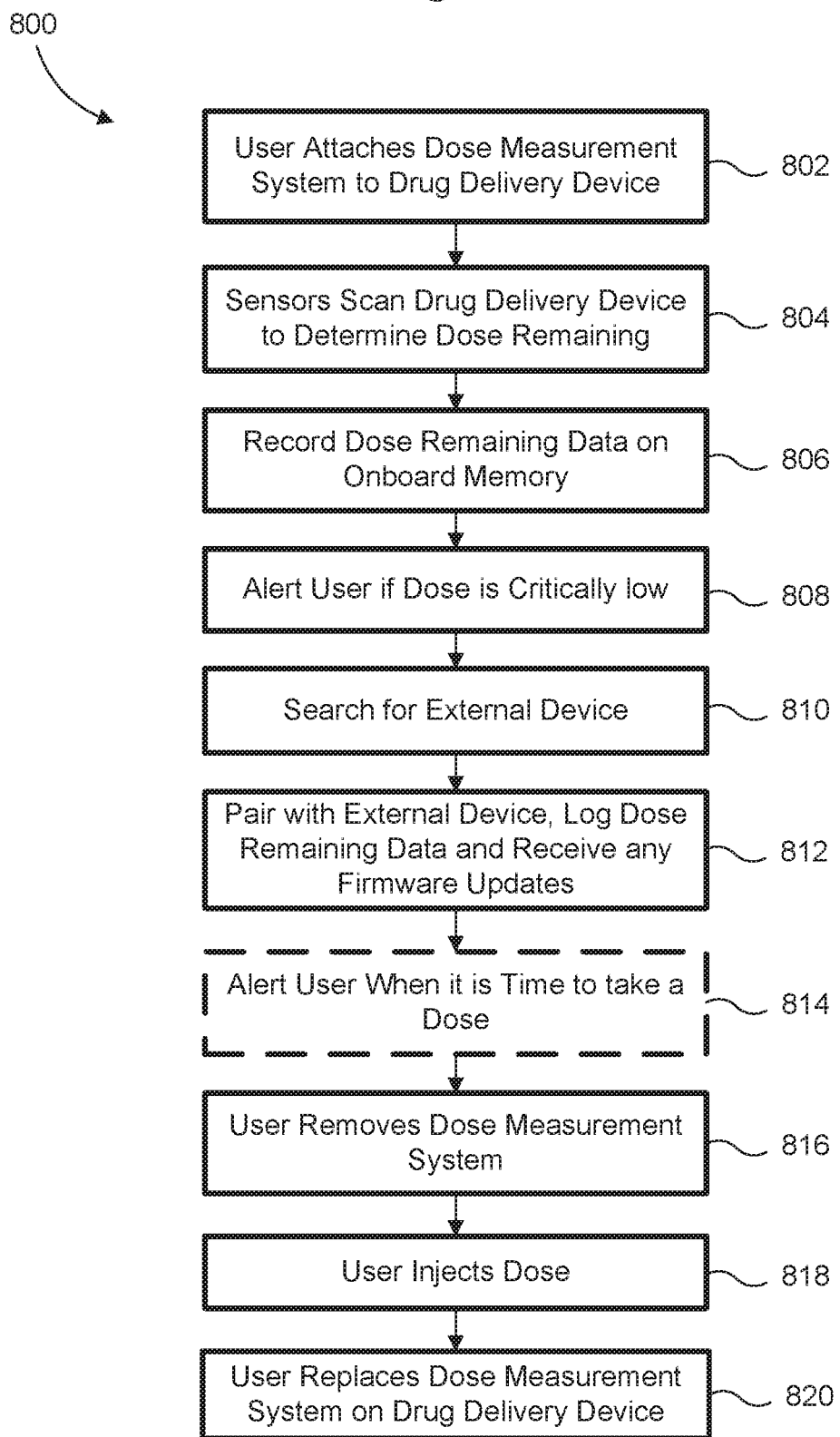
FIG. 15 is a flow diagram of a method of operation of the dose measurement system in accordance with some embodiments.

FIG. 15 illustrates a flow diagram showing a method 800 for measuring a volume or number of doses remaining in a drug delivery device using any of the dose measurement systems described herein. A user attaches a dose measurement system to a drug delivery device 802. A plurality of sensors disposed in the dose measurement system scan the drug delivery device to determine the volume or number of doses remaining 804. For example, a processing unit of the dose measurement system can associate the signal signature detected by the plurality of sensors with a reference signature to determine the volume or number of doses remaining. The sensor data is recorded on an onboard memory 806, such as an RFID chip and/or a memory that is part of the processing unit of the dose measurement system. The dose measurement system alerts the user if the volume or number of doses remaining is critically low 808. Audio, visual, and/or tactile alerts may be used to alert the user. A communications module of the dose measurement system searches for an external device 810. For example, a Bluetooth® wireless technology connection may be activated to search for the external device, such as a smart phone app, a local computer or a remote server. The dose measurement system pairs with the external device and logs remaining volume or dose data on the external device and/or receives any firmware updates 812. Optionally, the dose measurement system also may alert a user when it is time to take a dose 814. After dose data has been recorded and transmitted to an external device, the user can remove the dose measurement system from the drug delivery device 816. The user then injects a pre-determined volume of the dose using the drug delivery device 818. The user finally replaces the dose measurement system on the drug delivery device 820. The method 800 can then be repeated.

Figure 16:
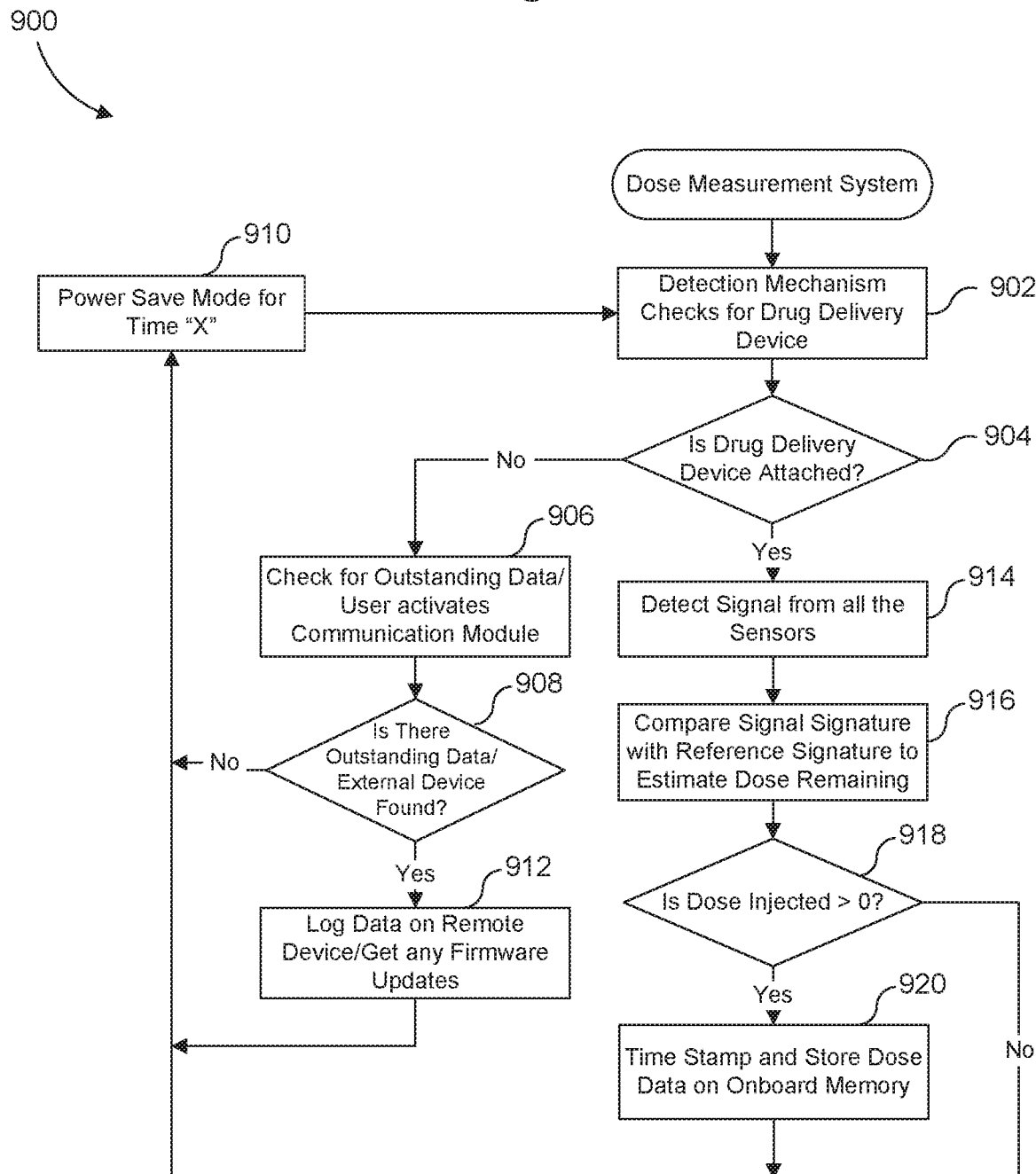
FIG. 16 is a flow diagram of a method of operation of the dose measurement system in accordance with some embodiments.

FIG. 16 illustrates a flow diagram showing a method 900 for conserving power when the dose measurement system is not in use. The method 900 described herein may be used with any of the dose measurement systems described herein. In a first step, a detection mechanism of the dose measurement system checks for a drug delivery device 902. The drug delivery device can either be coupled or uncoupled to the dose measurement system 904. If the drug delivery device is not attached, the dose measurement system automatically checks for outstanding data in the memory to be logged to an external device or the user can activate a communications module of the dose measurement system 906. In some embodiments, the communications module is only activated when the dose measurement system is attached to a drug delivery device. The dose measurement system then determines if there is onboard data to be logged and if an external device was found 908. If there is no onboard data to be logged and no external device was found, the dose measurement system goes into a power save mode for a pre-defined time "X" 910. For example, a processing unit of the system can turn off a communications module of the dose measurement system and/or turn off the electronics controlling a light source and/or plurality of sensors of the dose measurement system. Time "X" may be, for example, 1 minute, 10 minutes, 1 hour, or any time therebetween. Alternatively, if there is data to be logged and an external device was found, the dose measurement system pairs with the external device and logs data on the external device and/or receives any firmware updates from the external device 912. The dose measurement system can then go into the power save mode 910. If instead a drug delivery device was found to be attached to the dose measurement system 904, the dose measurement system scans the drug delivery device and collects signal from all of the plurality of sensors 914. The signal from each of the plurality of sensors may be used to create a signal signature corresponding to the volume or number of doses remaining in the drug delivery device. A processing unit of the dose measurement system compares the signal signature with a reference signature to estimate the volume or number of doses remaining in the drug delivery device 916. The dose measurement system determines if the dose injected was greater than zero 918. If the dose injected was greater than zero, the dose measurement system time stamps and stores the dose on an onboard memory 920. The dose measurement system then goes into the power save mode for the time "X" 910. If the dose injected was not greater than zero 918, than the dose measurement system directly goes into the power save mode for the time "X" 910.

Figure 17:
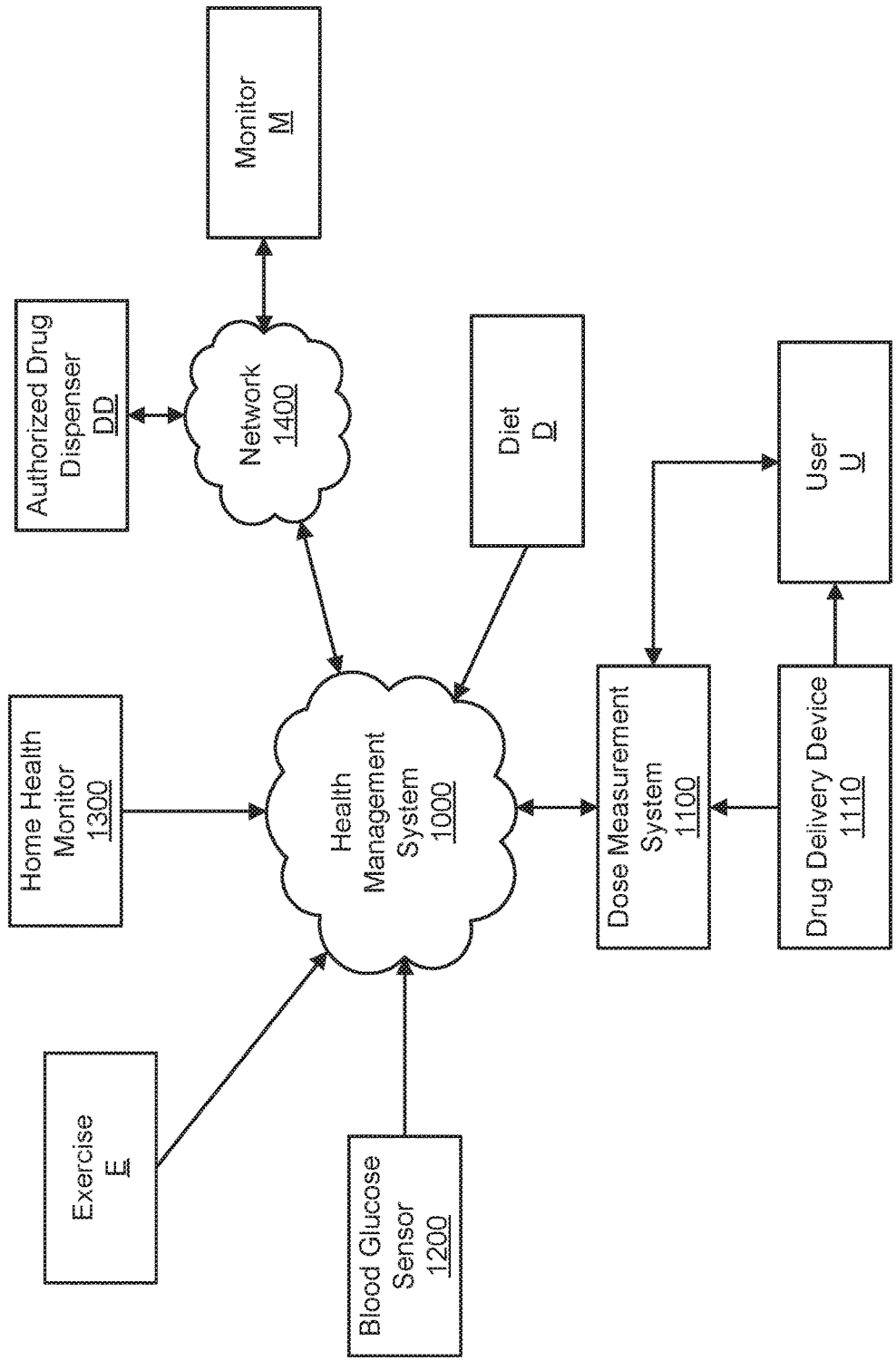
FIG. 17 is a schematic block diagram of a health management system associated with a dose measurement system in accordance with some embodiments.

In some embodiments, any of the dose measurement systems described herein may be associated with a health management system to manage the health of a patient suffering from Type I or II diabetes. FIG. 17 shows a schematic block diagram of a health management system 1000 for managing the health of a diabetic user U. In some embodiments, the health management system includes a smart phone application. In some embodiments, the health management system includes a local computer and/or a remote server. The health management system is in two-way communication with a dose measurement system 1100 that may be reversibly coupled to a drug delivery device 1110. The drug delivery device 1110 may be an insulin injection pen or syringe for administering insulin to a user U. The dose measurement system also may communicate information to a user or receive an input from the user. The health management system 1000 is configured to receive the user exercise data E and diet data D. The health management system 1000 is also configured to receive blood glucose data from a blood glucose sensor 1200. The health management system 1000 can further be configured to receive user health data from a home health monitor 1300 (e.g., weight, blood pressure, EKG, oxygen saturation, actigraphy measures, pulmonary function, water retention, temperature, etc.). The health management system 1000 may be in two-way communication with a network 1400. The network can be, for example, a remote server or a call center. The network 1400 also may be in two-way communication with a monitor M and an authorized drug dispenser DD. The monitor M may be a doctor, a care giver, a pharmacy, and/or a clinical trial manager. The authorized drug dispenser DD may be a pharmacy or a clinical trial manager.

In some embodiments, the dose measurement system 1100 communicates to the health management system the insulin volume or number of insulin doses remaining in and/or the insulin dose delivered to the user U by the drug delivery device 1110. In some embodiments, the health management system also includes a memory for storing the user U insulin dose regimen and/or any other medication schedule. The user U medication regimen may be communicated to the health management system 1100 by, for example, the monitor M and/or the authorized drug dispenser DD through the network 1400. In some embodiments, the health management system 1100 is used to process user U health data, for example, user U blood glucose levels, exercise data E, diet data D, and/or home health monitored data to determine the status of patient health. In some embodiments, the health management system 1000 is configured to compare dose delivered to a patient with a patient medication schedule to monitor compliance. In some embodiments, the health management system can communicate the user health and dose information to the monitor M through the network 1400. The monitor M can analyze user U health data and determine if any changes to the patient medication plan, for example, insulin and/or any other medication dosage needs to be made. If a change is required, in some embodiments, the monitor M can communicate any changes to the user's U medication regimen to the authorized drug dispenser DD. In some embodiments, the monitor M also communicates this information to the health management system 1100 through the network 1400. In some embodiments, the health management system 1100 can update and store the user U medication regimen and also communicate to the dose measurement system 1100, the user U new medication regimen. The user U can then access the dose measurement system 1400 to obtain the new measurement plan, for example, new insulin dosage. In this manner, a diabetic user's U health may be monitored and managed and the user's U medication schedule may be dynamically personalized to the user U. In some embodiments, health management system also may communicate the user U health and medication history on a periodic basis. The health and medication history may be used, for example, to inform the user U of any changes that need to be made to improve the user's U overall health. The medication history also may be communicated to the monitor M to analyze the user's U progressive health.

In some embodiments, a light module includes a single light source and a light guide for transporting, distributing, and/or redirecting light from the single light source. For example, FIGS. 18-24 are various views of a dose measurement system 1500. The dose measurement system 1500 includes a lighting module 1540, a sensing module 1550, a processing unit (not shown), a communications module 1570, and a power source 1586 in accordance with some embodiments. The lighting module 1540 may include a light source 1548 and a light guide 1546. The sensing module 1550 may include a plurality of sensors 1554. The dose measurement system 1500 may be configured to be coupleable to a drug delivery device (not shown) (also referred to herein as an "injection pen"). The drug delivery device may be configured to deliver a predefined quantity of a drug (e.g., a dose) to a patient. Examples of the drug delivery device include insulin injection pens that may be used by a patient to self-administer insulin. The drug delivery device may have the same or similar structure and function as the drug delivery device 210 described above with reference to the dose measurement system 200 shown in FIGS. 2-4. For example, the drug delivery device may include a housing, an actuator, and an injector. The housing may be relatively opaque, such that it only allows select wavelengths of electromagnetic radiation to be transmitted therethrough (e.g., infrared or microwave radiation). The housing defines an internal volume (e.g., reservoir) for storing a drug. The actuator may include a plunger portion in fluid communication with the drug and configured to communicate a predefined quantity of drug to the patient. The actuator may be configurable (e.g., by the user) to dispense variable quantities of the drug. The injector is configured to penetrate a user's skin for intramuscular, subcutaneous, and/or intravenous delivery of the drug.

Figure 18:
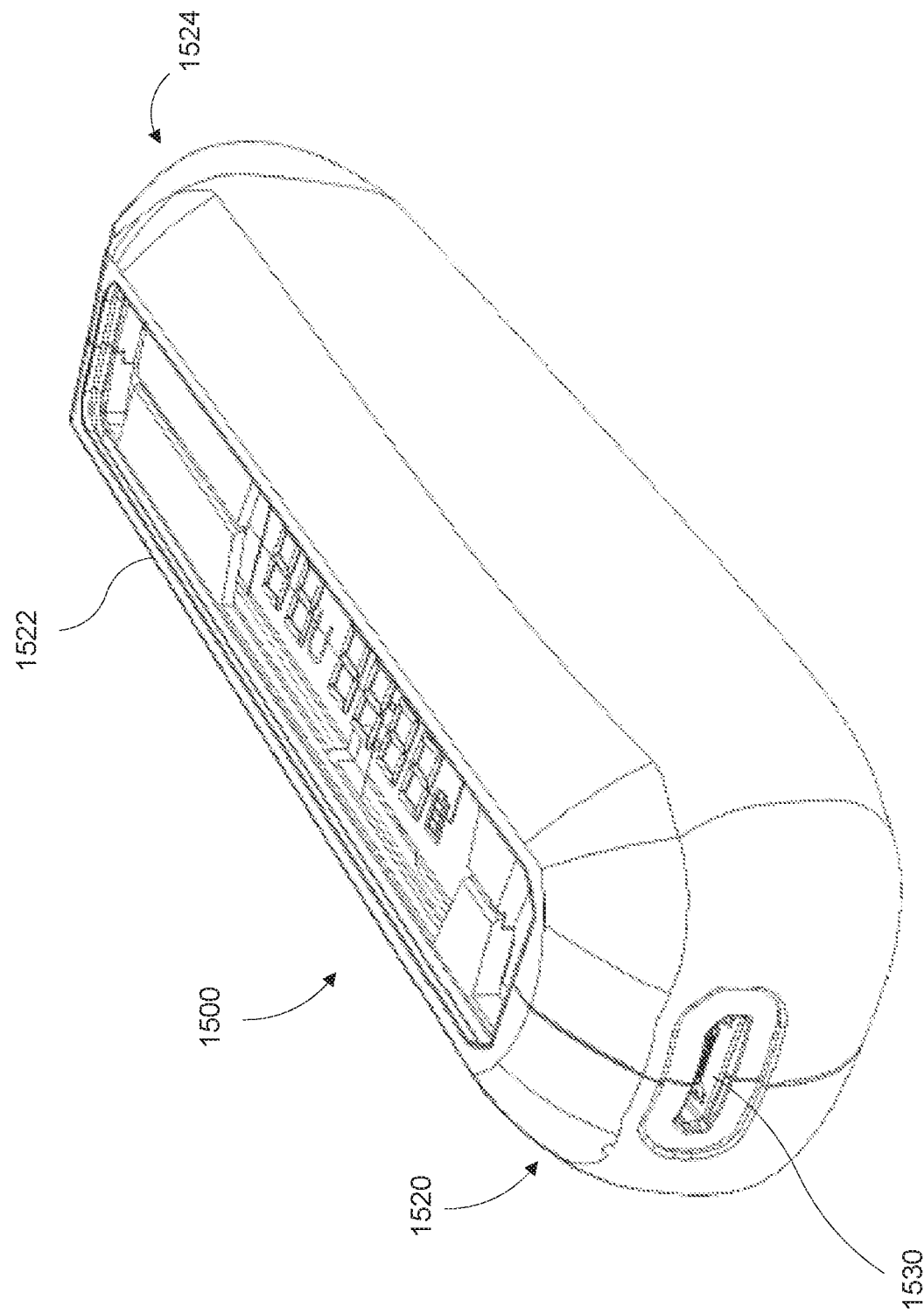
FIG. 18 is a perspective view of a dose measurement system in accordance with some embodiments.

FIG. 18 is a perspective view of the dose measurement system 1500. As shown in FIG. 18, the dose measurement system 1500 includes a housing 1520 that includes a first housing portion 1522 (also referred to herein as "first housing 1522") and a second housing portion indicated at 1524 (also referred to herein as "second housing 1524"). At least a portion of the second housing portion 1524 may be configured to be disposed within an internal volume defined by the first housing portion 1522. The first housing portion 1522 and the second housing portion 1524 may be removably or fixedly coupled together by, for example, gluing, hot welding, a snap-fit mechanism, screws, or by any other suitable coupling means. The housing 1520 may be made from a rigid, light weight, and opaque material, such as polytetrafluoroethylene, high density polyethylene, polycarbonate, another plastic, acrylic, sheet metal, any other suitable material, or a combination thereof. The housing 1520 also may be configured to shield the internal electronic components of the dose measurement system 1500 from environmental electromagnetic noise. For example, the housing may include an insulation structure (not shown) that is, for example, lined with aluminum or any other metal sheet or foil that can serve as an electromagnetic shield.

Figure 19:
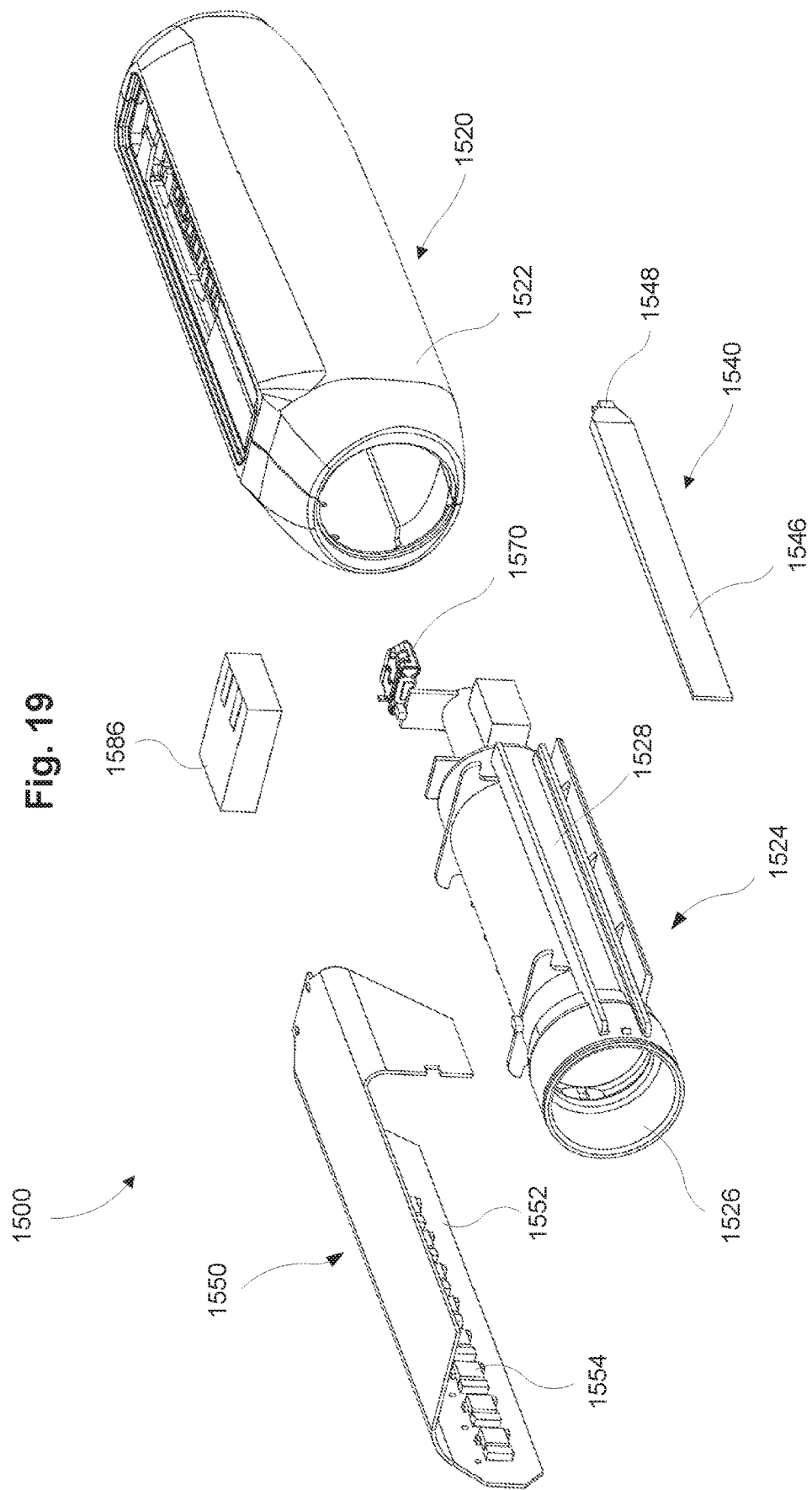
FIG. 19 is an exploded perspective view of the dose measurement system of FIG. 18 in accordance with some embodiments.

FIG. 19 is an exploded perspective view of the dose measurement system 1500. As shown in FIG. 19, the first housing portion 1522 defines an internal volume for substantially housing the lighting module 1540, the sensing module 1550, the processing unit, the communications module 1570, the power source 1586, and at least a portion of the second housing portion 1524. The second housing portion 1524 defines a bore 1526, shaped and sized to receive at least a portion of the drug delivery device. For example, the bore 1526 may be shaped and sized to receive only the drug containing portion of the housing and the injector of the drug delivery device. The bore 1526 may be configured to receive the drug delivery device in a preferred orientation, such as a preferred radial orientation. In some embodiments, the bore 1526 is in close tolerance with the diameter of the drug delivery device, for example, to form a friction fit with the drug delivery device. In some embodiments, the bore 1526 includes one or more notches, grooves, detents, any other snap-fit mechanism, and/or threads, for removably coupling the drug delivery device to the second housing 1524. In some embodiments, the second housing portion 1524 includes one or more alignment features to allow the drug delivery device to be coupleable with the dose measurement system 1500 in a predetermined radial orientation.

Figure 20:
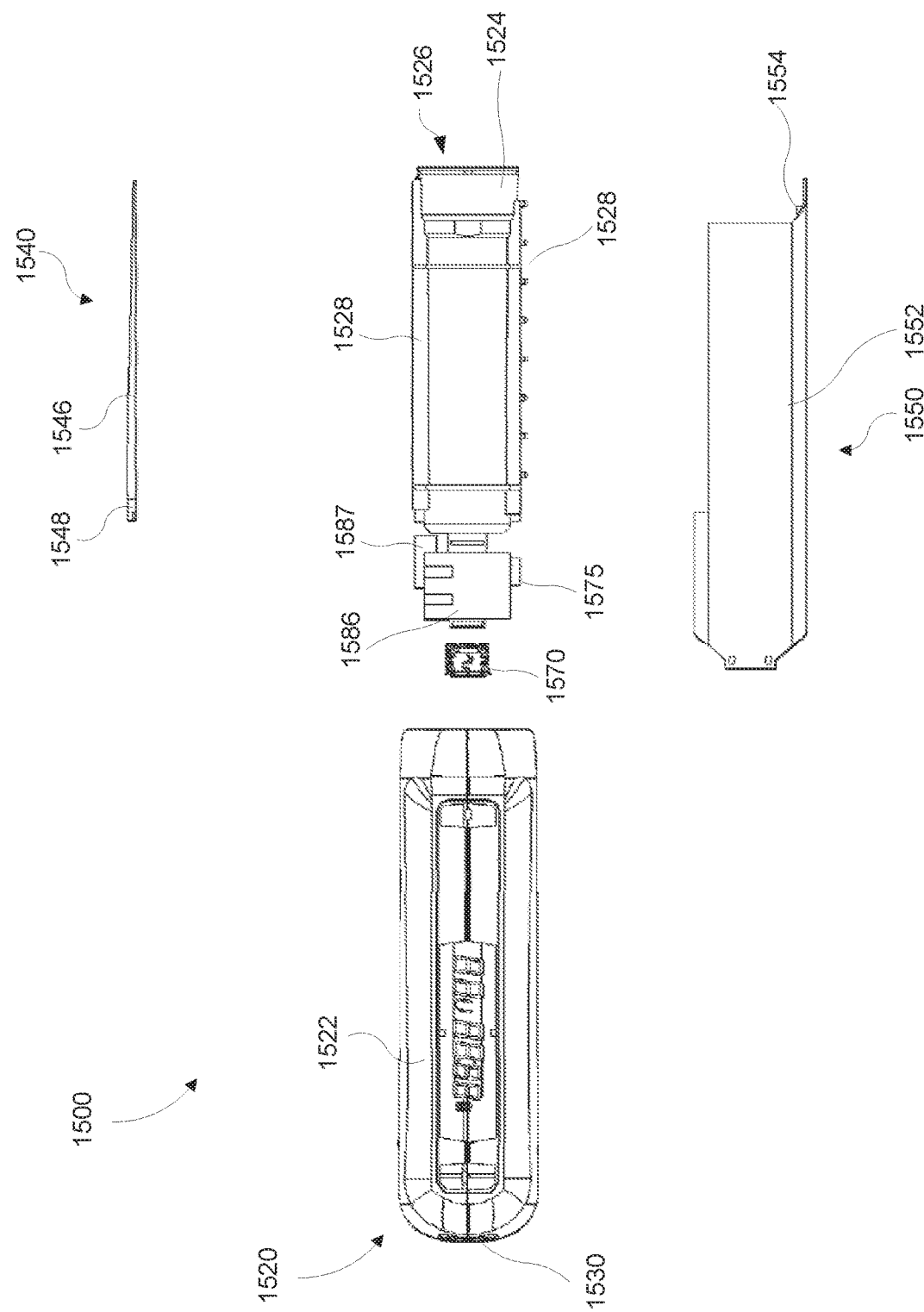
FIG. 20 is an exploded top view of the dose measurement system of FIG. 18 in accordance with some embodiments.

FIG. 20 is an exploded top view of the dose management system 1500. As shown in FIG. 20, the first housing 1522 includes an opening 1530 for receiving at least a portion of the communications module 1570 such as, for example, a communication interface to provide wired communication with an external device and/or an interface for charging the power source 1586. In some embodiments, the first housing 1522 also includes features (e.g., recesses, apertures, cavities, etc.) for receiving a portion of the drug delivery device such as the injector. In some embodiments, the housing 1520 also includes a detection mechanism (not shown) to detect if the drug delivery device has been coupled to the dose measurement system 1500 (e.g., a push switch, a motion sensor, a position sensor, an optical sensor, a piezoelectric sensor, an impedance sensor, or any other suitable sensor). The housing 1520 may be relatively smooth and free of sharp edges. In some embodiments, the housing 1520 is shaped to resemble a pen cap that has a form factor that occupies minimal space (e.g., can fit in the pocket of a user). In some embodiments, the housing 1520 also includes features (e.g., clips for attaching to a user's shirt pocket) and/or other ornamental features. In some embodiments, the dose measurement system 1500 also may serve as a replacement cap for the drug delivery device.

The processing unit may include a PCB (not shown) and a processor (not shown). The processing unit may be the same or similar to the processing unit 260 described above with reference to the dose measurement system 200 described above and will not be further described herein. The communications module 1570 may be the same as or similar to the communications module 270 described above with reference to the dose measurement system 200 and will not be further described herein. For example, the communications module 1570 may include a speaker 1575 for providing audible alerts or messages to the user, including, but not limited to, dose reminders, reinforcement messages, and/or a microphone (not shown) for receiving audio input from the user. The power source 1586 may be any power source that can be used to power the dose measurement system 1500. The power source 1586 may be the same or similar to the power source 286 described above with respect to the dose measurement system 200 and will not be further described herein. In some embodiments, as shown in FIG. 20, the dose measurement system 1500 includes a capacitor 1587.

Figure 21:
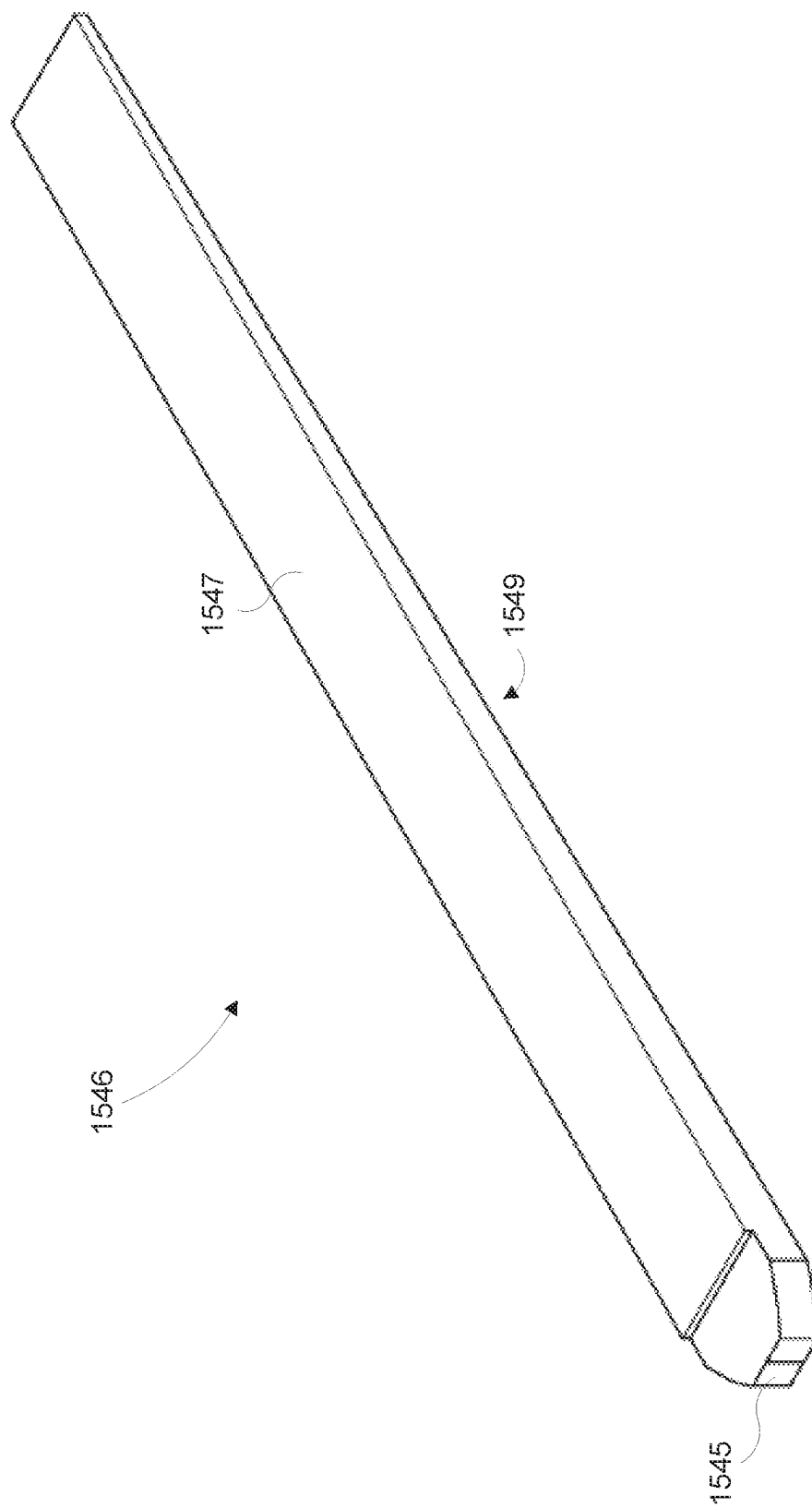
FIG. 21 is a perspective view of a light guide of the dose measurement system of FIG. 18 in accordance with some embodiments.

FIG. 21 is a perspective view of the light guide 1546 of the light module 1540 according to an embodiment. In some embodiments, the light guide 1546 is an internally reflective light tube/pipe and/or other light distribution member) for transporting and/or distributing light. In some embodiments, the light guide 1546 is formed from molded transparent plastic, such as, for example, polycarbonate. In other embodiments, the light guide 1546 is formed of one or more other optical grade materials such as acrylic resin, polycarbonate, epoxies, and glass. In some embodiments, the light guide 1546 can be, for example, injection molded. The light guide 1546 may be a monolithic structure. Said another way, the light guide 1546 may be formed from one piece of material.

Figure 22:
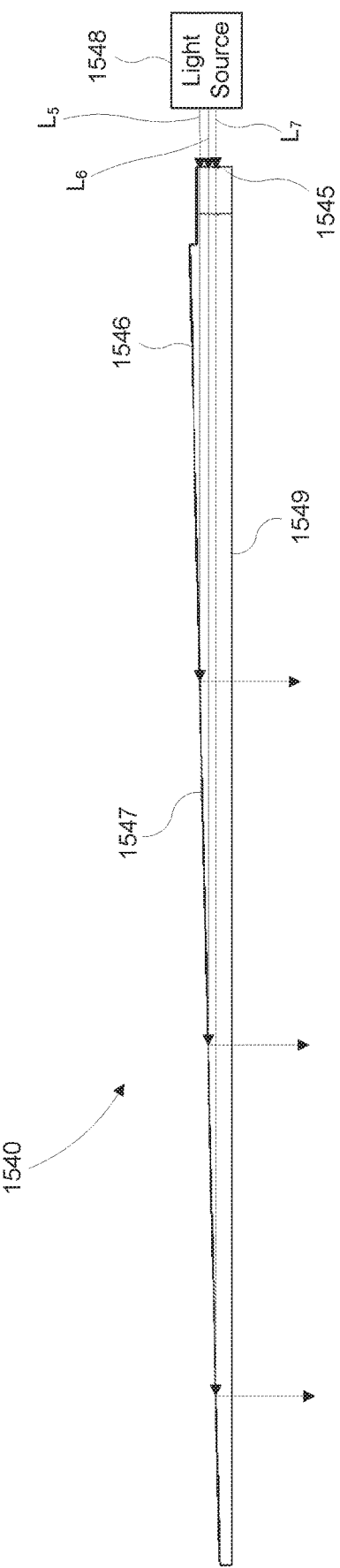
FIG. 22 is a schematic side view of the light guide of FIG. 18 in accordance with some embodiments.

The light guide 1546 may be configured to transport electromagnetic radiation (e.g., light) from the light source 1548 toward the sensor module 1550 with minimal loss by means of total internal reflection. The light guide 1546 may have any suitable shape that allows for the collection of electromagnetic radiation from the light source 1548 and output of electromagnetic radiation toward the sensor module 1550. For example, as shown in FIG. 19, the light guide 1546 may include an end wall 1545, a first wall 1547, and a second wall indicated at 1549. The first wall 1547 may be angled relative to the second wall 1549 such that the first wall 1547 is configured to reflect electromagnetic radiation toward the second wall 1549. Said another way, the light guide 1546 may be shaped as a wedge. For example, FIG. 22 is a schematic side view illustration of the light guide 1546. As shown in FIG. 22, a first light ray $L_5$, a second light ray $L_6$, and a third light ray $L_7$ are emitted by a single light source 1548 through the end wall 1545. Each of the first light ray $L_5$, the second light ray $L_6$, and the third light ray $L_7$ are reflected by the first wall 1547 toward the second wall 1549 and out of the light guide 1546 via the second wall 1549.

The light guide 1546 and the light source 1548 may be mounted on, or otherwise disposed on, the second housing portion 1524. Specifically, the light guide 1546 may be mounted on, or otherwise disposed on, an aperture 1528 of the second housing portion 1524. In some embodiments, light guide 1546 is arranged such that, when the portion of the drug delivery device that defines the internal volume of the housing holding the drug is coupled with the dose measurement system 1500, the light guide 1546 can illuminate the entire internal volume. While the light guide 1546 is shown and described as having a wedge shape, in some embodiments the light guide 1546 is formed in any suitable shape configured for even dispersal of electromagnetic radiation, including but not limited to straight, bent, and triangular.

In some embodiments, the light guide 1546 includes a reflective material (not shown) on a portion of the light guide 1546 to direct electromagnetic radiation traveling through the light guide 1546. For example, reflective material may be disposed on the first wall 1547 to direct electromagnetic radiation through the second wall 1549 toward the interior of the second housing 1524, the drug delivery device, and/or the sensors 1554 of the sensor module 1550.

The light source 1548 may be a single LED. The LED may be any suitable type of LED, such as, for example, an infrared (IR) LED. The angle of output of the light source 1548 may be arranged relative to the end wall 1545 of the light guide 1546 such that electromagnetic radiation from the light source 1548 can travel through and be distributed by the light guide 1546. For example, the light source 1548 may be arranged at an angle relative to the end wall 1545 of the light guide 1546 such that the angle is optimized for even distribution of electromagnetic radiation from the second wall 1549 toward the interior of the second housing 1524 and the sensors 1554 of the sensor module 1550.

In some embodiments, the light source 1548 is configured to produce an electromagnetic radiation of a wavelength that is capable of being dispersed by the light guide 1546 and penetrating through the housing of the drug delivery device, the drug contained therein, and/or a portion of the housing 1520. For example, infrared radiation or microwave radiation can penetrate many of the plastic materials that are commonly used in manufacturing drug delivery devices (e.g., injection pens). In some embodiments, an electromagnetic radiation has a frequency that can penetrate through the internal components of the drug delivery device, including, but not limited to, the plunger portion of the actuator. In some embodiments, the light guide 1546 is configured to produce one or more wide beams of electromagnetic radiation (e.g., via diffused exit openings). Said another way, the electromagnetic radiation cone of each opening in the light guide 1546 may have a wide angle. In some embodiments, the light source 1548 is configured to emit pulses of electromagnetic radiation (e.g., a series of less than 100 microsecond pulses or pulses about 200 microseconds apart plus or minus 100 microseconds).

The plurality of sensors 1554 of the sensing module 1550 are mounted on, or otherwise disposed on, a PCB 1552. The PCB 1552 may be any standard PCB made by any commonly known process and may be the same or similar to the PCB 252 described above with reference to the dose management system 200. The sensing module 1550 or, specifically, the plurality of sensors 1554, may be the same as or similar to the sensing module 250 or the plurality of sensors 254, respectively, described above with reference to the dose management system 200. The plurality of sensors 1554 may be any optical sensors (e.g., photodiodes) optically coupleable with the light guide 1546 and configured to detect at least a portion of the electromagnetic radiation distributed by the light guide 1546. The electromagnetic radiation may be transmitted radiation, refracted radiation (e.g., refracted through air, drug, and/or body of drug delivery device), reflected radiation (e.g., reflected from a wall of the housing 1520 and/or internally reflected from a wall of the drug delivery device), and/or multi-directional refraction/reflection (e.g., caused by a lensing effect of a curved surface of the housing and/or the drug reservoir). The transmitted, refracted, and/or reflected electromagnetic signal received by the plurality of sensors 1554 may be used to create a signal signature (e.g., by the processing unit). For example, the signal signature can then be associated with a reference signature to determine the volume or number of doses remaining in the drug delivery device. In some embodiments, the signal response of the sensors 1554 is used to measure usability metrics such as, for example, determining the presence of the injector of the drug delivery device, and/or determining whether the drug delivery device is coupled or uncoupled to the dose measurement system 1500. In some embodiments, the number of the plurality of sensors 1554 is one or greater than one. In some embodiments, the light guide 1546 and/or sensors 1554 are arranged in an inclined orientation. In some embodiments, the plurality of sensors are disposed in a substantially straight line that is substantially parallel to the elongate axis of the light guide.

Figure 23:
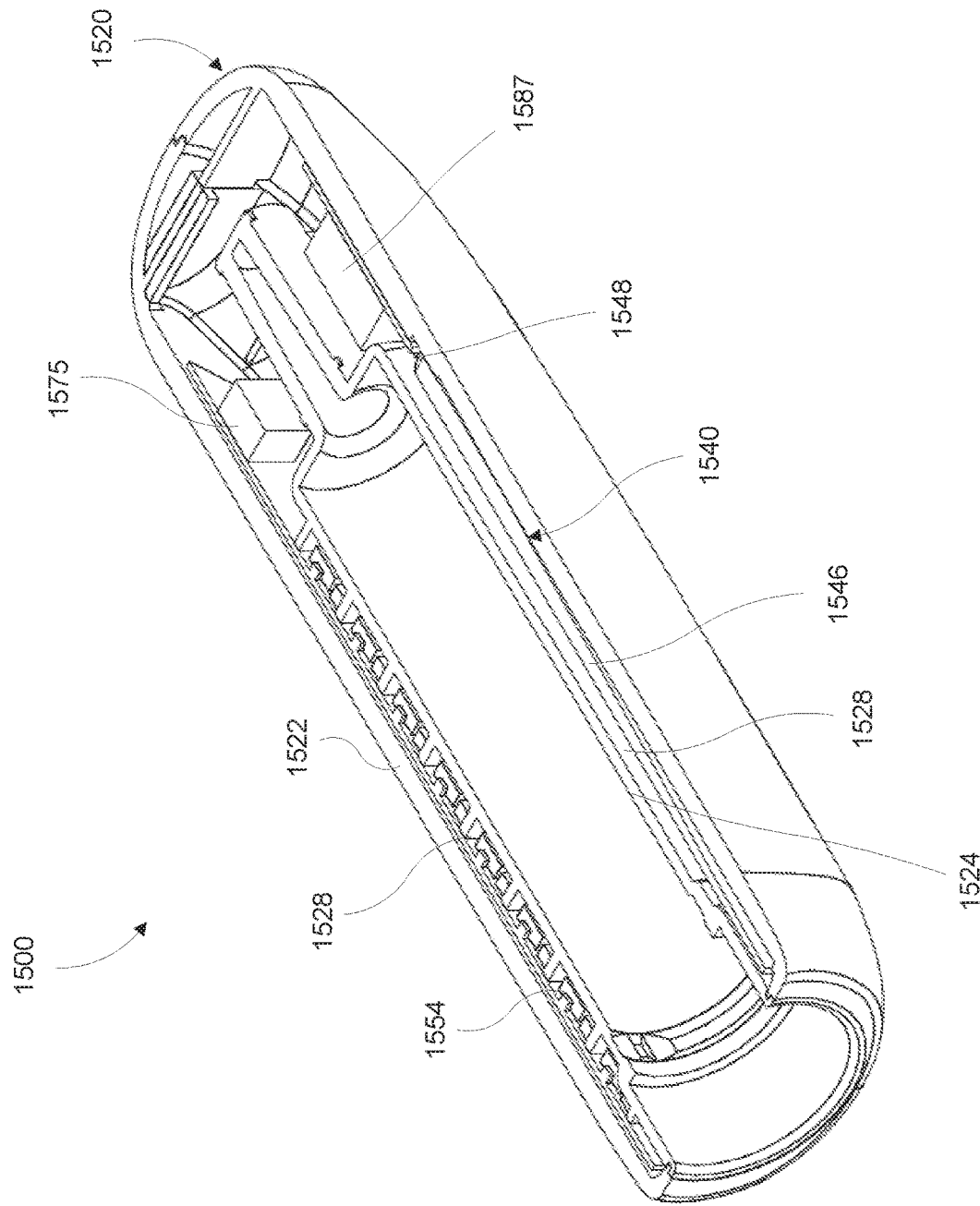
FIG. 23 is a cross-sectional perspective view of the dose measurement system of FIG. 18 in accordance with some embodiments.

FIGS. 23 and 24 are a cross-sectional perspective view and a cross-sectional side view, respectively, of the dose measurement system 1500. As shown in FIGS. 23 and 24, the second housing 1524 can define apertures 1528 for receiving at least a portion of the light guide 1546 of the lighting module 1540 and/or sensors 1554 of the sensing module 1550. The apertures 1528 may be configured to provide mechanical support for the light guide 1546 and/or sensors 1554, or can serve as an alignment mechanism for the lighting module 1540 and/or sensing module 1550.

As described herein, the electromagnetic radiation signal received by the plurality of sensors 1554 of the sensing module 1550 may include a combination of the transmitted, refracted and reflected portions of the electromagnetic radiation distributed by the light guide 1546. A unique signal signature is produced by the combination of the portions of the electromagnetic radiation at different dose volumes remaining, and/or the actuator position of the drug delivery device. This signal signature may be compared with a reference signal signature database (also referred to herein as "a calibration curve") to obtain the volume or number of doses remaining in drug delivery device, as described in further detail herein.

As described above, the light module 1540 includes only a single light source 1548 in combination with the light guide 1546. Compared to embodiments that include multiple discrete light sources which each have component-to-component variation, the use of a single light source 1548 in combination with the light guide 1546 reduces the component-to-component variability of the light module 1540 to zero. Said another way, the use of the light module 1540, and particularly a single light source 1548, eliminates the need to compensate for the variation between multiple discrete light sources. Additionally, the light guide 1546 is configured, as described above, to reduce or eliminate the variation of electromagnetic radiation (i.e. the electromagnetic radiation distribution profile from the light guide 1546) along the length of the device among separate and distinct dose measurement systems 1500. The light guide 1546 may be arranged and/or formed such that is distributes electromagnetic radiation in a repeatable profile. Similarly, the light source 1548 may be arranged such that the light source 1548 directs electromagnetic radiation into the end wall 1545 of the light guide 1546 at substantially the same angle in all dose measurement systems 1500. The light guide 1546 can then distribute the electromagnetic radiation from the light source 1548 across the length of the light guide 1546 to create a "bar" of light where the proportion of electromagnetic radiation received from different areas of the light guide 1546 is substantially equal and/or repeatable.

Consider two dose measurement systems similar to system 1500: a first dose measurement system 1500a and a second dose measurement system 1500b. Due to possible variation in the brightness of light sources (e.g., LEDs) used as the single light source 1548, the magnitude of the electromagnetic radiation (e.g., the brightness of the light) received by the plurality of sensors 1554a from the light guide 1546a in the first dose measurement system 1500a can vary from the magnitude of the electromagnetic radiation received by the plurality of sensors 1554b from the light guide 1546b in the second dose measurement system 1500b. This variation in the magnitude of the electromagnetic radiation from the light source 1548 may be compensated for by the sensing module and/or the processing module easily because each of the plurality of sensors 1554a in the first dose measurement system 1500a (and each of the plurality of sensors 1554b in the second dose measurement system 1500b) will detect the same percentage change of light (e.g., the plurality of sensors 1554a in the first dose measurement system 1500a may receive 20% more light from a 20% brighter light source 1548). For example, the first dose measurement system 1500a may include six sensors that each measure a brightness value of 1.2 in a configuration where a drug delivery device and/or the second housing do not interfere with the travel of light from the first light guide to the plurality of sensors. The second dose measurement system 1500b may include six sensors that each measure a brightness value of 0.7 in a configuration where a drug delivery device and/or the second housing do not interfere with the travel of light from the first light guide to the plurality of sensors. Therefore, the single light source of the second dose measurement system 1500b is $7/12$ the brightness value of the single light source of the first dose measurement system 1500a, but the distribution profile is the same between the two dose measurement systems. Because the distribution profile is the same, the sensing module 1550 of each dose measurement system can produce the same signal signature for each dose measurement system.

Figure 25A:
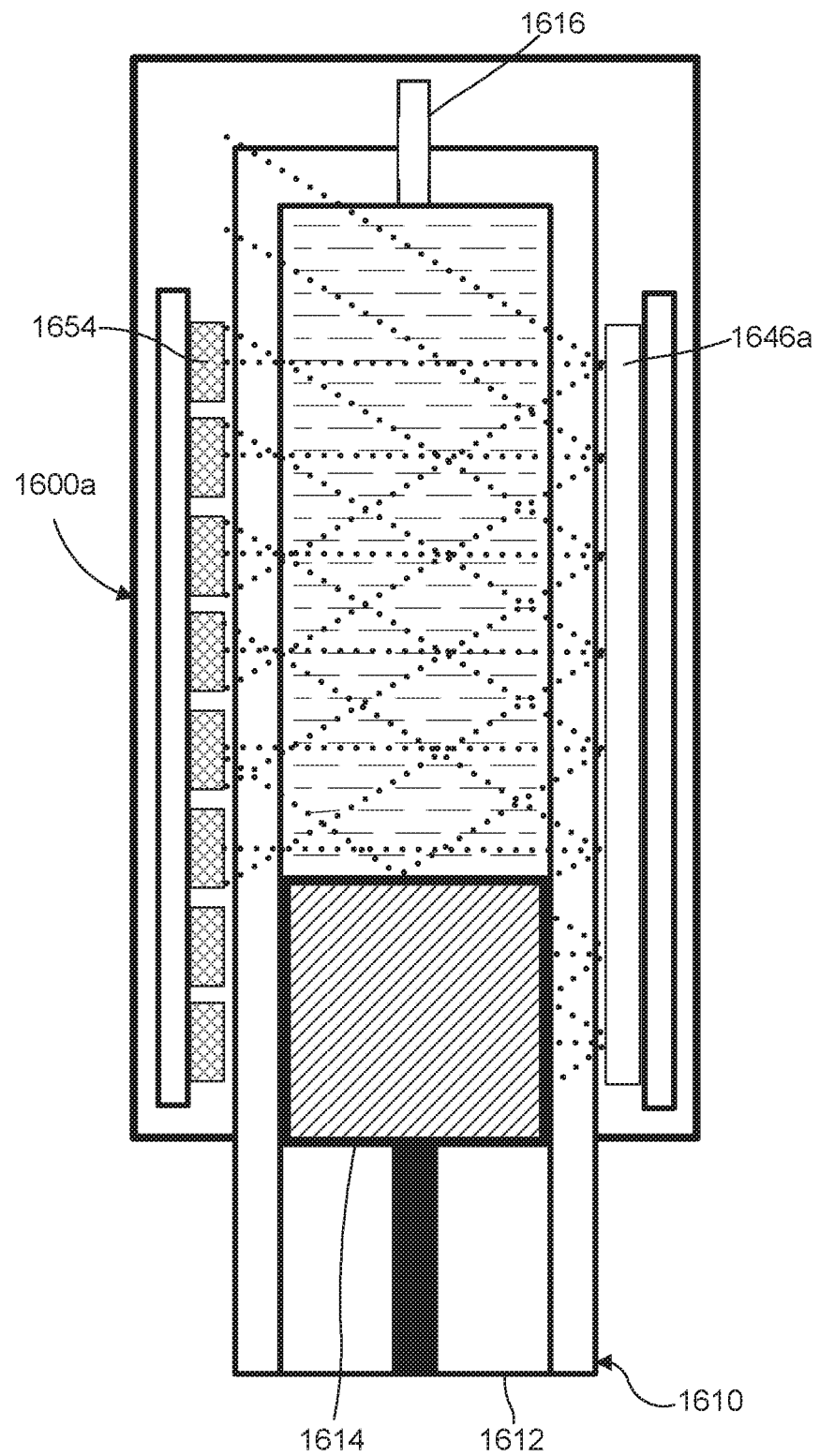
FIG. 25A is a cross-sectional schematic illustration of a dose measurement system in accordance with some embodiments.

FIG. 25A is a schematic illustration of a dose measurement system 1600a. As shown in FIG. 25A, a dose measurement system 1600a includes a light guide 1646a and a plurality of sensors 1654. While some of the transmitted and reflected portion of the electromagnetic radiation distributed by the light guide 1646a is shown, the refractive portion is not shown for clarity. A drug delivery device 1610 is coupled to the dose measurement system 1600a. The drug delivery device 1610 includes a housing 1612 and an actuator 1614 that collectively define an internal volume (e.g., a reservoir) for containing a drug. The drug delivery device 1610 also includes an injector 1616 for communicating the drug to a patient. The dose measurement system 1600a is configured such that the light guide 1646a is disposed on a first side of the housing oriented toward the drug delivery device 1610 and the plurality of sensors 1654 are disposed on a second side of the housing such that each of the plurality of sensors 1654 is substantially opposite to, and in optical communication with, a portion of the light guide 1646a. In some embodiments, the light guide 1646a and/or the plurality of sensors 1654 are disposed in a substantially linear relationship (e.g., a straight line) with respect to each other. Each of the plurality of sensors 1654 receive a combination of transmitted, refracted and reflected electromagnetic radiation distributed by the light guide 1646a. The reflection portion of the electromagnetic radiation may be reflected from a plunger portion of the actuator 1614, and/or reflected from a housing of the dose measurement system 1600a or the housing 1612 of the drug delivery device 1610. The refraction may be from the housing 1612 and/or from the liquid drug disposed in the drug delivery device 1610. The combination of the transmitted, reflected and refracted portions of the electromagnetic radiation detected by each of the plurality of sensors yields a unique signal signature for a range of dose volumes remaining in the drug delivery device 1610.

Figure 25B:
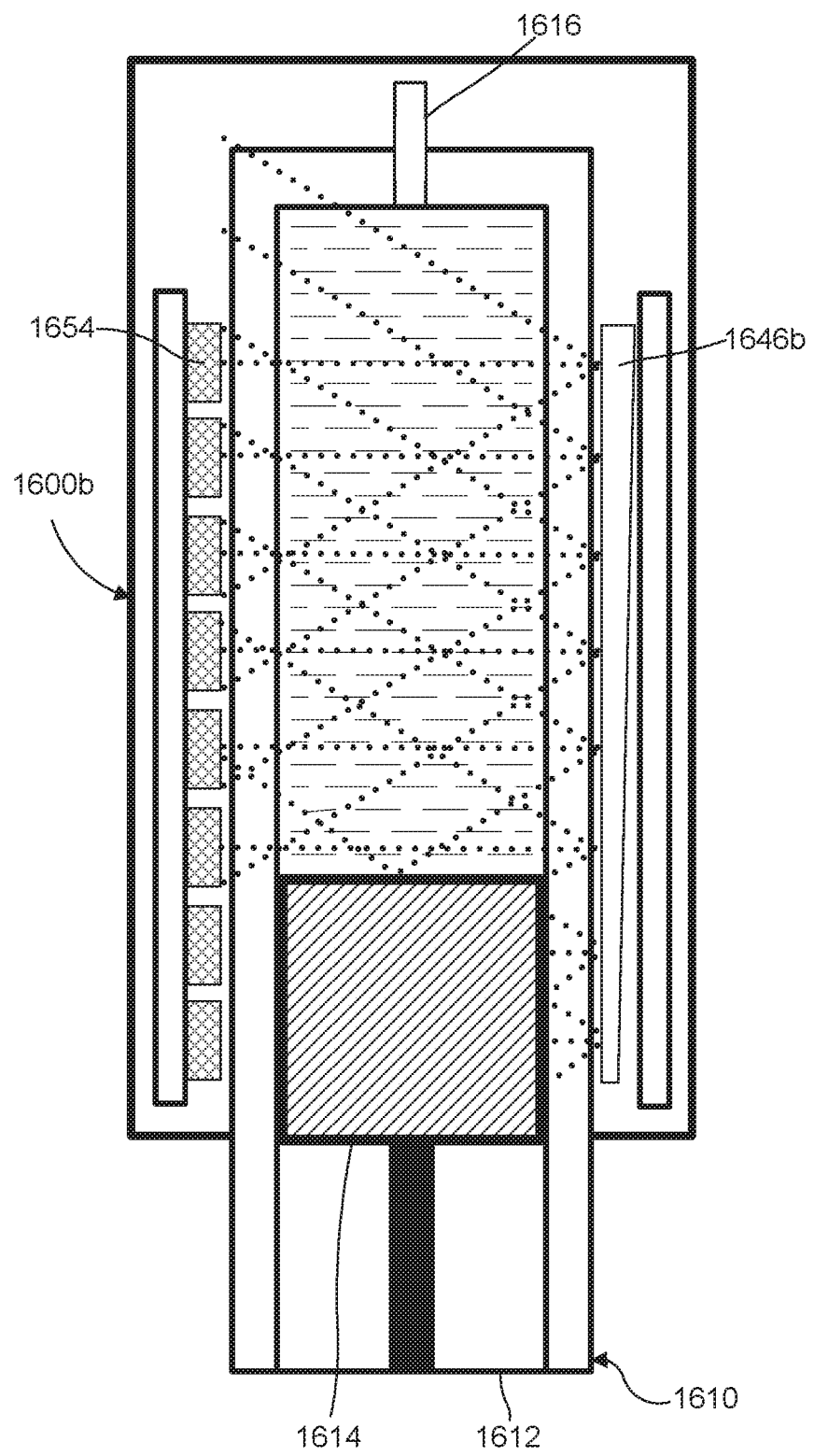
FIG. 25B is a cross-sectional schematic illustration of a dose measurement system in accordance with some embodiments.

FIG. 25B is a schematic illustration of a dose measurement system 1600b. As shown in FIG. 25B, the dose measurement system 1600b is the same in structure and function to the dose measurement system 1600a (shown in FIG. 25A), except that the dose measurement system 1600b includes a light pipe 1646b rather than light pipe 1646a. The light pipe 1646b is similar to the light pipe 1646a except that the light pipe 1646b is wedge-shaped.

Referring now to FIGS. 26A-26C, each sensor of a plurality of sensors of a dose measurement system may detect the electromagnetic radiation distributed by at least a portion of a light guide, and the detected electromagnetic radiation can be a combination of transmitted, reflected, and/or refracted electromagnetic radiation. As shown, a dose measurement system 1700 includes a light guide 1746 and two sensors 1754a and 1754b for clarity. The dose measurement system 1700 is coupled to a drug delivery device

1710 which includes a housing 1712 and an actuator 1714 that collectively define an internal volume (e.g., a reservoir) for containing a liquid drug. The drug reservoir and at least a plunger portion of the actuator 1714 are disposed substantially inside the dose measurement system 1700 between the light guide 1746 and sensors 1754a, 1754b.

As shown in FIG. 26A, the plunger portion of the actuator 1714 is in a first position (position 1) such that the plunger portion is not in the line of sight of the light guide 1746 and sensors 1754a and 1754b. When electromagnetic radiation is distributed by the light guide 1746 toward the drug delivery device 1710, a significant portion of the electromagnetic radiation is detected by the sensors 1754a and 1754b in position 1. The electromagnetic radiation may include transmitted radiation, reflected radiation (e.g., by the housing 1712 of the drug delivery device 1710) refraction (e.g., by the liquid drug and/or housing), and/or multi-direction reflection/refraction (e.g., due to a curved surface of the housing 1712 of the drug delivery device 1710) as described in more detail below. As shown in this example, sensor 1754a value is 15.3 and sensor 1754b value is 13.7, which indicates that a significant portion of the electromagnetic radiation is detected by the sensors 1754a and 1754b.

As shown in FIG. 26B, the actuator is 1714 has been displaced to a second position (position 2) such that the plunger portion partially blocks the line of sight between a portion of the light guide 1746 and the sensor 1754b. In position 2, a significant portion of the electromagnetic radiation distributed by the light guide 1746 is blocked from reaching the sensor 1754b by the actuator 1714, but at least a portion of the electromagnetic radiation distributed by the light guide 1746 can still reach the sensor 1754b along with any multi-directional reflected/refracted electromagnetic radiation. Furthermore, the sensor 1754a can receive refracted electromagnetic radiation from sensor 1744b and transmitted, refracted radiation from sensor 1744a. It also receives electromagnetic radiation reflected by a surface of the plunger that at least partially defines the drug reservoir. Therefore, at position 2 the sensor 1754a detects an electromagnetic radiation value of 15.5 (greater than position 1), and sensor 1754b detects an electromagnetic radiation value of 8.8 (less than position 1). The unique values measured at position 2 can serve as the signal signature values for position 2.

As shown in FIG. 26C, the plunger portion of the actuator 1714 is in a third position (position 3) such that the plunger portion of the actuator 1714 completely blocks the line of sight of the sensor 1754a from the electromagnetic radiation distributed by light guide 1746, such that substantially no transmitted and or reflected radiation from light guide 1746 can reach the sensor 1754a. A portion of the transmitted electromagnetic radiation distributed by light guide 1746 is also blocked by at least a portion of the actuator 1714 from reaching the sensor 1754b. Both the sensors 1754a and 1754b can still receive at least a portion of the reflected and refracted portions of the electromagnetic radiation distributed by the light guide 1746. Therefore, at position 3 the sensor 1754a detects an electromagnetic radiation value of 2.2 (less than positions 1 and 2), and sensor 1754b detects an electromagnetic radiation value of 12.0 (less than position 1, but greater than position 2). The unique values measured at position 3 can serve as the signal signature values for position 3.

Although not shown, the curvature of the drug reservoir can cause a lensing effect in the dose measurement system 1700 that is the same as or similar to the lensing effect described above with respect to the dose measurement system 700 and with reference to FIGS. 12 and 13. Similarly as described with respect to the dose management system 700, the combination of rays that reach the sensor 1754a and the sensor 1754b from the light guide 1756 in each configuration of the dose measurement system 700 with respect to the drug delivery device 1710 will produce the indicated electromagnetic radiation values in FIGS. 26A-26B. Also similarly as described above with respect to the dose measurement system 700, although the sensor values for particular positions are described as being absolute values, individual sensor values relative to other sensor values may be used to infer and/or determine the volume of liquid remaining in the drug reservoir. For example, sensor 1754a having a particular value that is different from sensor 1754b value by a certain amount or a certain percentage may be indicative of a position/drug volume remaining. Furthermore, a sensor value relative to two or more other sensor values may be used to generate a calibration curve of a drug delivery device 1710.

Figure 27:
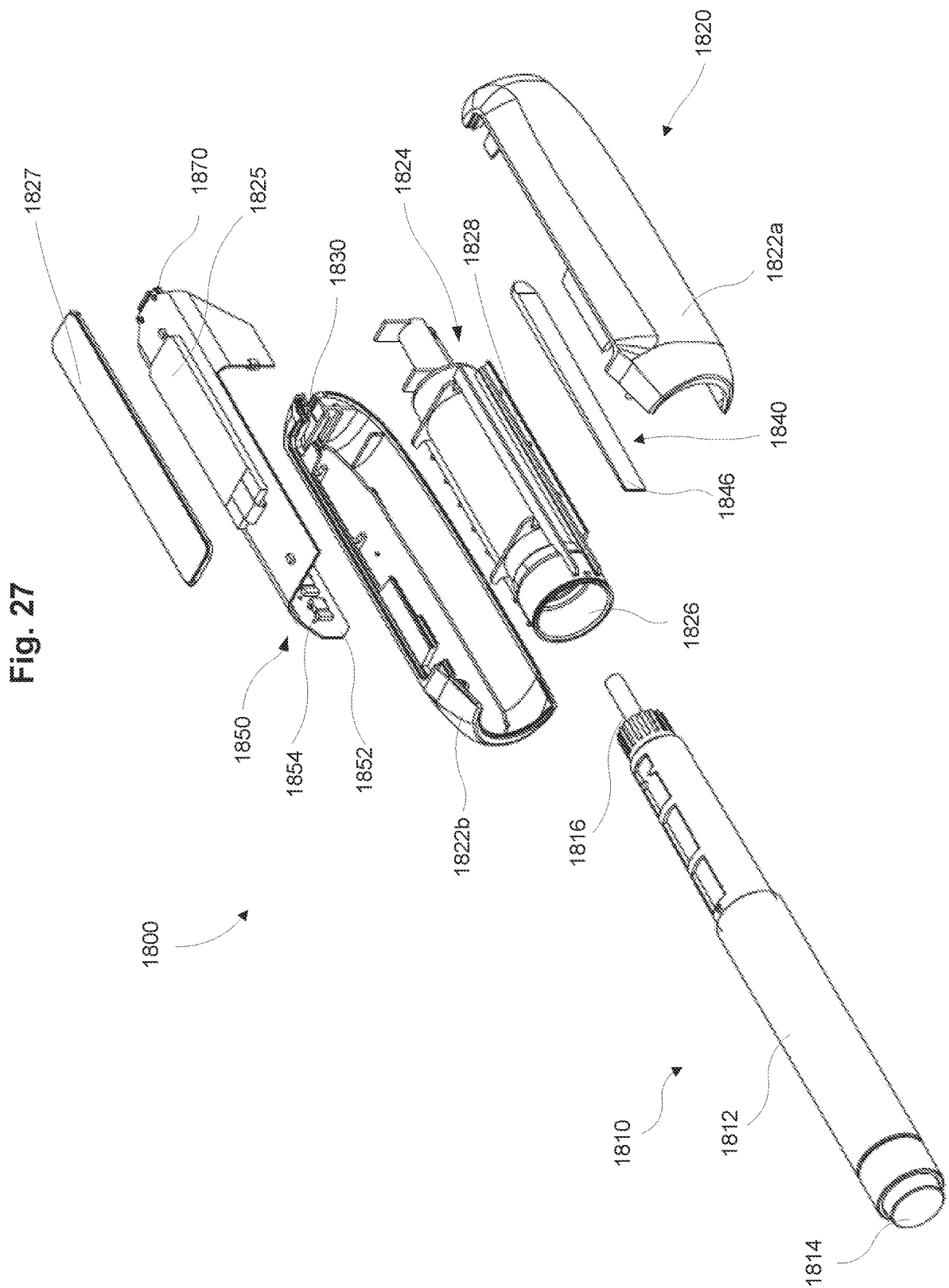
FIG. 27 is an exploded perspective view of a drug delivery device with a dose measurement system in accordance with some embodiments.

FIG. 27 is an exploded perspective view of a drug delivery device 1810 with a dose measurement system 1800. The dose measurement system 1800 includes a lighting module 1840, a sensing module 1850, a processing unit (not shown), a communications module 1870, and a power source (not shown) in accordance with some embodiments. The dose measurement system 1800 also includes a display assembly 1825 and a display lens 1827. The display assembly 1825 may include a light emitting diode (LED). The lighting module 1840 may include a light source (not shown) and a light guide 1846. The sensing module 1850 may include a plurality of sensors 1854. The dose measurement system 1800 may be configured to be removably coupleable to the drug delivery device 1810 (also referred to herein as "an injection pen 1810"). The drug delivery device 1810 may be configured to deliver a predefined quantity of a drug (e.g., a dose) to a patient. Examples of the drug delivery device 1810 include insulin injection pens that can be used by a patient to self-administer insulin. As described herein, the drug delivery device 1810 may include a housing 1812, an actuator 1814, and an injector 1816. The housing 1812 may be relatively opaque, such that it only allows select wavelengths of electromagnetic radiation to be transmitted therethrough (e.g., infrared or microwave radiation). The housing 1810 defines an internal volume (e.g., a reservoir) for storing a drug. The actuator 1814 may include a plunger portion in fluid communication with the drug and configured to communicate a predefined quantity of drug to the patient. The actuator 1814 may be configurable (e.g., by the user) to dispense variable quantities of the drug. The injector 1816 may be configured to penetrate a user's skin for intramuscular, subcutaneous, and/or intravenous delivery of the drug.

The dose measurement system 1800 includes a housing 1820 that includes a first housing portion 1822 (also referred to herein as "first housing 1822") and a second housing portion indicated at 1824 (also referred to herein as "second housing 1824"). The first housing portion 1822 includes a right first housing portion 1822a and a left first housing portion 1822b. At least a portion of the second housing portion 1824 may be configured to be disposed within an internal volume defined by the first housing portion 1822. The first housing portion 1822 and the second housing portion 1824 may be removably or fixedly coupled together by, for example, gluing, hot welding, a snap-fit mechanism, screws, or by any other suitable coupling means. Similarly, the right first housing portion 1822a and the left first housing portion 1822b may be removably or fixedly coupled together by, for example, gluing, hot welding, a snap-fit mechanism, screws, or by any other suitable coupling means. The housing 1820 may be made from a rigid, light weight, and opaque material, such as polytetrafluoroethylene, high density polyethylene, polycarbonate, another plastic, acrylic, sheet metal, any other suitable material, or a combination thereof. The housing 1820 also may be configured to shield the internal electronic components of the dose measurement system 1800 from environmental electromagnetic noise. For example, the housing may include an insulation structure (not shown) that is, for example, lined with aluminum or any other metal sheet or foil that can serve as an electromagnetic shield.

The first housing portion 1822 defines an internal volume for substantially housing the lighting module 1840, the sensing module 1850, the processing unit, the communications module 1870, the power source 1886, the display assembly 1825, the display lens 1827, and at least a portion of the second housing portion 1824. The second housing portion 1824 defines a bore 1826, shaped and sized to receive at least a portion of the drug delivery device 1810. For example, the bore 1826 may be shaped and sized to receive only the drug containing portion of the housing 1812 and the injector 1816 of the drug delivery device 1810. The bore 1826 may be configured to receive the drug delivery device 1810 in a preferred orientation, such as a preferred radial orientation. In some embodiments, the bore 1826 is in close tolerance with the diameter of the drug delivery device 1810, for example, to form a friction fit with the drug delivery device 1810. In some embodiments, the bore 1826 includes one or more notches, grooves, detents, any other snap-fit mechanism, and/or threads, for removably coupling the drug delivery device 1810 to the second housing 1824. In some embodiments, the second housing portion 1824 includes one or more alignment features to allow the drug delivery device 1810 to be coupleable with the dose measurement system 1800 in a predetermined radial orientation.

The right first housing portion 1822*a* and the left first housing portion 1822*b* collectively define an opening 1830 for receiving at least a portion of the communications module 1870 such as, for example, a communication interface to provide wired communication with an external device and/or an interface for charging the power source 1886. In some embodiments, the right first housing portion 1822*a* and the left first housing portion 1822*b* also include features (e.g., recesses, apertures, cavities, etc.) for receiving a portion of the drug delivery device 1810 such as the injector 1816. In some embodiments, the housing 1820 also includes a detection mechanism (not shown) to detect if the drug delivery device 1810 has been coupled to the dose measurement system 1800 (e.g., a push switch, a motion sensor, a position sensor, an optical sensor, a piezoelectric sensor, an impedance sensor, or any other suitable sensor). The housing 1820 may be relatively smooth and free of sharp edges. In some embodiments, the housing 1820 is shaped to resemble a pen cap that has a form factor that occupies minimal space (e.g., can fit in the pocket of a user). In some embodiments, the housing 1820 also includes features (e.g., clips for attaching to a user's shirt pocket) and/or other ornamental features. In some embodiments, the dose measurement system 1800 also may serve as a replacement cap for the drug delivery device 1810.

The processing unit may include a PCB (not shown) and a processor (not shown). The processing unit may be the same or similar to the processing unit 1560 described above with reference to the dose measurement system 1500 described above and will not be further described herein.

The communications module 1870 may be the same as or similar to the communications module 1570 described above with reference to the dose measurement system 1500 and will not be further described herein. For example, the communications module 1870 may include a speaker (not shown) for providing audible alerts or messages to the user, including, but not limited to, dose reminders, reinforcement messages, and/or a microphone (not shown) for receiving audio input from the user. The power source may be any power source that can be used to power the dose measurement system 1800. The power source may be the same or similar to the power source 1586 described above with respect to the dose measurement system 1500 and will not be further described herein. In some embodiments, the dose measurement system 1800 includes a capacitor (not shown).

The light guide 1846 and the light source of the light module 1840 can be the same or similar to the light guide 1546 of the light module 1540 and will not be further described herein. The plurality of sensors 1854 of the sensing module 1850 are mounted on, or otherwise disposed on, a PCB 1852. The PCB 1852, the plurality of sensors 1854, and the sensing module 1850 can the same or similar to the PCB 1552, the plurality of sensors 1554, and the sensing module 1550 and will not be further described herein.

The second housing 1824 can define apertures 1828 for receiving at least a portion of the light guide 1846 of the lighting module 1840 and/or sensors 1854 of the sensing module 1850. The apertures 1528 may be configured to provide mechanical support for the light guide 1546 and/or sensors 1554, or can serve as an alignment mechanism for the lighting module 1540 and/or sensing module 1550.

Figure 28:
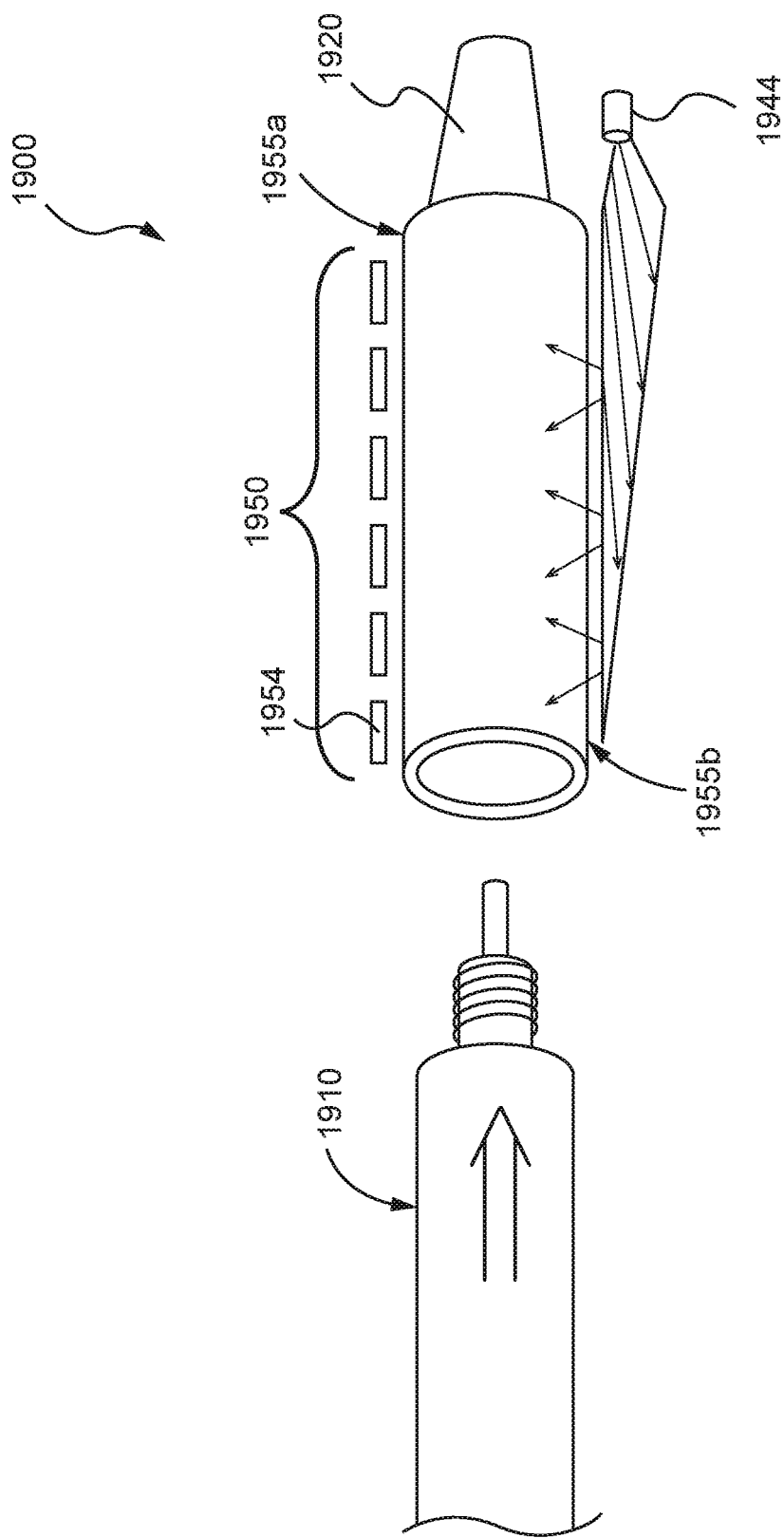
FIG. 28 is a schematic illustration of a dose measurement system, in accordance with some embodiments.

FIG. 28 is an illustration of a dose measurement system 1900 that can be structurally and/or functionally similar to the dose measurement system 200 as shown in FIGS. 2-4, according to some embodiments. In some embodiments, the light guide can be disposed on a light guide axis such that the light guide axis is substantially parallel to a longitudinal axis defined by the dose measurement system 1900. The light source 1944 can be disposed at an angle such that the light source 1944 is facing downward (toward the injection pen 1910) and is configured to emit electromagnetic radiation along the light guide axis. The sensors 1954 can be disposed on a sensor axis such that the sensor axis is substantially parallel to the longitudinal axis defined by the dose measurement system 1900. That is light source 1944 is configured to emit electromagnetic radiation approximately in a perpendicular direction to the sensors 1952. Said another way, the sensors 1954 can be disposed on a first side 1955*a* of the dose measurement system 1900 facing a second side 1955*b* of the dose measurement system 1900 and the light guide can be disposed substantially parallel to the second side 1955*b* of the dose measurement system 1900. The light source 1944 can be disposed on the second side 1955*b* of the dose measurement system such that the light source 1944 is facing the injection pen 1910 and such that the light source 1944 can emit electromagnetic radiation along the light guide. In some embodiments, the light source 1944 can be disposed at an angle of about 90 degrees, about 100 degrees, about 110 degrees, about 120 degrees, about 130 degrees, about 140 degrees, about 150 degrees, about 160 degrees, about 170 degrees, or about 180 degrees, inclusive of all ranges therebetween with respect to the longitudinal axis of the dose measurement system 2800.

In some embodiments, the dose measurement system 1900 can include at least one opening or area on the second side 1955*b* of the dose measurement system 1900 such that the second side 1955b is opposite to and facing the first side 1955a of the dose measurement system 1900. The opening or area may be configured to distribute at least a portion of the electromagnetic radiation emitted by the light source 1944. In some embodiments, the dose measurement system 1900 can include a light guide on the second side 1955b of the dose measurement system 1900 that is configured to distribute at least a portion of the electromagnetic radiation emitted by the light source 1944. In some embodiments, the light guide is disposed such that the elongated axis of the light guide is substantially parallel to the sensors 1954. In some embodiments, the light guide is disposed such that each opening or area for transmitting electromagnetic radiation is located parallel to at least one sensor.

In some embodiments, the downward angling of the light source 1944 such that the light source is not directly facing the sensors 1954 can be configured to cause electromagnetic radiation emitted by the light source 1944 to be scattered. The scattered portions of the electromagnetic radiation may be detected by the plurality of sensors 1954. In some embodiments, at least a portion of the electromagnetic radiation emitted by the light source 1944 may be detected by the sensors 1954. In some embodiments, the light guide and/or at least the opening or the area on the second side of the dose measurement system 1900 can be configured to distribute the scattered portions of the electromagnetic radiations in a manner such that the scattered portions may be detected by the sensors 1954.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All publications, patent applications, patents, and other references mentioned herein are incorporated by reference in their entirety.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method comprising:
   causing a light source to emit electromagnetic radiation into a light guide such that the light guide scatters the received electromagnetic radiation at random angles into a wide radiation pattern and directs the scattered electromagnetic radiation toward the drug container;
   detecting a signature of the scattered electromagnetic radiation transmitted through the drug container with a plurality of sensors optically coupleable to the light guide; and
   comparing the signature to a plurality of reference signatures to determine a position of an actuator of a drug delivery device.

2. The method of claim 1, wherein detecting the signature of the scattered electromagnetic radiation transmitted through the drug container includes detecting at least a portion of the scattered electromagnetic radiation with each of the plurality of sensors.

3. The method of claim 2, wherein data representative of at least the portion of the scattered electromagnetic radiation detected by two or more of the plurality of sensors is compiled into the signature.

4. The method of claim 1, further comprising:
   correcting the signature for background light.

5. The method of claim 1, wherein the light source is the only light source caused to emit electromagnetic radiation into the light guide.

6. The method of claim 5, wherein the correction includes comparing the signature with a background signature representative of electromagnetic radiation detected by the plurality of sensors in a dark state of the light source.

7. The method of claim 1, wherein the scattered portion of the electromagnetic radiation scattered by the light guide is pulsed.

8. The method of claim 1, wherein the scattered portion of the electromagnetic radiation scattered by the light guide has a select wavelength.

9. The method of claim 1, further comprising the light guide directing the received electromagnetic through a diffused exit opening that includes a random indicia of refraction, wherein the diffused exit opening is configured to present random critical angles to internal light rays.

10. A system configured to be removably coupleable to a drug delivery device that includes a drug reservoir and an actuator, the system comprising:
    a light source disposed and configured to emit electromagnetic radiation;
    a light guide disposed and configured to receive at least a portion of the emitted electromagnetic radiation, the light guide configured to scatter the received electromagnetic radiation at random angles into a wide radiation pattern and configured to direct the scattered portions of the electromagnetic radiation toward the drug reservoir;
    a plurality of sensors optically coupleable to the light guide, each sensor of the plurality of sensors disposed and configured to detect at least one of the scattered portions of the electromagnetic radiation, the quantity of electromagnetic radiation communicated through the drug reservoir being a signature representative of a position of the actuator of the drug delivery device.

11. The system of claim 10, wherein data representative of at least the portion of the scattered electromagnetic radiation detected by two or more of the plurality of sensors is compiled into the signature.

12. The system of claim 10, wherein the measurement system is configured to correct the signature for background light.

13. The system of claim 10, wherein the measurement system is configured to compare the signature with a background signature representative of electromagnetic radiation detected by the plurality of sensors in a dark state of the light source.

14. The system of claim 10, wherein the light source is the only light source configured to emit electromagnetic radiation into the light guide.

15. The system of claim 10, wherein at least one of the scattered portions of the electromagnetic radiation scattered by the light guide is pulsed.

16. The system of claim 10, wherein at least one of the scattered portions of the electromagnetic radiation scattered by the light guide has a select wavelength.

17. The system of claim 10, wherein the light guide includes a diffused exit opening including a random indicia of refraction and is configured to present random critical angles to internal light rays.

* * * * *